(12) United States Patent
Raimann et al.

(10) Patent No.: US 10,689,385 B2
(45) Date of Patent: Jun. 23, 2020

(54) BENZIMIDAZOLO[1,2-A]BENZIMIDAZOLE CARRYING ARYL- OR ARYLNITRIL GROUPS FOR ORGANIC LIGHT EMITTING DIODES

(71) Applicant: IDEMITSU KOSAN CO., LTD., Chiyoda-ku (JP)

(72) Inventors: Thomas Raimann, Sisseln (CH); Thomas Schaefer, Liestal (CH); Masatoshi Saito, Sodegaura (JP); Heinz Wolleb, Fehren (CH); Flavio Luiz Benedito, Ludwigshafen (DE); Yuichi Nishimae, Basel (CH); Yuki Nakano, Basel (CH); Hideaki Nagashima, Basel (CH)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 123 days.

(21) Appl. No.: 15/563,072

(22) PCT Filed: Mar. 31, 2016

(86) PCT No.: PCT/IB2016/051831
§ 371 (c)(1),
(2) Date: Sep. 29, 2017

(87) PCT Pub. No.: WO2016/157113
PCT Pub. Date: Oct. 6, 2016

(65) Prior Publication Data
US 2018/0086763 A1    Mar. 29, 2018

(30) Foreign Application Priority Data
Mar. 31, 2015 (EP) ..................... 15161950

(51) Int. Cl.
| | | |
|---|---|---|
| H01L 29/08 | (2006.01) | |
| C07D 487/04 | (2006.01) | |
| C09K 11/06 | (2006.01) | |
| H01L 51/50 | (2006.01) | |
| H01L 51/00 | (2006.01) | |

(52) U.S. Cl.
CPC ............ *C07D 487/04* (2013.01); *C09K 11/06* (2013.01); *H01L 51/0072* (2013.01); *H01L 51/5016* (2013.01); *C09K 2211/1029* (2013.01); *C09K 2211/1059* (2013.01); *C09K 2211/1088* (2013.01); *C09K 2211/1092* (2013.01); *H01L 51/0073* (2013.01); *H01L 51/0074* (2013.01); *H01L 51/0085* (2013.01); *H01L 51/0094* (2013.01); *H01L 51/5072* (2013.01); *H01L 51/5076* (2013.01); *H01L 51/5096* (2013.01); *Y02E 10/549* (2013.01)

(58) Field of Classification Search
USPC .......................................................... 257/40
See application file for complete search history.

(56) References Cited

U.S. PATENT DOCUMENTS

| | | | |
|---|---|---|---|
| 2013/0092922 A1* | 4/2013 | Stoessel ............... | C07D 235/00 257/40 |
| 2014/0001446 A1 | 1/2014 | Mizuki et al. | |
| 2014/0252280 A1 | 9/2014 | Schaefer et al. | |
| 2015/0105564 A1 | 4/2015 | Adachi et al. | |
| 2015/0207083 A1 | 7/2015 | Schaefer et al. | |

FOREIGN PATENT DOCUMENTS

| | | |
|---|---|---|
| EP | 2 039 737 A2 | 3/2009 |
| EP | 3 034 506 A1 | 6/2016 |
| EP | 3 034 507 A1 | 6/2018 |
| WO | WO 2011/160757 A1 | 12/2011 |
| WO | WO 2012/130709 A1 | 10/2012 |
| WO | WO 2013/068376 A1 | 5/2013 |
| WO | WO 2013/154084 A1 | 10/2013 |
| WO | WO 2014/009317 A1 | 1/2014 |
| WO | WO 2014/044722 A1 | 3/2014 |

OTHER PUBLICATIONS

International Search Report dated Jun. 7, 2017 in PCT/IB2016/051831.
International Preliminary Report on Patentability and Written Opinion dated Oct. 3, 2017 in PCT/IB2016/051831.
Misbahul Ain Khan, et al. "Tetracyclic Heteroaromatic Systems. Part-II. Benzimidazo [1, 2-a] Benzimidazoles", Journal of Scientific and Industrial Research, vol. 43. No. 3, 2000, pp. 168-170.
Pedro Molina, et al. "Synthetic Applications of C,C-3is[Iminophosphoranes]. Preparation of [5+5] Rigid Bicyclic Guanidines and 1,3,6-Benzothiadiazepino[3,2-a] benzimidazole Derivatives", Tetrahedron, vol. 50, No. 33, 1994, pp. 10029-10036.
I.V. Kolesnikova, et al. "Reaction of N-Pentafluorophanylcarbonimidoyl Dichloride with Primary Amines", Zhurnal Organicheskol Khimii, vol. 25. No. 8, 1989. pp. 1689-1695 (with cover page. submitting English translation only).
Reddouane Achour, et al. "Syntheses Des Benzimidazolo [1,2-a] Benzimidazoles A Partic Des Benzodiazepine-1, 5Ones-2", Bulletin des Societes Chimiques Beiges, vol. 96. No. 10, 1987, pp. 787-792 (with English Abstract).

(Continued)

*Primary Examiner* — Caleb E Henry
(74) *Attorney, Agent, or Firm* — Oblon, McClelland, Maier & Neustadt, L.L.P.

(57) ABSTRACT

Novel benzimidazolo[1,2-a]benzimidazoles carrying aryl- or heteroarylnitril groups, an electronic device, comprising said novel benzimidazolo[1,2-a]benzimidazoles carrying aryl- or heteroarylnitril groups, which is preferably an electroluminescent device, a charge transport layer, a charge/exciton blocker layer, or an emitting layer comprising said novel benzimidazolo[1,2-a]benzimidazoles carrying aryl- or heteroarylnitril groups, an apparatus selected from the group consisting of stationary visual display units; mobile visual display units; illumination units; key-boards; items of clothing; furniture; wallpaper, comprising said organic electronic device, or said charge transport layer, said charge/exciton blocker layer, or said emitting layer.

14 Claims, No Drawings

(56) References Cited

OTHER PUBLICATIONS

André J. Hubert, et al. "Thermolyse und Photolyse von Benzotriazolyl-(1)-Derivaten", Chemische Berichte, vol. 103, 9170, pp. 2828-2835 (with English Abstract).
Xiaoqiang Wang, et al. "Copper-Catalyzed Aerobic Oxidative Intramolecular C-H Amination Leading to Imidazobenzimidazole Derivatives", Organic Letters, vol. 14, No. 2, 2012. pp. 452-455.
Parthasarathi Subramanian, et al. "A Unified Strategy Towards N-Aryl Heterocycles by a One-Pot Copper-Catalyzed Oxidative C-H Amination of Azoles", European Journal of Organic Chemistry, 2014. pp. 5986-5997.
Guodong Yuan, et al. "An efficient and facile synthesis of benzimidazo [1,2-a] benzimidazoles via copper-catalyzed domino addition/double cyclization", RSC Advances, vol. 4 2014, pp. 21904-21908.
Shitong Zhong, et al. "Enhances proportion of radiative excitons in non-doped electro-fluorescence generated from an imidazole derivative with an orthogonal donor-acceptor structure". Chemical Communications. vol. 49, No. 96, 2013. pp. 11302-11304.
Shitong Zhong, et al. "Achieving a Significantly Increased Efficiency in Nondoped Pure Blue Fluorescent OLED: A Quasi-Equivalent Hybridized Excited State", Advanced Functional Materials, vol. 25, No. 11, 2015, pp. 1755-1762.

\* cited by examiner

BENZIMIDAZOLO[1,2-A]BENZIMIDAZOLE CARRYING ARYL- OR ARYLNITRIL GROUPS FOR ORGANIC LIGHT EMITTING DIODES

The present invention relates to compounds of formula I and their use in electronic devices, especially electroluminescent devices. When used as charge transport material, charge blocker material and/or host material in electroluminescent devices, the compounds of formula I may provide improved efficiency, stability, manufacturability, or spectral characteristics of electroluminescent devices and reduced driving voltage of electroluminescent devices. Also, said compounds of formula I show low singlet triplet splitting, which makes them useful as TADF (Thermally Activated Delayed Fluorescence, *Adv. Mater.* 2014, 26, 7931-7958) emitter or TADF host materials in combination with fluorescent emitters.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

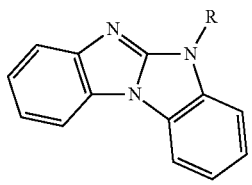

(R=H, Me, Et) by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2,a]benzimidazole derivatives.

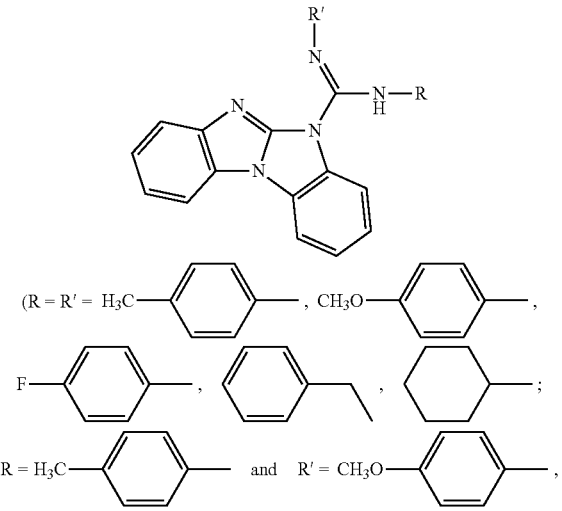

R=iso-propyl and R'=ethyl)

Kolesnikova, I. V.; Zhurnal Organicheskoi Khimii 25 (1989) 1689-95 describes the synthesis of 5H-benzimidazo[1,2-a]benzimidazole 1,2,3,4,7,8,9,10-octafluoro-5-(2,3,4,5,6-pentafluorophenyl).

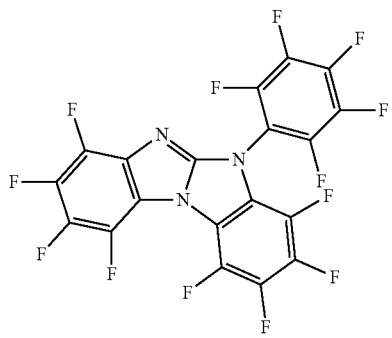 [SMILES: Fc1c(F)c(F)c(-n2c3c(F)c(F)c(F)c(F)c3n3c4c(F)c(F)c(F)c(F)c4nc23)c(F)c1F]

Achour, Reddouane; Zniber, Rachid, Bulletin des Societes Chimiques Belges 96 (1987) 787-92 describes the synthesis of benzimidazobenzimidazoles

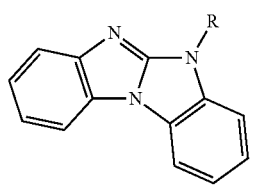

(R=H, —CH(CH$_3$)$_2$) which were prepared from benzimidazolinone derivatives.

Hubert, Andre J.; Reimlinger, Hans, Chemische Berichte 103 (1970) 2828-35 describes the synthesis of benzimidazobenzimidazoles

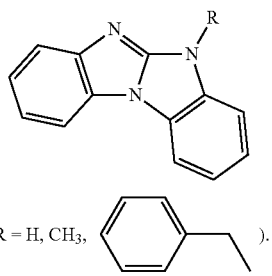

(R = H, CH$_3$, ⌬CH$_2$⌬).

X. Wang et al. *Org. Lett.* 2012, 14, 452-455 discloses a highly efficient copper-catalyzed synthesis for compounds of formula

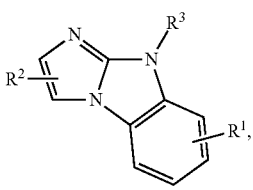

wherein compounds of formula

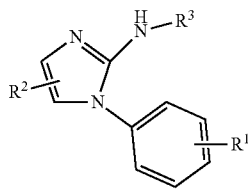

are reacted in the presence of copper acetate (Cu(OAc)₂)/PPh₃/1,10-phenanthroline/sodium acetate and oxygen in m-xylene (1 atm) at elevated temperature. Among others the following compounds can be prepared by the described synthesis method:

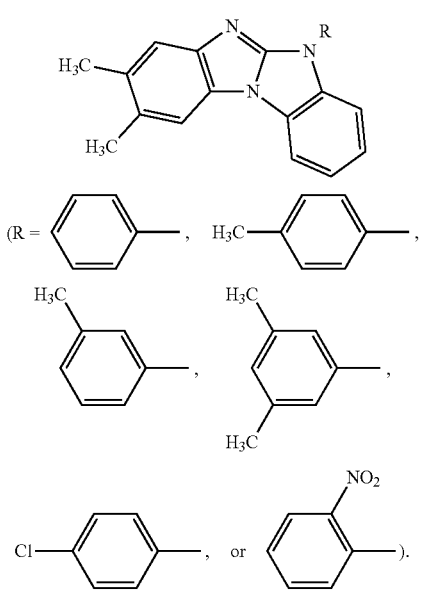

In *Eur. J. Org. Chem.* 2014, 5986-5997 a new synthesis of benzimidazolo[1,2-a]benzimidazole is described.

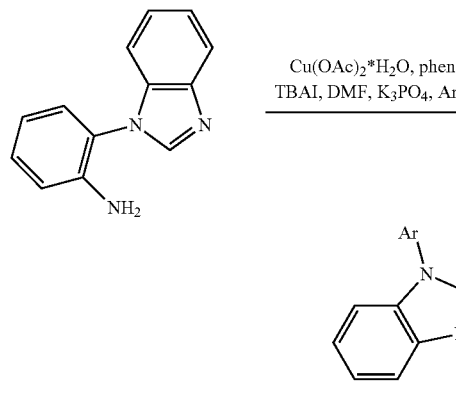

In *RSC Advances* 2014, 4, 21904-21908 a new synthesis of benzimidazolo[1,2-a]benzimidazole is described.

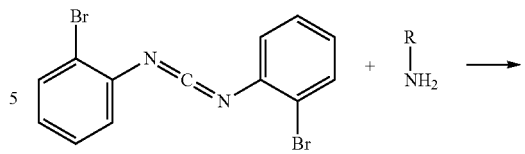

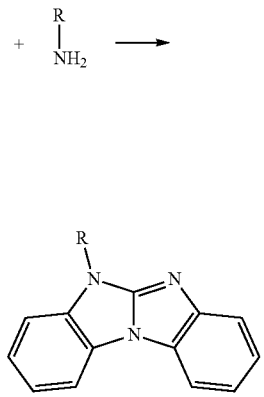

It is mentioned—as a general statement—that these polycyclic molecules have—besides other applications—also attracted great interest in the field of electroluminescent devices.

WO2011/160757 relates to an electronic device comprising an anode, cathode and at least one organic layer which contains a compound of formulae

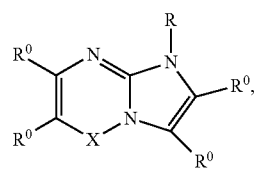 (I)

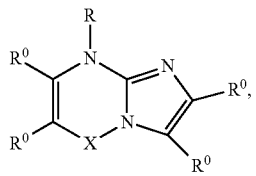 (II)

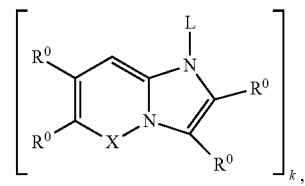 (III)

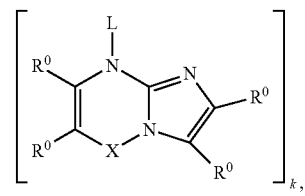 (IV)

wherein X may be a single bond and L may be a divalent group. The following 4H-Imidazo[1,2-a]imidazole compounds are explicitly disclosed:

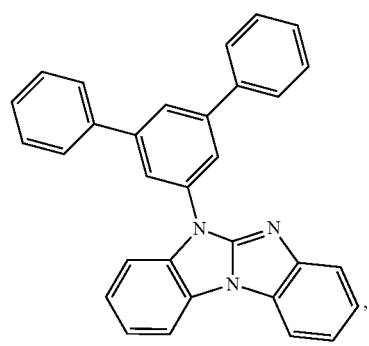
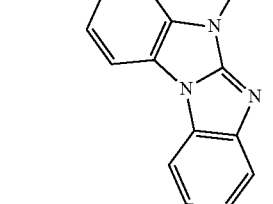
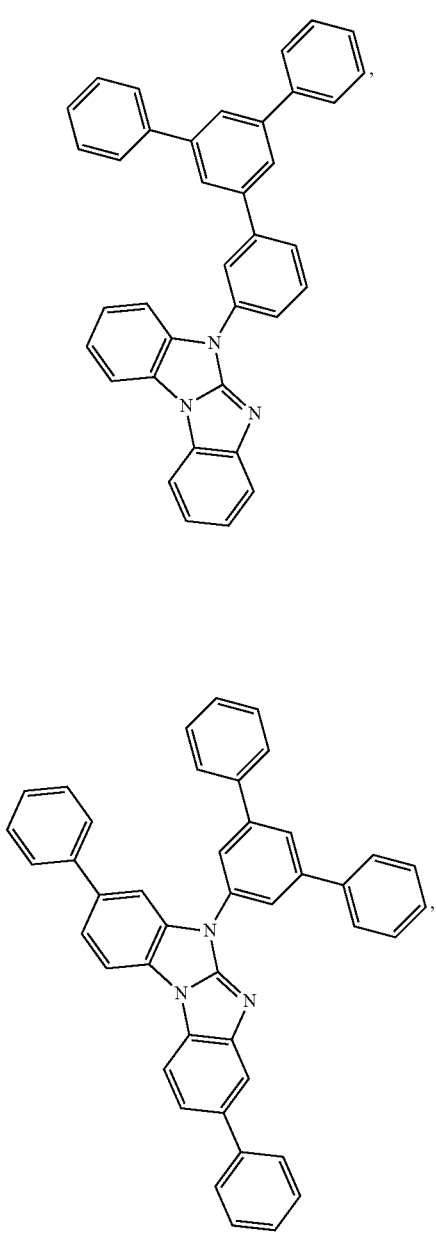
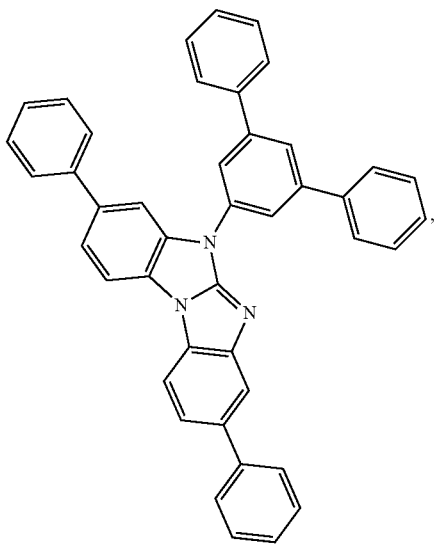
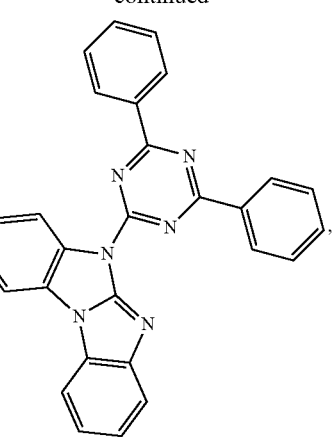
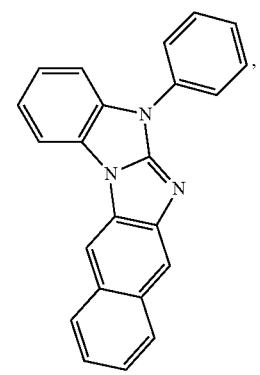
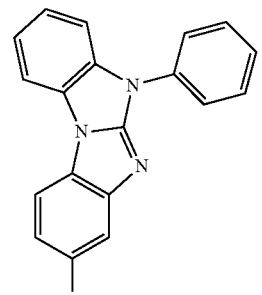
and
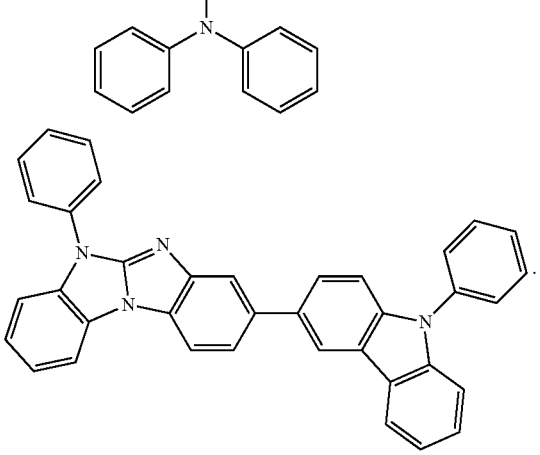

WO2012/130709 relates to 4H-Imidazo[1,2-a]imidazoles,

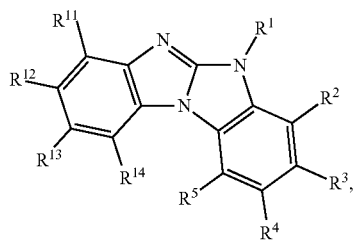

such as, for example,

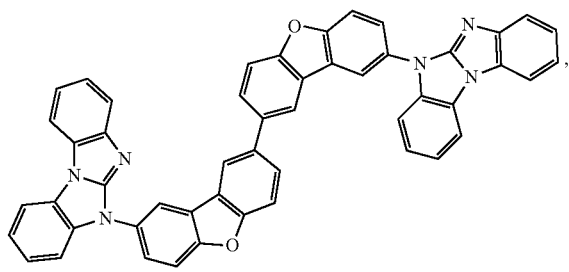
(A-1)

a process for their production and their use in electronic devices, especially electroluminescent devices.

WO2013/068376 describes 4H-imidazo[1,2-a]imidazoles of formula

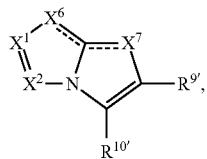

wherein $X^6$ is —N= and $X^7$ is —NR$^6$—, or $X^7$ is =N— and $X^6$ is —NR$^6$—, $R^6$ is a group of formula

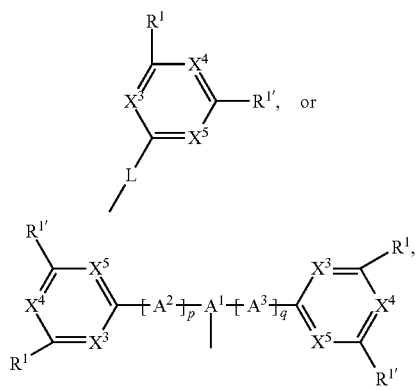

such as, for example,

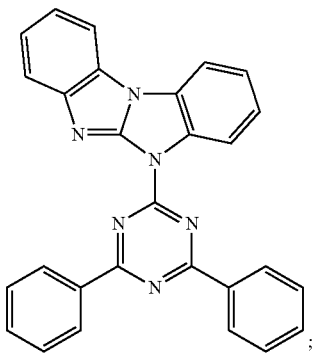 [SMILES: c1ccc(-c2nc(-c3ccccc3)nc(-n3c4ccccc4n4c5ccccc5nc34)n2)cc1]

a process for their production and their use in electronic devices, especially electroluminescent devices.

WO2014/009317 relates to compounds of formula

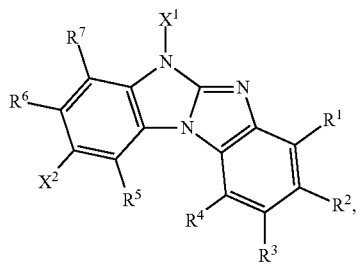
(I)

especially compounds of formula

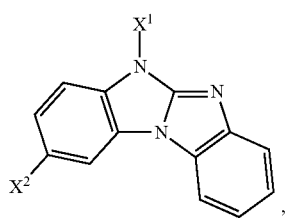
(Ia)

such as, for example,

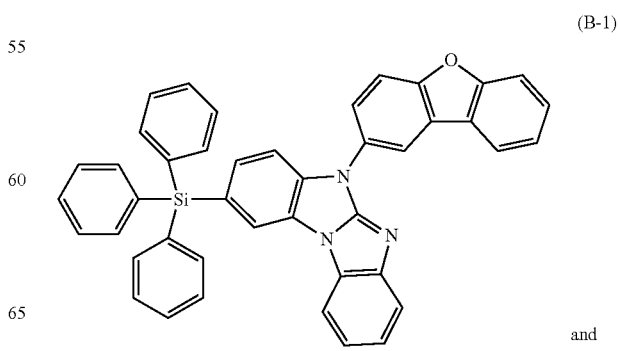
(B-1)

and

-continued

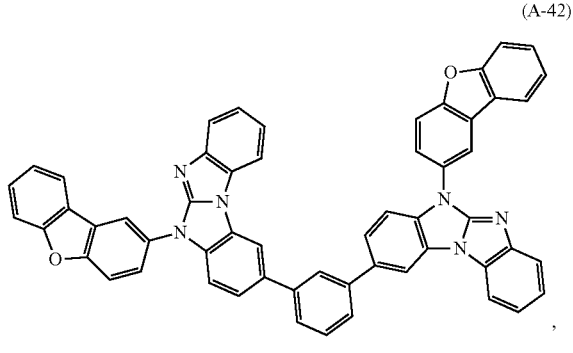
(A-42)

a process for their production and their use in electronic devices, especially electroluminescent devices. The 2,5-disubstituted benzimidazo[1,2-a]benzimidazole derivatives are suitable hole transporting materials, or host materials for phosphorescent emitters.

WO2014/044722 relates to compounds of formula

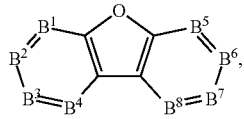
(I)

which are characterized in that they substituted by benzimidazo[1,2-a]benzimidazo-5-yl and/or benzimidazo[1,2-a]benzimidazo-2,5-ylene groups and in that at least one of the substituents $B^1$, $B^2$, $B^3$, $B^4$, $B^5$, $B^6$, $B^7$ and $B^8$ represents N, a process for their production and their use in electronic devices, especially electroluminescent devices.

European patent application no. 13191100.0 relates to compounds of formula

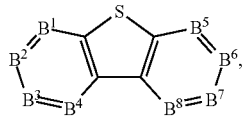
(I)

which are characterized in that they are substituted by benzimidazo[1,2-a]benzimidazo-5-yl and/or benzimidazo[1,2-a]benzimidazo-2,5-ylene groups and in that at least one of the substituents $B^1$, $B^2$, $B^3$, $B^4$, $B^5$, $B^6$, $B^7$ and $B^8$ represents N; a process for their production and their use in electronic devices, especially electroluminescent devices.

European patent application no. 14162667.1 relates to compounds of the formula

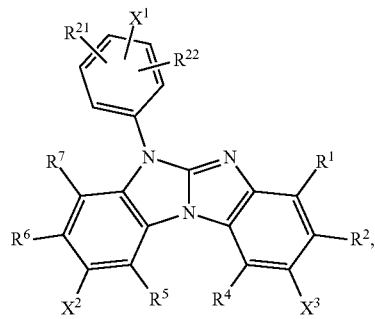
(I)

especially

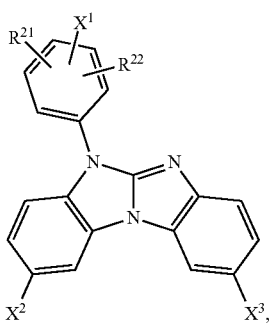
(Ia)

wherein $X^1$ is H, a group of formula

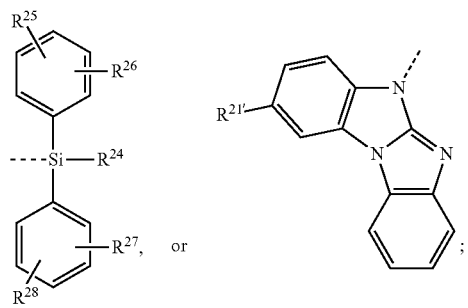

$X^2$ and $X^3$ are independently of each other H, or a group of formula

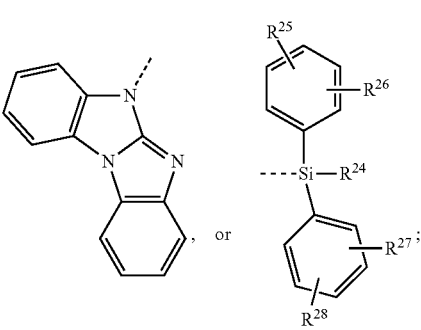

wherein at least one of $X^1$, $X^2$ and $X^3$ is a group of formula

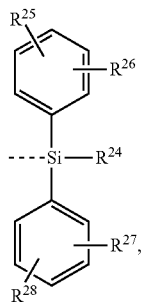

or comprises a group of formula

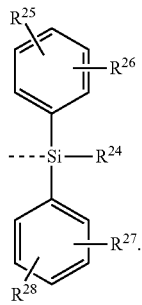

Benzimidazo[1,2-a]benzimidazo-5-yl and benzimidazo[1,2-a]benzimidazo-2-yl substituted benzimidazolo[2,1-b][1,3]benzothiazole derivatives are described in PCT/EP2014/066174. Azabenzimidazo[2,1-a]benzimidazoles for electronic applications are described in European patent application no. 14183598.3.

European patent application no. EP14197947.9 describes carbazol compounds carrying benzimidazolo[1,2-a]benzimidazole groups of the following structure.

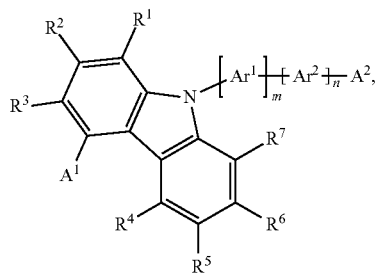

wherein
m is 1, or 2, n is 0, 1, or 2,
$Ar^1$ and $Ar^2$ are independently of each other a $C_6$-$C_{24}$aryl group, which can optionally be substituted by G, a $C_{12}$-$C_{30}$heteroaryl group, which can optionally be substituted by G, $A^1$ is a group of formula

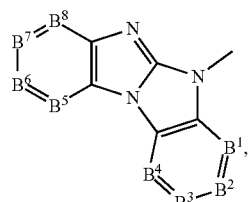

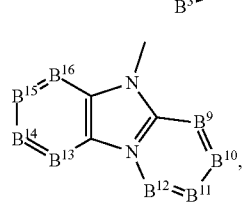

European patent application no. EP14193401.8 describes nitril-indolo compounds carrying benzimidazolo[1,2-a]benzimidazole groups. The following compound is described:

(D-54)

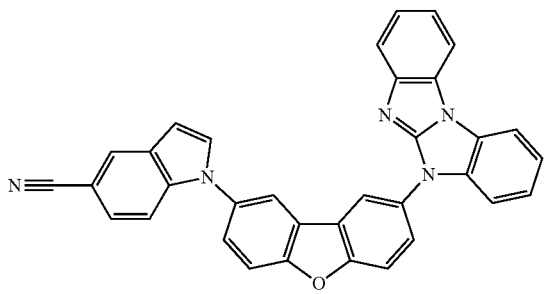

European patent application no. EP14197952.6 describes dibenzofurane compounds carrying benzimidazolo[1,2-a]benzimidazole groups of the following structure.

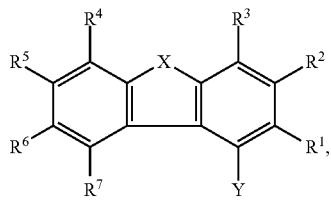

wherein
X is O or S;
Y is a group of formula —$[Ar^1]_a$—$[Ar^2]_b$—$[Ar^3]_c$-$A^1$;
$A^1$ is a group of formula

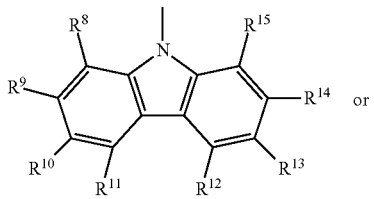

or

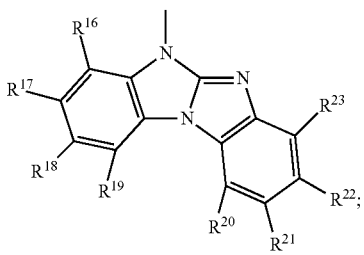

(Xb)

The following group is described.

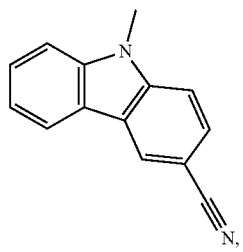 [SMILES: Cn1c2ccccc2c2cc(C#N)ccc21]

WO2013/154064 A1 discloses an organic light emitting element, which has a compound of the following formula in the light emitting layer:

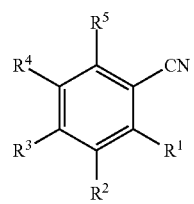

wherein at least one of $R^1$ to $R^5$ represents a cyano group, at least one of $R^1$ to $R^5$ represents a 9-carbazolyl group, a 1,2,3,4-tetrahydro-9-carbazolyl group, a 1-indolyl group or a diarylamino group, and the rest of $R^1$ to $R^5$ represent a hydrogen atom or a substituent.

EP 2 039 737 A2 concerns an organic electroluminescence device comprising a compound of formula (I)

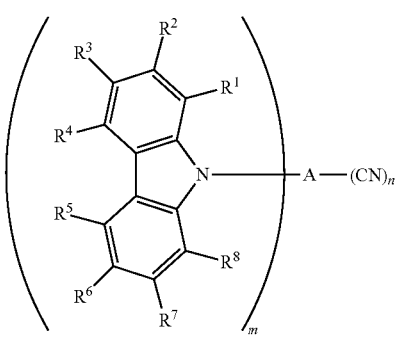

wherein a represents an aromatic ring which may have a substituent, m represents an integer of 2 or greater, and n represents an integer of 1 or greater.

Neither WO2013/154064 A1 nor EP 2 039 737 A2 disclose compounds comprising benzimidazolo[1,2-a]benzimidazole groups.

Notwithstanding these developments, there remains a need for organic light emitting devices comprising new materials, especially host (=matrix) materials, charge transport materials and/or charge/exciton blocker materials to provide improved efficiency, stability, manufacturability, driving voltage and/or spectral characteristics of electroluminescent devices. Further, there is a need for materials showing low singlet triplet splitting, which makes them useful as TADF (Thermally Activated Delayed Fluorescence, Adv. Mater. 2014, 26, 7931-7958) emitter or TADF host materials in combination with fluorescent emitters.

Accordingly, it is an object of the present invention, with respect to the aforementioned prior art, to provide further materials suitable for use in OLEDs and further applications in organic electronics. More particularly, it should be possible to provide charge transport materials, charge/exciton blocker materials and host (=matrix) materials for use in OLEDs. The materials should be suitable especially for OLEDs which comprise at least one emitter, which is preferably a phosphorescence emitter, especially at least one green emitter or at least one blue emitter. It should further be possible to provide materials showing low singlet triplet splitting, which makes them useful as TADF (Thermally Activated Delayed Fluorescence, Adv. Mater. 2014, 26, 7931-7958) emitter or TADF host materials in combination with fluorescent emitters.

Furthermore, the materials should be suitable for providing OLEDs which ensure good efficiencies, good operative lifetimes and a high stability to thermal stress, and a low use and operating voltage of the OLEDs.

Said object is solved by compounds of formula (I),

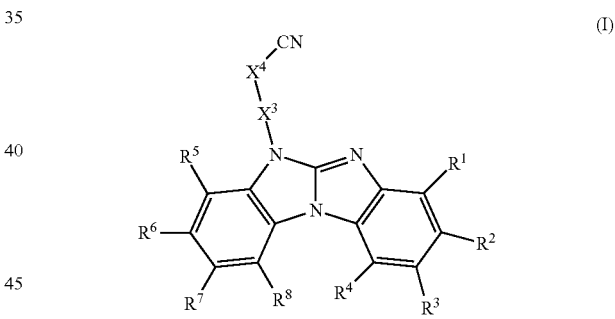

(I)

wherein
$X^3$ is a single bond or linking group of formula -$(A^1)_{o'}$-$(A^2)_{p'}$-$(A^3)_{q'}$-$(A^4)_{r'}$-,
$A^1$, $A^2$, $A^3$, $A^4$ are in each occurrence independently of each other $C_6$-$C_{24}$ arylene group which is unsubstituted or substituted by at least one group G, $C_2$-$C_{30}$ heteroarylene group which is unsubstituted or substituted by at least one group G, and
o' is 0 or 1, p' is 0 or 1, q' is 0 or 1, r' is 0 or 1, preferably o' is 0 or 1 and p' is 0 or 1, and q' and r' are 0,
$X^4$ is a single bond or

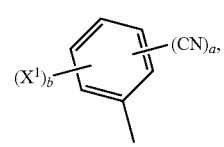

XI

-continued

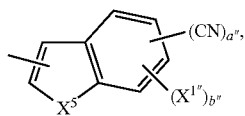

preferably

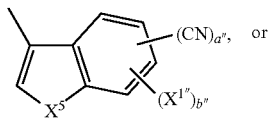

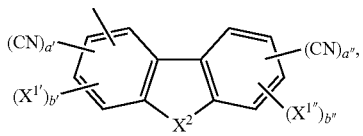

preferably,

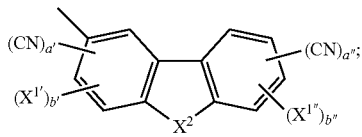

preferably, X⁴ is a single bond or

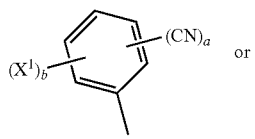

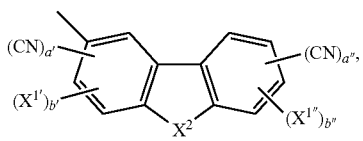

preferably,

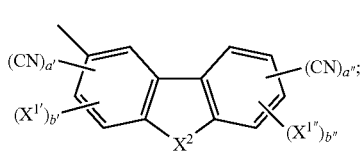

$X^2$ is O, S or $NR^{65}$, preferably $X^2$ is O, S, more preferably $X^2$ is O;

$X^5$ is O, S or $NR^{65}$, preferably $X^5$ is O, S, more preferably $X^5$ is O;

a is 0, 1, 2, 3 or 4,
b is 0, 1, 2, 3 or 4,
preferably, the sum of a+b is 1, 2 or 3, more preferably, 1 or 2, i.e. more preferably, a is 1 or 2 and b is 0, a is 1 and b is 1, or a is 0 and b is 1 or 2,
a' and a" are independently of each other 0, 1, 2 or 3,
b' and b" are independently of each other 0, 1, 2 or 3,
preferably, the sum of a"+b" is 0, 1 or 2, more preferably 0 or 1;
preferably, the sum of a'+b' is 0, 1 or 2, more preferably 0 or 1;

$X^1$, $X^{1'}$ and $X^{1''}$ are independently of each other a group of formula $-(A^1)_o-(A^2)_p-(A^3)_q-(A^4)_r-R_{10}$, in each occurrence o is 0 or 1, p is 0 or 1, q is 0 or 1, r is 0 or 1, preferably o is 0 or 1 and p is 0 or 1 and q and r are 0;

$R^{10}$ is H,

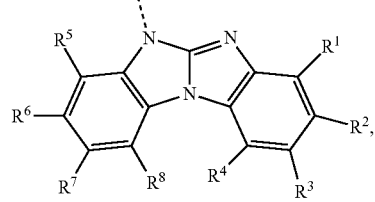

III

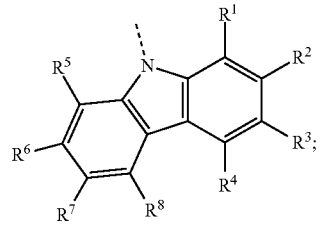

IV

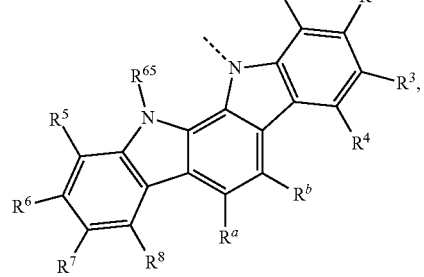

V

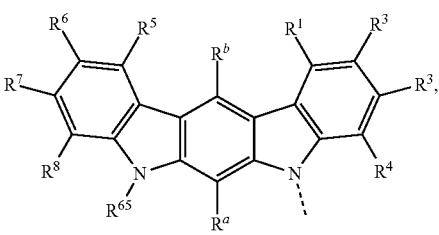

VI

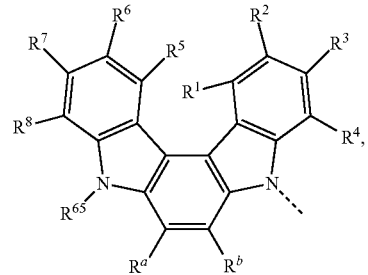

VII

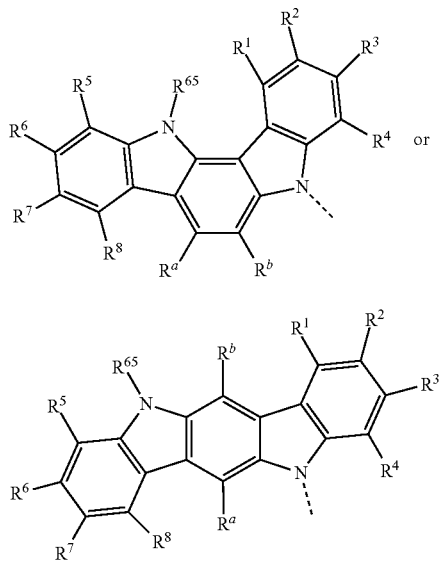

$R^1$, $R^2$, $R^3$, $R^4$, $R^5$, $R^6$, $R^7$, $R^8$, $R^9$, $R^a$ and $R^b$ are in each occurrence independently H, $C_6$-$C_{24}$aryl group which is unsubstituted or substituted by at least one group G, $C_2$-$C_{30}$ heteroaryl group which is unsubstituted or substituted by at least one group G, a $C_1$-$C_{25}$alkyl group, which is unsubstituted or substituted by at least one group E and/or interrupted by D, $C_6$-$C_{24}$ aryloxy group which is unsubstituted or substituted by at least one group G, or —$SiR^{70}R^{71}R^{72}$; or two groups $R^1$ and $R^2$ or $R^2$ and $R^3$ or $R^3$ and $R^4$ of formula IV can form together the following ring system

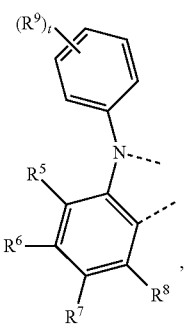

wherein t is 1 to 5;

D is —CO—, —COO—, —S—, —SO—, —$SO_2$—, —O—, —$CR^{63}$=$CR^{64}$—, —$NR^{65}$—, —$SiR^{70}R^{71}$—, —$POR^{72}$—, or —C≡C—,

E is —$OR^{69}$, —$SR^{69}$, —$NR^{65}R^{66}$, —$COR^{68}$, —$COOR^{67}$, —$CONR^{65}R^{66}$, —CN, —$SiR^{70}R^{71}R^{72}$, halogen, an unsubstituted $C_6$-$C_{24}$aryl group, a $C_6$-$C_{24}$aryl group, which is substituted by F, $C_1$-$C_{18}$alkyl, $C_1$-$C_{18}$alkyl which is interrupted by O, an unsubstituted $C_2$-$C_{30}$heteroaryl group, or a $C_2$-$C_{30}$heteroaryl group, which is substituted by F, $C_1$-$C_{18}$alkyl, $C_1$-$C_{18}$alkyl which is interrupted by O;

G is E, or a $C_1$-$C_{18}$alkyl group, or $C_1$-$C_{18}$alkyl which is interrupted by O, $R^{63}$ and $R^{64}$ are independently of each other $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl, wherein the following compound is excluded:

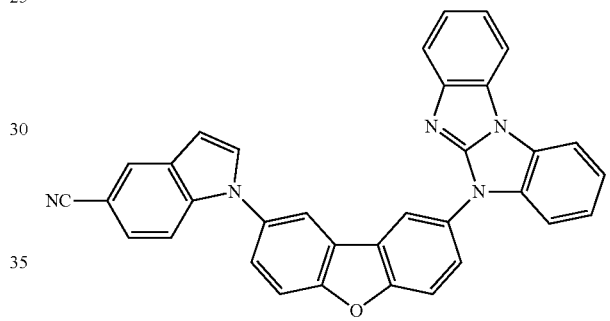

The combination of the Benzimidazolo[1,2-a]benzimidazol group having donor action with the nitril group having acceptor action gives rise to materials that are highly suitable in devices that emit green, or blue light. Moreover, the improved ambipolar characteristics give rise to more balanced charge transport in devices resulting in lower voltages and higher external quantum efficiencies (EQE's).

One key finding of the inventors of the present invention is the relevance of the position of the nitrile group, which is not directly substituted at the benzimidazolo[1,2-a]benzimidazole skeleton, but substituted at the aromatic or heteroaromatic residue $X^4$. Therefore, the compounds of the present invention are characterized by a high acceptor strength, efficient bipolar characteristics and a good suitability as TADF hosts or emitters.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device, such as an organic light-emitting diode (OLED).

The compounds of formula I can in principal be used in any layer of an EL device, but are preferably used as host, charge transport and/or charge/exciton blocking material. Particularly, the compounds of formula I are used as host material for green, especially blue light emitting phosphorescent emitters. Additionally, the compounds of formula I are used as TADF emitter or TADF host materials in combination with at least one fluorescent emitter, especially in OLEDs emitting in the blue and green region of the electromagnetic spectrum.

Hence, a further subject of the present invention is directed to a charge transport layer, comprising a compound of formula I according to the present invention.

A further subject of the present invention is directed to an emitting layer, comprising a compound of formula I according to the present invention. In said embodiment a compound of formula I is preferably used as host material, more preferably in combination with a phosphorescent emitter.

A further subject of the present invention is directed to a charge/exciton blocking layer, comprising a compound of formula I according to the present invention.

A further subject of the present invention is directed to an OLED comprising at least one compound of formula I as TADF emitter or TADF host material in combination with at least one fluorescent emitter.

The terms halogen, alkyl, alkoxy, cycloalkyl, aryl, aryloxy, aralkyl, heteroaryl, arylene, heteroarylene generally have the following meaning, if said groups are not further specified in specific embodiments mentioned below:

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_6$-$C_{24}$aryl (preferably $C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted. Phenyl, 1-naphthyl and 2-naphthyl are examples of a $C_6$-$C_{10}$aryl group.

$C_6$-$C_{24}$aryloxy, which optionally can be substituted, is typically $C_6$-$C_{10}$aryloxy, which optionally can be substituted by one, or more $C_1$-$C_8$alkyl and/or $C_1$-$C_8$alkoxy groups, such as, for example, phenoxy, 1-naphthoxy, or 2-naphthoxy.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenylethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

$C_2$-$C_{30}$heteroaryl (preferably $C_2$-$C_{13}$heteroarylaryl) represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, benzimidazolo[2,1-b][1,3]benzothiazolyl, carbazolyl, or phenoxazinyl, which can be unsubstituted or substituted. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

A $C_2$-$C_{13}$heteroaryl group is for example, benzimidazo[1,2-a]benzimidazo-5-yl

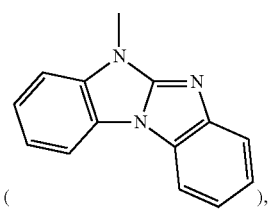 [SMILES: Cn1c2ccccc2n2c3ccccc3nc12]

benzimidazo[1,2-a]benzimidazo-2-yl

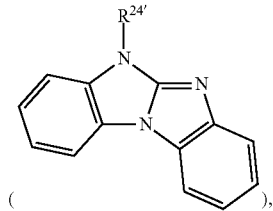

benzimidazolo[2,1-b][1,3]benzothiazolyl, benzimidazolo[2,1-b][1,3]benzoxazole, carbazolyl, dibenzofuranyl, or dibenzothiophenyl, which can be unsubstituted or substituted, especially by $C_6$-$C_{10}$aryl, or $C_6$-$C_{10}$aryl, which is substituted by $C_1$-$C_4$alkyl; or $C_2$-$C_{13}$heteroaryl.

$C_2$-$C_{30}$heteroaryl (preferably $C_2$-$C_{13}$ heteroarylaryl) means that the heteroaryl residue comprises at least 2 carbon atoms and at most 30 carbon atoms in the base skeleton (without substituents). The further atoms in the heteroaryl base skeleton are heteroatoms (N, O and/or S).

$R^{24'}$ is in each case independently $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, phenanthronyl, triphenylenyl, fluoranthenyl or biphenylyl.

$C_6$-$C_{24}$arylene groups, which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted. Preferred $C_6$-$C_{24}$arylen groups are 1,3-phenylene, 3,3'-biphenylylene, 3,3'-m-terphenylene, 2- or 9-fluorenylene, phenanthrylene, which may be unsubstituted or substituted.

$C_2$-$C_{30}$heteroarylene groups, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, benzimidazo[1,2-a]benzimidazo-2,5-ylene, or phenoxazinylene, which can be unsubstituted or substituted. Preferred $C_2$-$C_{30}$heteroarylen groups are pyridylene, triazinylene, pyrimidinylene, carbazolylene, dibenzofuranylene and benzimidazo[1,2-a]benzimidazo-2,5-ylene

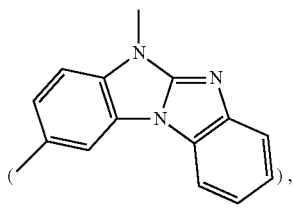 [SMILES: Cc1ccc2c(c1)n1c3ccccc3nc1n2C]

which can be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Possible preferred substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group.

The $C_6$-$C_{24}$aryl ($C_6$-$C_{18}$aryl) and $C_2$-$C_{30}$heteroaryl groups are preferably substituted by one, or more $C_1$-$C_8$alkyl groups.

If a substituent occurs more than one time in a group, it can be different in each occurrence.

Halo-$C_1$-$C_8$alkyl is an alkyl group where at least one of the hydrogen atoms is replaced by a halogen atom. Examples are —$CF_3$, —$CF_2CF_3$, —$CF_2CF_2CF_3$, —$CF(CF_3)_2$, —$(CF_2)_3CF_3$, and —$C(CF_3)_3$.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—$CH(C_2H_5)$ $C_4H_9$), $CH_2$—$CH(OR^{y'})$—$CH_2$—O—$R^y$, where $R^y$ is $C_1$-$C_{18}$alkyl, $C_6$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR_z$, $CH(CH_3)$ $COOR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—$C(CH_3)$=$CH_2$.

An alkyl group substituted by E is, for example, an alkyl group where at least one of the hydrogen atoms is replaced by F. Examples are —$CF_3$, —$CF_2CF_3$, —$CF_2CF_2CF_3$, —$CF(CF_3)_2$, —$(CF_2)_3CF_3$, and —$C(CF_3)_3$.

D is preferably —CO—, —COO—, —S—, —SO—, —$SO_2$—, —O—, —$NR^{65}$—, wherein $R^{65}$ is $C_1$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, or biphenylyl, or $C_2$-$C_{30}$heteroaryl, such as, for example, benzimidazo[1,2-a]benzimidazo-2-yl

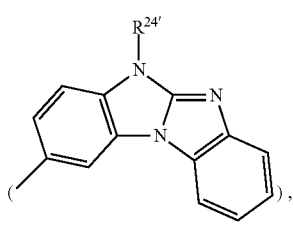

carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{13}$heteroaryl.

E is —$OR^{69}$, —$SR^{69}$, —$NR^{65}R^{66}$, —$COR^{68}$, —$COOR^{67}$, —$CONR^{65}R^{66}$, —CN, —$SiR^{70}R^{71}R^{72}$

E is preferably —$OR^{69}$; —$SR^{69}$; —$NR^{65}R^{66}$; —$COR^{68}$; —$COOR^{67}$; —$CONR^{65}R^{66}$; or —CN; wherein $R^{65}$, $R^{66}$, $R^{67}$, $R^{68}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl.

G is preferably —$OR^{69}$, —$SR^{69}$, —$NR^{65}R^{66}$; a $C_1$-$C_{18}$alkyl group, a $C_6$-$C_{14}$aryl group, a $C_1$-$C_{14}$aryl group, which is substituted by F, or $C_1$-$C_{18}$alkyl; a $C_2$-$C_{13}$heteroaryl group, or a $C_2$-$C_{13}$heteroaryl group, which is substituted by F, or $C_1$-$C_{18}$alkyl; wherein $R^{65}$, $R^{66}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl.

Preferably, a, b, a', b', a" and b" have the following meanings:

a is 0, 1, 2 or 3, b is 0, 1, 2 or 3, and the sum of a+b is 1, 2 or 3, preferably, 1 or 2;

a' and a" are independently of each other 0, 1, 2 or 3, b' and b" are independently of each other 0, 1, 2 or 3, preferably, the sum of a'+b' is 0, 1 or 2, more preferably 0 or 1, preferably, the sum of a"+b" is 0, 1 or 2, more preferably 0 or 1.

In one preferred embodiment, especially in the case that the compounds of formula I are used TADF emitters or TADF host materials in combination with fluorescent emitters, a, a' or a" are preferably 0 or 1, more preferably 0.

$X^4$ is preferably a single bond or

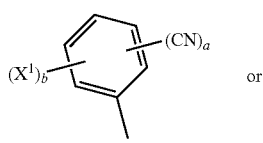

XI preferably,

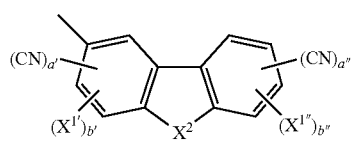

XIII

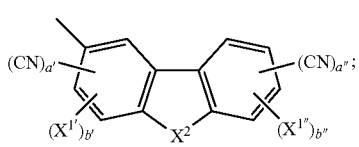

XIIIa more preferably a single bond or

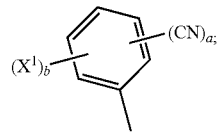

$X^2$ is O, S or $NR^{65}$, preferably $X^2$ is O, S, more preferably $X^2$ is O;

$X^5$ is O, S or $NR^{65}$, preferably $X^5$ is O, S, more preferably $X^5$ is O.

$X^3$ is preferably a single bond or a group of the following formula

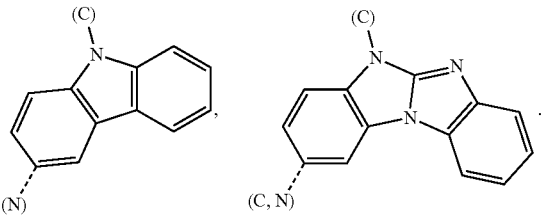

$R^1$, $R^2$, $R^3$, $R^4$, $R^5$, $R^6$, $R^7$, $R^8$ and $R^9$ are in each occurrence independently H, $C_6$-$C_{24}$ aryl group which is unsubstituted or substituted by at least one group G, $C_2$-$C_{30}$ heteroaryl group which is unsubstituted or substituted by at least one group G, a $C_1$-$C_{25}$alkyl group, which is unsubstituted or substituted by at least one group E and/or interrupted by D, $C_6$-$C_{24}$ aryloxy group which is unsubstituted or substituted by at least one group G, or —$SiR^{70}R^{71}R^{72}$;

preferably, $R^1$, $R^2$, $R^4$, $R^5$, $R^6$, $R^8$ and $R^9$ are H and $R^3$ and $R^7$ are in each occurrence independently H, $C_6$-$C_{24}$ aryl group which is unsubstituted or substituted by at least one group G, $C_2$-$C_{30}$ heteroaryl group which is unsubstituted or substituted by at least one group G, a $C_1$-$C_{25}$alkyl group, which is unsubstituted or substituted by at least one group E and/or interrupted by D, $C_6$-$C_{24}$ aryloxy group which is unsubstituted or substituted by at least one group G, or —$SiR^{70}R^{71}R^{72}$; more preferably, $R^1$, $R^2$, $R^4$, $R^5$, $R^6$, $R^8$ and $R^9$ are H and $R^3$ and $R^7$ are in each occurrence independently H or a group of the following formula:

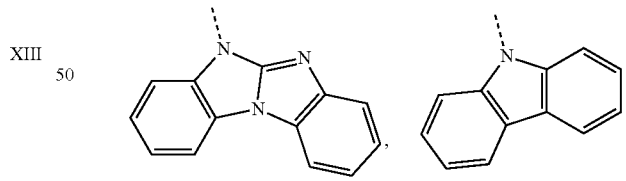

or —$SiR^{70}R^{71}R^{72}$.

$R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl; preferably, $R^{70}$, $R^{71}$ and $R^{72}$ are phenyl.

Preferably, o is in each occurrence 0 or 1 and p is 0 or 1 and q and r are 0, more preferably, o is 0 or 1 and p, q and r are 0.

$A^1$, $A^2$, $A^3$, $A^4$ are preferably in each occurrence independently of each other a group of the formula:

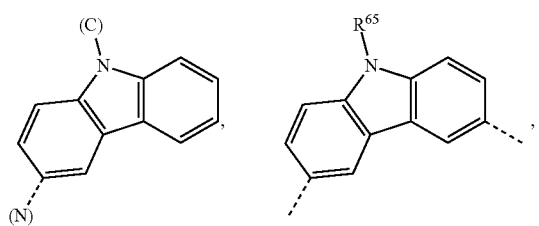
preferably
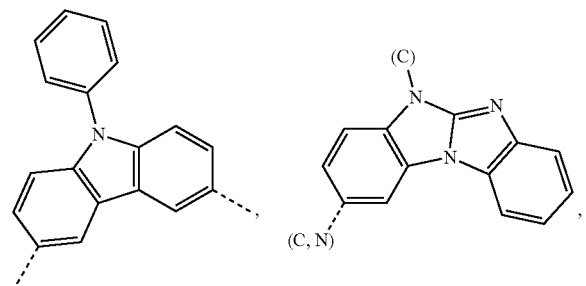
preferably
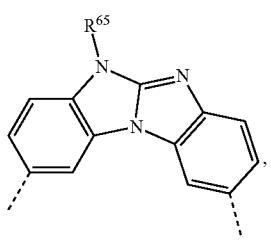
preferably
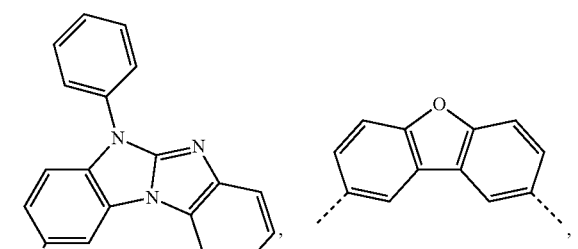
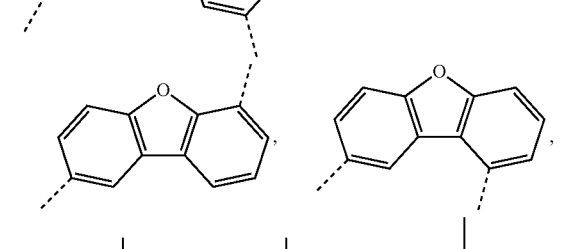
wherein (C)— has the meaning that the bonding site of the group $A^1$, $A^2$, $A^3$ or $A^4$ is linked to a C-atom, and (N)— has the meaning that the bonding site of the group $A^1$, $A^2$, $A^3$ or $A^4$ is linked to a N-atom.
$R^{10}$ is preferably H or a group of the following formula:
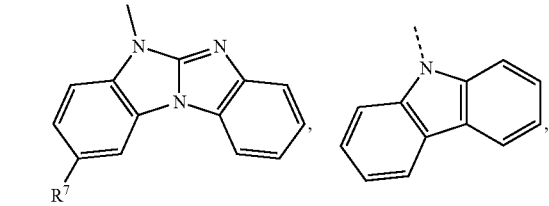
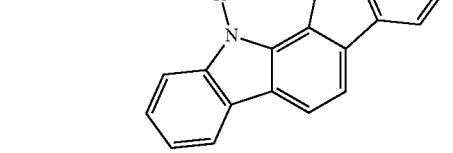
preferably
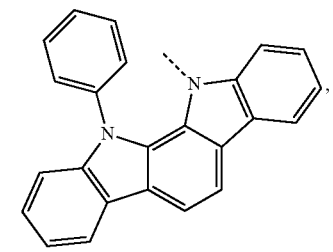
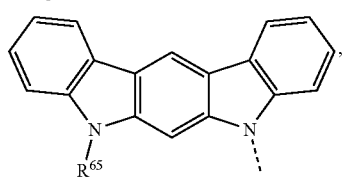
preferably
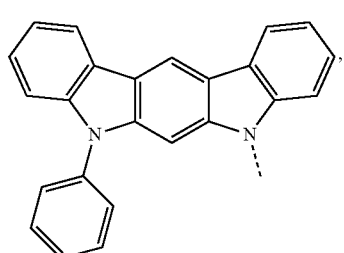
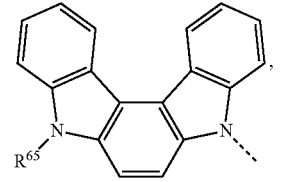

preferably

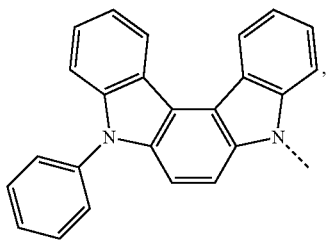

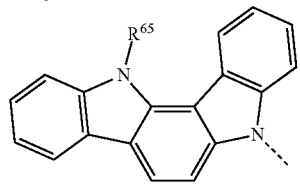

preferably

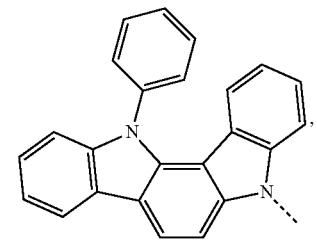

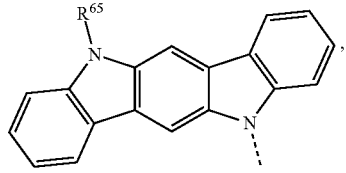

preferably

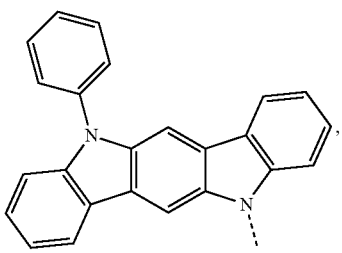

preferably

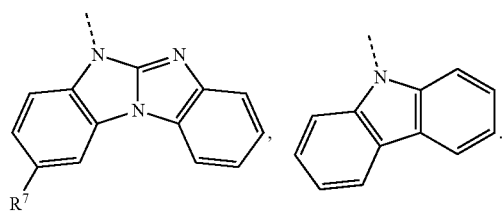

Specific examples of the compounds represented by the formula (I) are given below. The compounds represented by the formula (I) are not limited to the following specific examples.

Among the compounds of formula (I), more preferred compounds are:

Compounds of formula

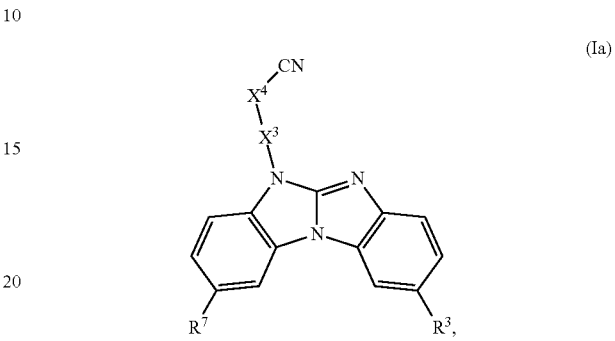

(Ia)

wherein $R^3$, $R^7$, $X^3$ and $X^4$ are defined above and below.

Compounds of formula

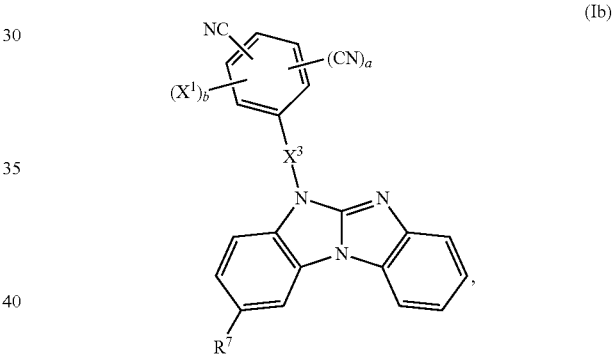

(Ib)

wherein $R^7$, $X^3$, $X^1$, a and b are defined above and below.

Compounds of formula

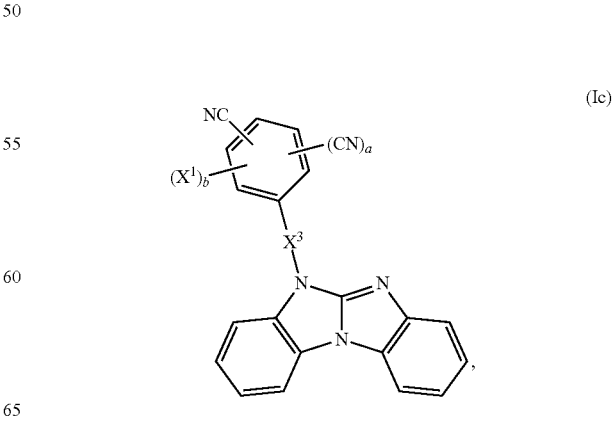

(Ic)

wherein $X^3$, $X^1$, a and b are defined above and below.

Compounds of formula

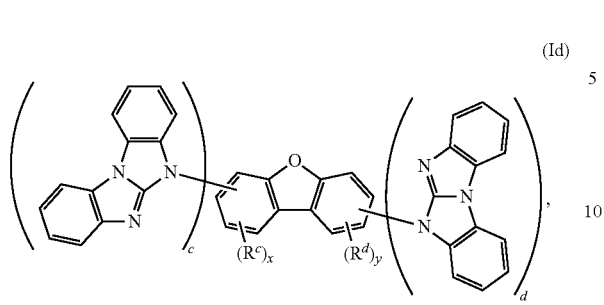

wherein c and d are 0 or 1, and the sum of c+d is 1 or 2;
$R^c$ and $R^d$ are CN;
and x and y are 0 or 1, and the sum of x+y is 1 or 2,
preferably, c is 1 and d is 0 and x is 0 and y is 1.
Preferably, in the compounds of formula (Ia):
$R^3$, $R^7$ are independently of each other H or a group of the following formula:

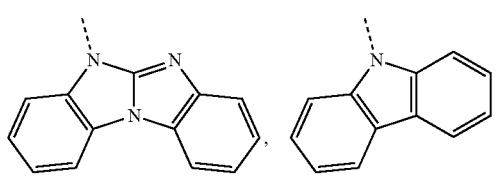

or —$SiR^{70}R^{71}R^{72}$,
$R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and
$R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl; preferably, $R^{70}$, $R^{71}$ and $R^{72}$ are phenyl.
Preferably, in the compounds of formula (Ia):
$X^3$ is a single bond or a group of the following formula

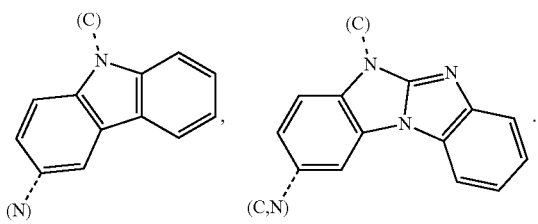

Preferably, in the compounds of formula (Ia):
$X^4$ is a single bond or

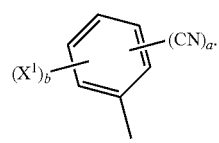

In the compounds of formula (Ib), the residues and indices preferably have the following meaning:
a is 0 or 1 and is b 0 or 1, whereby the sum of a and b is at least 1;

$X^1$ is preferably a group of the following formula:

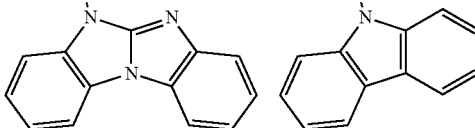

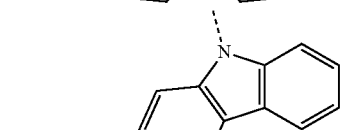

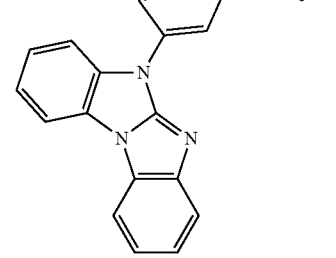

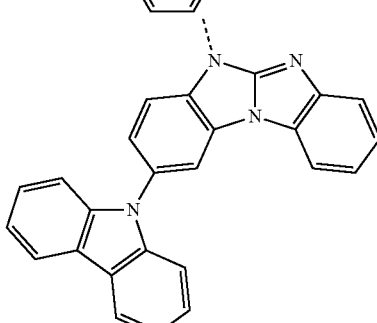

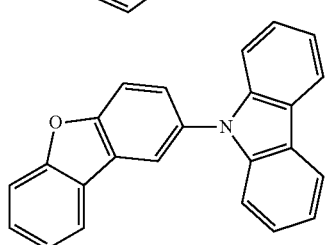

$X^3$ is a single bond or a group of the following formula:

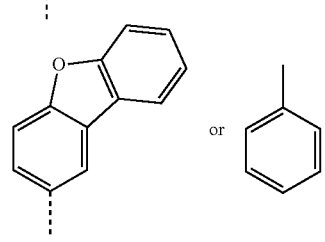

and $R^7$ is H or group of the following formula:

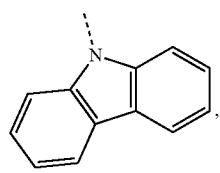

or —$SiR^{70}R^{71}R^{72}$, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl; preferably, $R^{70}$, $R^{71}$ and $R^{72}$ are phenyl.

More preferably, the compounds of formula (Ib) are compounds of formula (Ib')

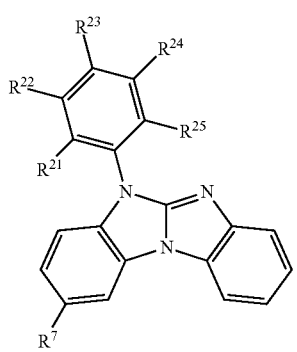

Ib' wherein $R^7$ is defined above and below; and
$R^{21}$, $R^{22}$, $R^{23}$, $R^{24}$ and $R^{25}$
are CN,

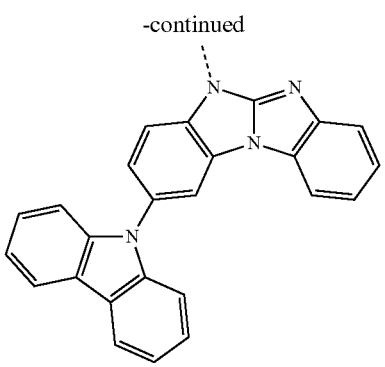

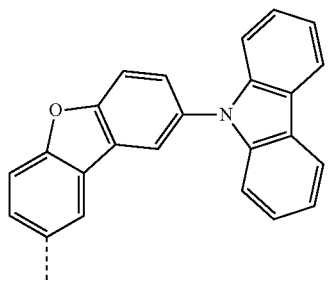

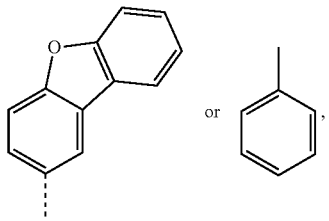

preferably CN,

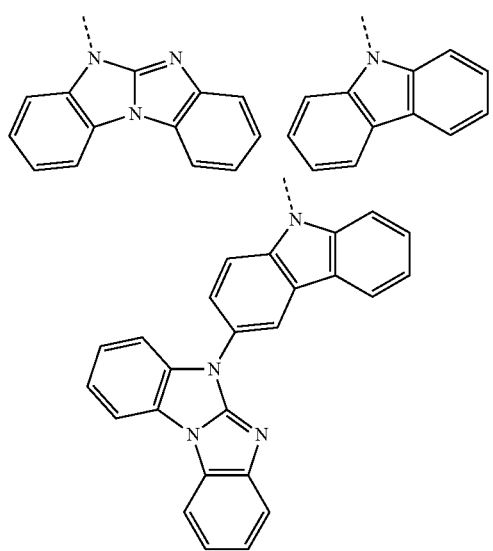

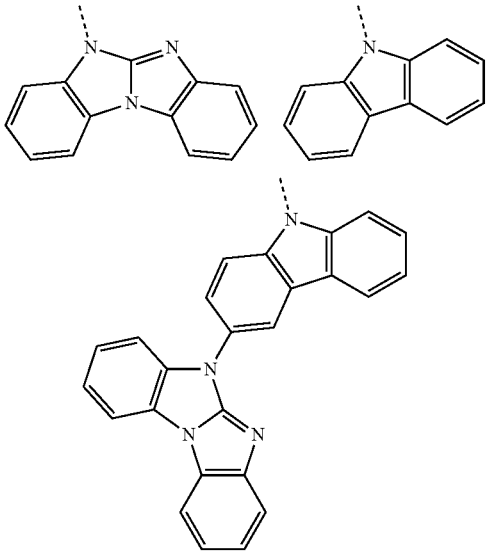

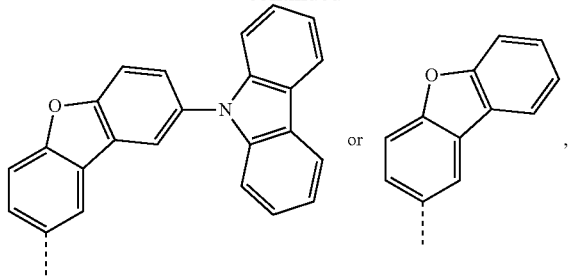 or 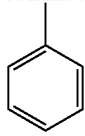, wherein at least one of the residues $R^{21}$, $R^{22}$, $R^{23}$, $R^{24}$ and $R^{25}$ is CN, preferably 1, 2 or 3, more preferably, 1 or 2 of the residues $R^{21}$, $R^{22}$, $R^{23}$, $R^{24}$ and $R^{25}$ are CN.

In the compounds of formula (Ic), the residues and indices preferably have the following meaning:

a is 0 or 1 and is b 0 or 1, whereby the sum of a and b is at least 1;

$X^1$ is preferably a group of the following formula:

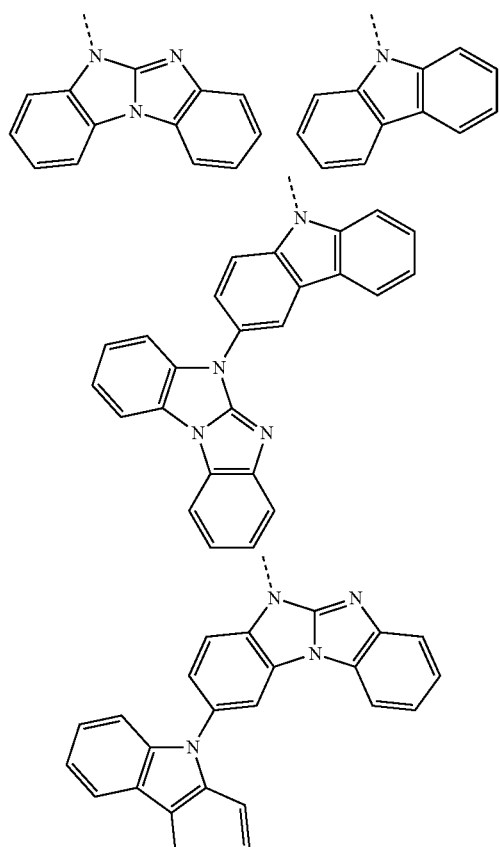

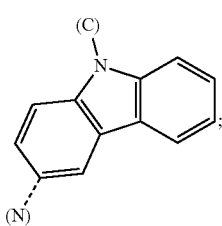

$X^3$ is a single bond or a group of the following formula:

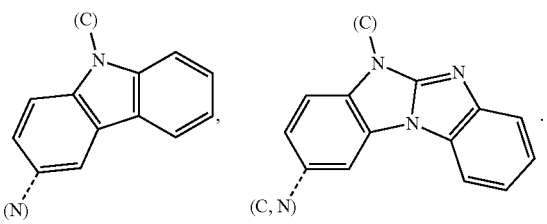

More preferably, the compounds of formula (Ic) have the compound of formula (Ic')

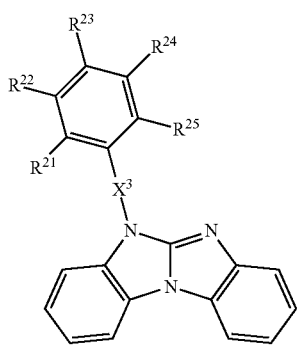

(Ic')

wherein $X^3$ is a single bond or a group of the following formula:

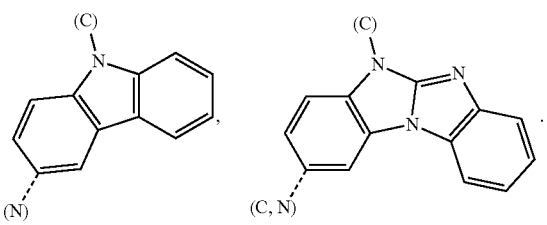

preferably, $X^3$ is

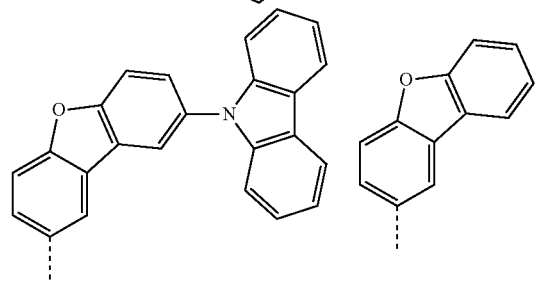

and

R²¹, R²², R²³, R²⁴ and R²⁵ are CN,

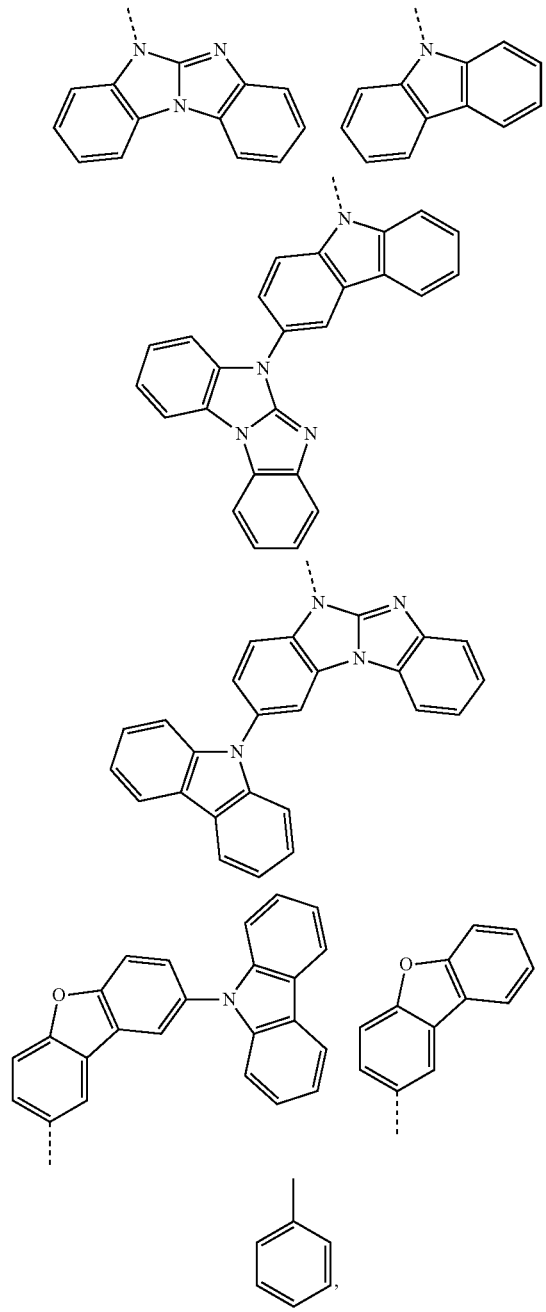

preferably CN,

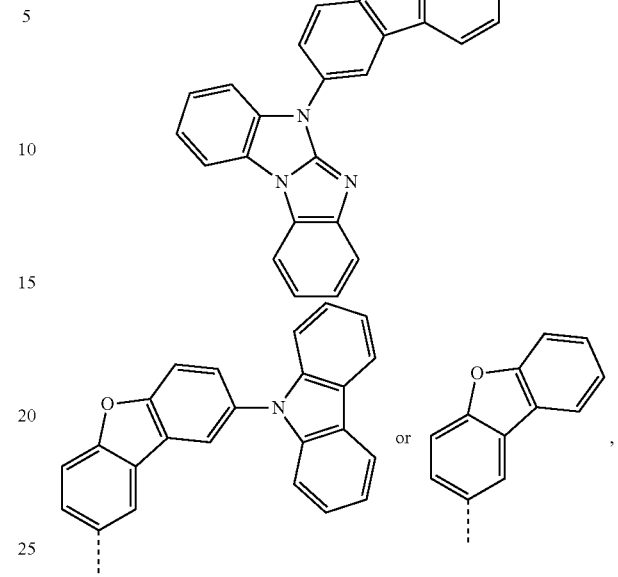

wherein at least one of the residues R²¹, R²², R²³, R²⁴ and R²⁵ is CN, preferably 1, 2 or 3, more preferably, 1 or 2 of the residues R²¹, R²², R²³, R²⁴ and R²⁵ are CN.

More preferably, the compounds of formula (Id) have the compound of formula (Id')

(Id')

$$\text{[structure with } R^8, R^7, R^6, R^1, R^2, R^3 \text{]}$$

wherein
R¹, R⁷ or R⁸ are H,

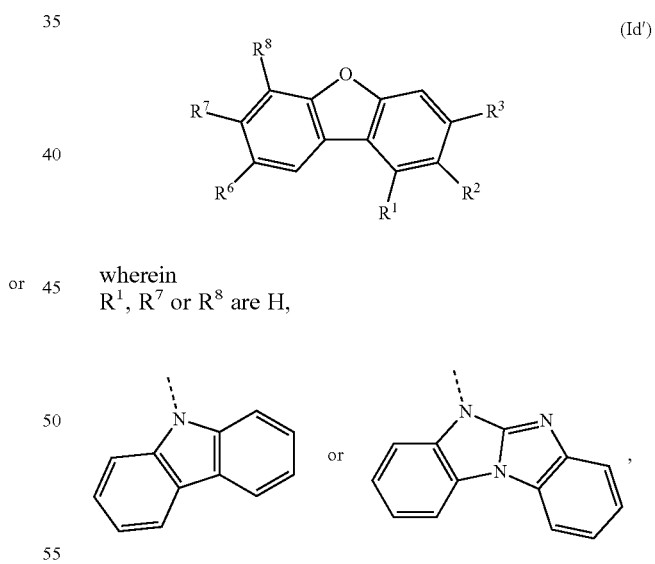

wherein at least one of R¹, R⁷ or R⁸ is

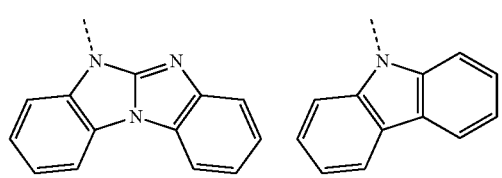 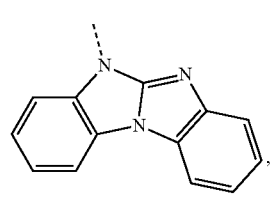

and R², R³ or R⁶ are H or CN, wherein at least one of R², R³ or R⁶ is CN.

Preferred compounds of formulae (Ib'), (Ic') and (Id') are mentioned in the following tables:

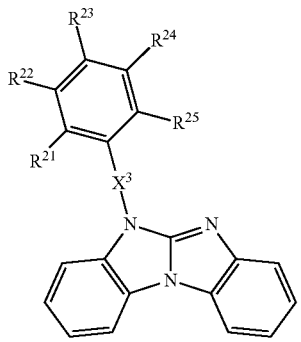
(Ic')

| Nr. | R21 | R22 | R23 | R24 | R25 | X³ |
|---|---|---|---|---|---|---|
| | CN | CN | H | H | H | — |
| | CN | H | CN | H | H | — |
| | CN | H | H | CN | H | — |
| | CN | H | H | H | CN | — |
| | H | CN | CN | H | H | — |
| | H | CN | H | CN | H | — |
| | H | CN | H | H | CN | — |
| | CN | CN | H | H | H | Sp1 |
| | CN | H | CN | H | H | Sp1 |
| | CN | H | H | CN | H | Sp1 |
| | CN | H | H | H | CN | Sp1 |
| | H | CN | CN | H | H | Sp1 |
| | H | CN | H | CN | H | Sp1 |
| | H | CN | H | H | CN | Sp1 |
| | CN | Ar1 | H | H | H | — |
| | CN | H | Ar1 | H | H | — |
| | CN | H | H | Ar1 | H | — |
| | CN | H | H | H | Ar1 | — |
| | CN | Ar2 | H | H | H | — |
| | CN | H | Ar2 | H | H | — |
| | CN | H | H | Ar2 | H | — |
| | CN | H | H | H | Ar2 | — |
| | CN | Ar3 | H | H | H | — |
| | CN | H | Ar3 | H | H | — |
| | CN | H | H | Ar3 | H | — |
| | CN | H | H | H | Ar3 | — |
| | CN | Ar4 | H | H | H | — |
| | CN | H | Ar4 | H | H | — |
| | CN | H | H | Ar4 | H | — |
| | CN | H | H | H | Ar4 | — |
| | CN | H | H | H | H | — |
| | H | CN | CN | H | Ar1 | — |
| | Ar1 | CN | CN | H | H | — |
| | H | CN | CN | H | Ar3 | Sp1 |
| | Ar3 | CN | CN | H | H | Sp1 |
| | CN | Ar3 | H | H | H | Sp1 |
| | CN | Ar5 | H | H | H | — |
| | CN | H | Ar5 | H | H | — |
| | CN | H | H | Ar5 | H | — |
| | CN | H | H | H | Ar5 | — |

Ar1:
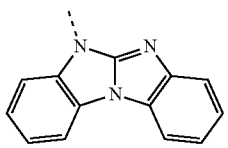

-continued

| Nr. | R21 | R22 | R23 | R24 | R25 | X³ |
|---|---|---|---|---|---|---|

Ar2: 

Ar3: 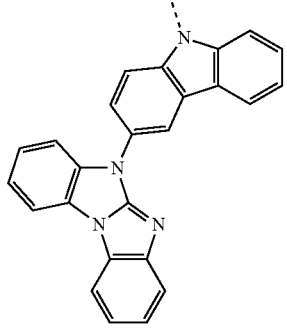

Ar4: 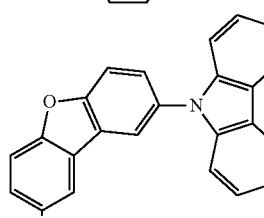

Ar5: 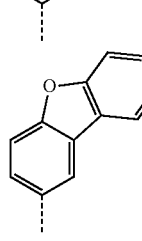

Sp1: 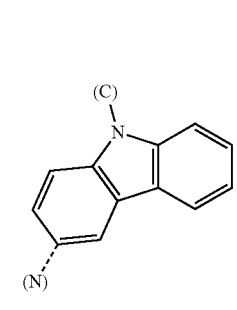

(Ib')

| Nr. | R²¹ | R²² | R²³ | R²⁴ | R²⁵ | R⁷ |
|---|---|---|---|---|---|---|
|  | CN | CN | H | H | H | Ar2 |
|  | CN | H | CN | H | H | Ar2 |
|  | CN | H | H | CN | H | Ar2 |
|  | CN | H | H | H | CN | Ar2 |
|  | CN | H | H | H | H | Ar2 |
|  | H | CN | CN | H | H | Ar2 |
|  | H | CN | H | CN | H | Ar2 |
|  | H | CN | H | H | CN | Ar2 |
|  | CN | CN | H | H | H | Ar2 |
|  | CN | H | CN | H | H | Ar2 |
|  | CN | H | H | CN | H | Ar2 |
|  | CN | H | H | H | CN | Ar2 |
|  | H | CN | CN | H | H | Ar2 |
|  | H | CN | H | CN | H | Ar2 |
|  | H | CN | H | H | CN | Ar2 |
|  | CN | Ar1 | H | H | H | Ar1 |
|  | CN | H | Ar1 | H | H | Ar1 |
|  | CN | H | H | Ar1 | H | Ar1 |
|  | CN | H | H | H | Ar1 | Ar1 |
|  | CN | Ar2 | H | H | H | Ar2 |
|  | CN | H | Ar2 | H | H | Ar2 |
|  | CN | H | H | Ar2 | H | Ar2 |
|  | CN | H | H | H | Ar2 | Ar2 |
|  | CN | Ar3 | H | H | H | Ar3 |
|  | CN | H | Ar3 | H | H | Ar3 |
|  | CN | H | H | Ar3 | H | Ar3 |
|  | CN | H | H | H | Ar3 | Ar3 |
|  | CN | Ar4 | H | H | H | Ar4 |
|  | CN | H | Ar4 | H | H | Ar4 |
|  | CN | H | H | Ar4 | H | Ar4 |
|  | CN | H | H | H | Ar4 | Ar4 |
|  | H | CN | CN | H | Ar1 | Ar1 |
|  | Ar1 | CN | CN | H | H | Ar1 |
|  | H | CN | CN | H | Ar3 | Ar3 |
|  | Ar3 | CN | CN | H | H | Ar3 |
|  | CN | Ar5 | H | H | H | Ar2 |
|  | CN | H | Ar5 | H | H | Ar2 |
|  | CN | H | H | Ar5 | H | Ar2 |
|  | CN | H | H | H | Ar5 | Ar2 |

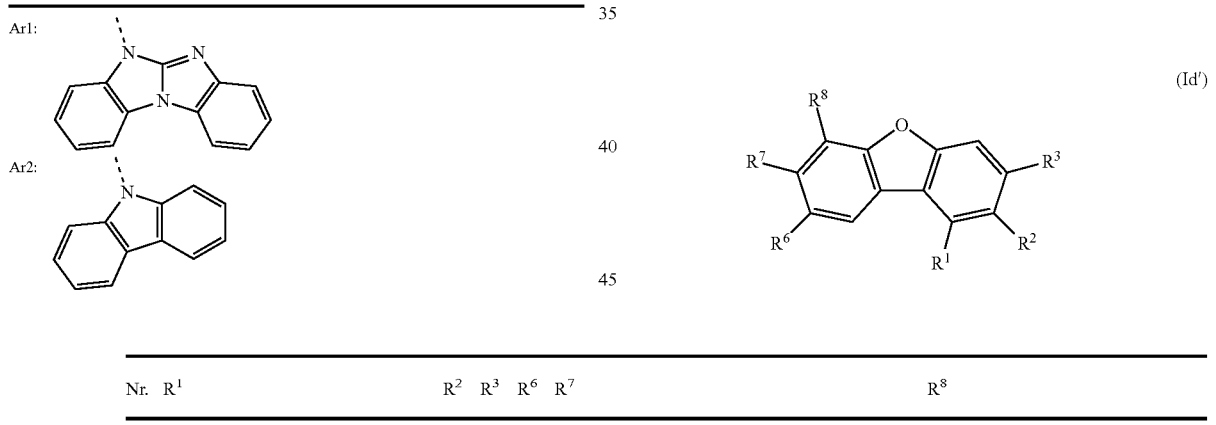

(Id')

| Nr. | R¹ | R² | R³ | R⁶ | R⁷ | R⁸ |
|---|---|---|---|---|---|---|
|  | H | H | CN | H | H | (benzimidazo-benzimidazole) |
|  | (benzimidazo-benzimidazole) | H | CN | H | H | (benzimidazo-benzimidazole) |

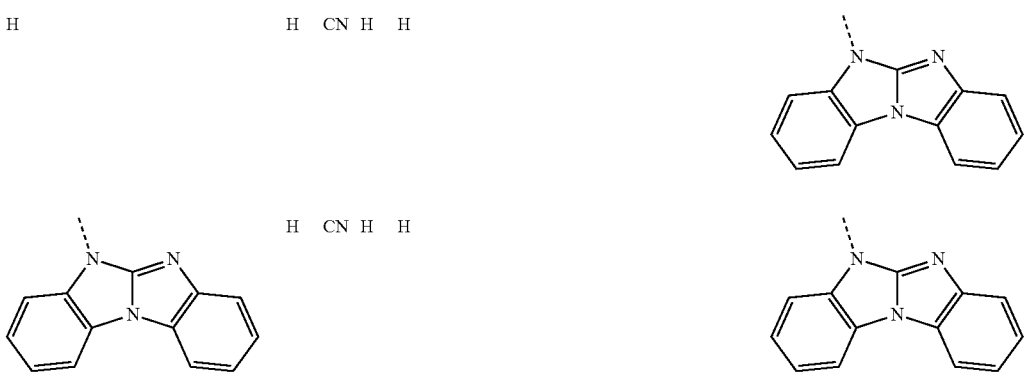

-continued
| Nr. | R¹ | R² | R³ | R⁶ | R⁷ | R⁸ |
|---|---|---|---|---|---|---|
| | 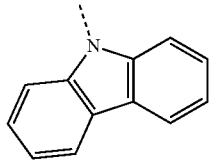 | CN | H | H | H | 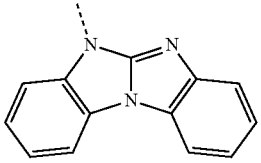 |
| | 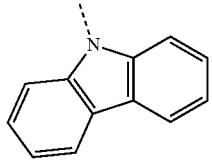 | CN | H | H | 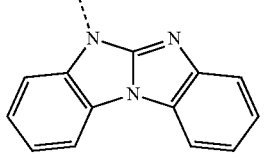 | H |
| | 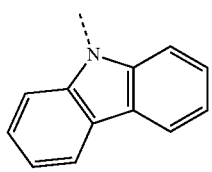 | H | H | CN |  | H |
| | 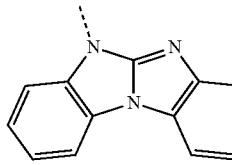 | CN | H | H | 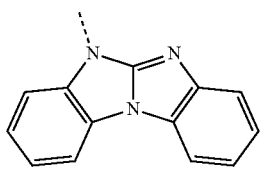 | H |
| | 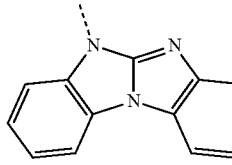 | H | H | CN | 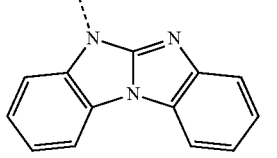 | H |
| | 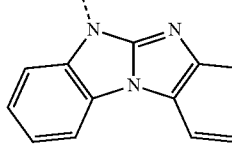 | H | H | CN | 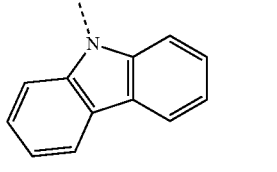 | H |
| | 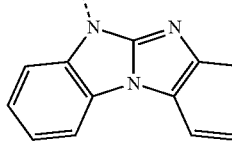 | CN | H | H | 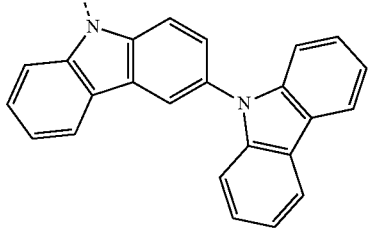 | H |

Further specific examples of formula (I) are the following compounds:
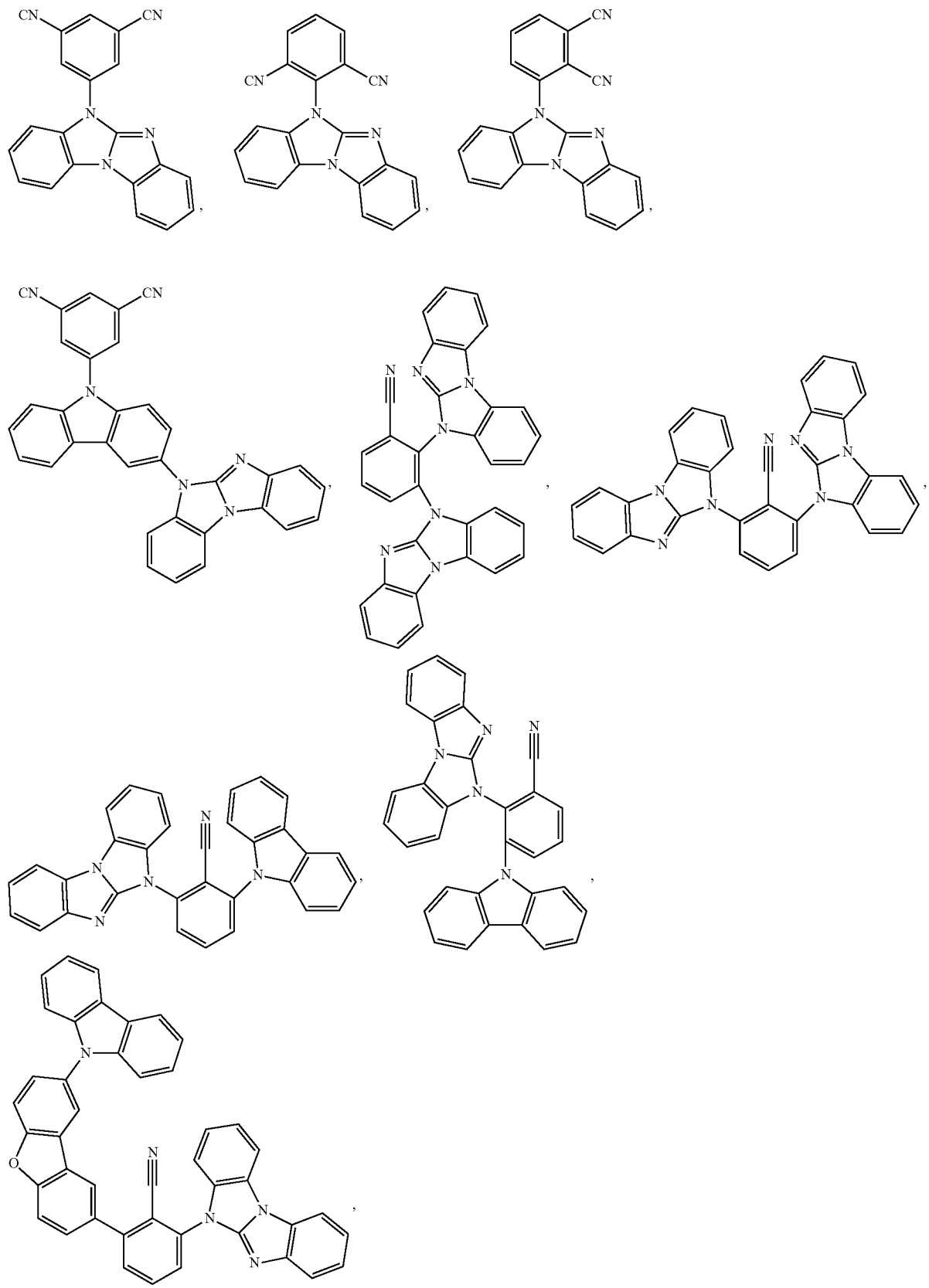

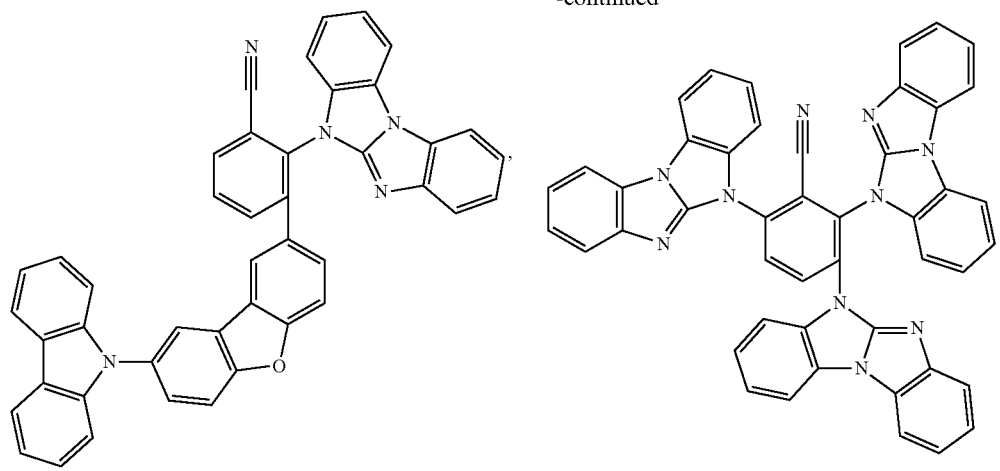
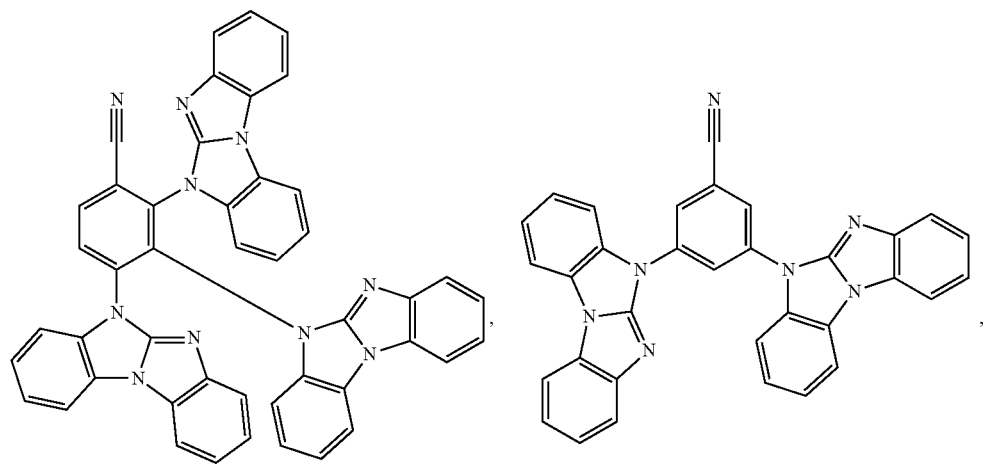
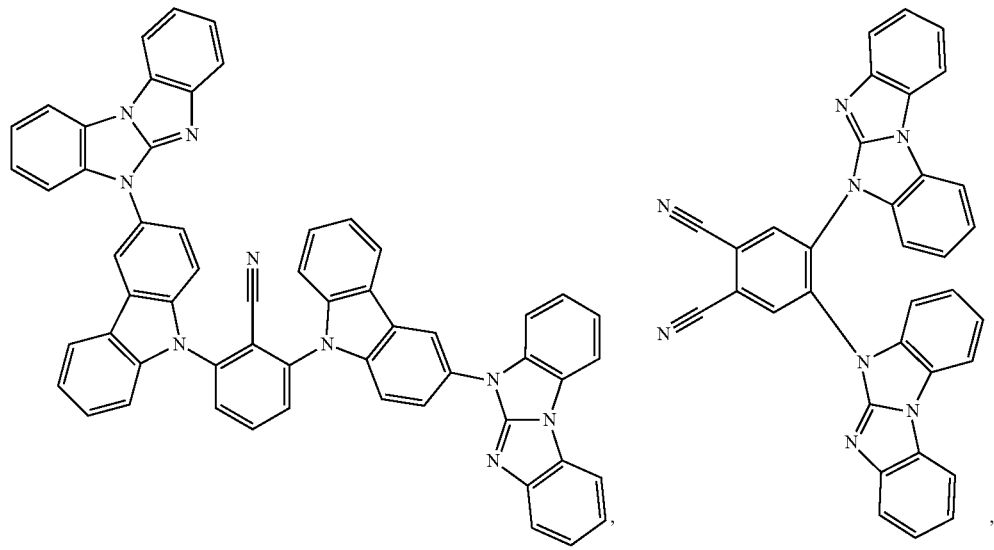

-continued
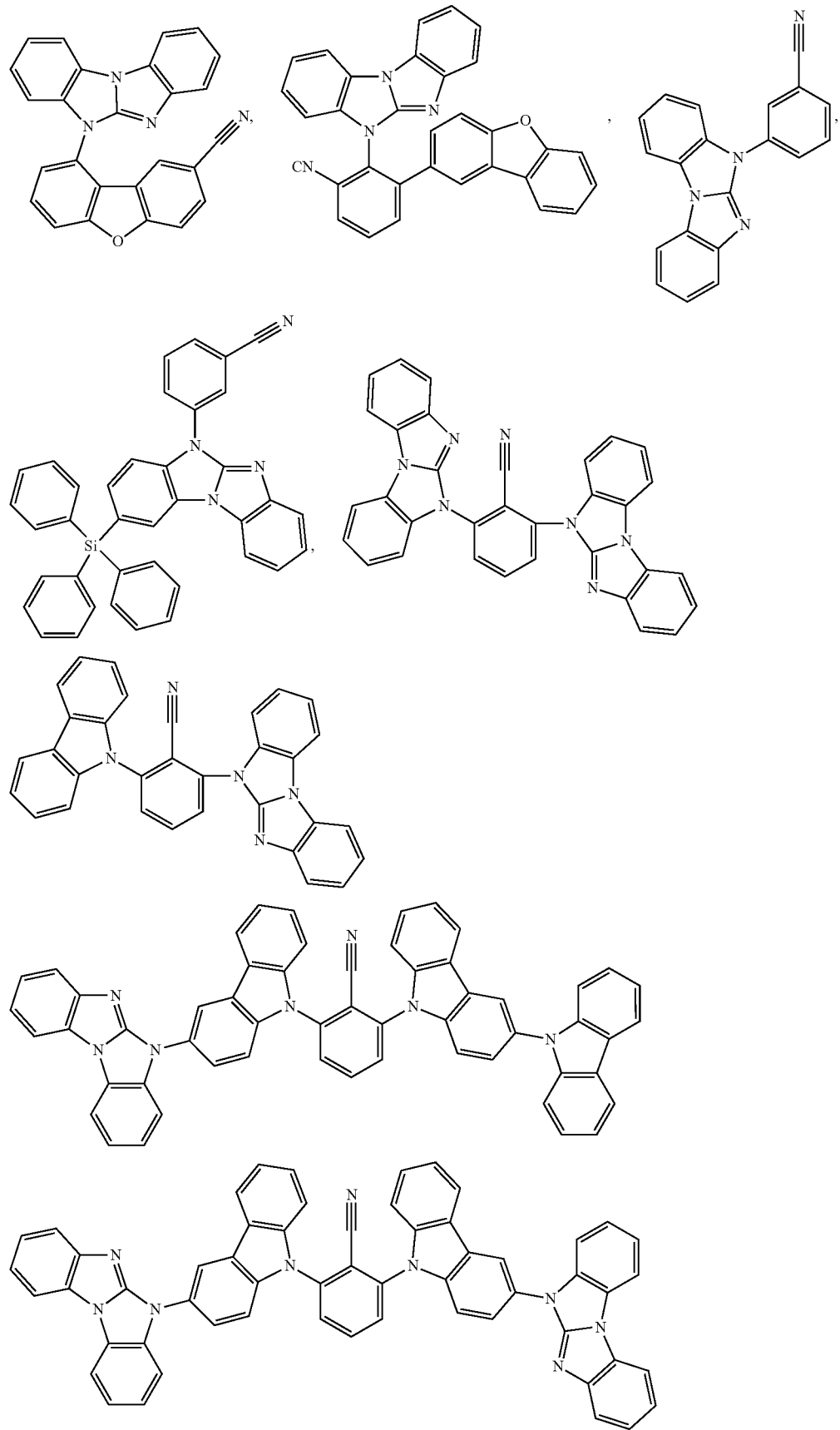

-continued

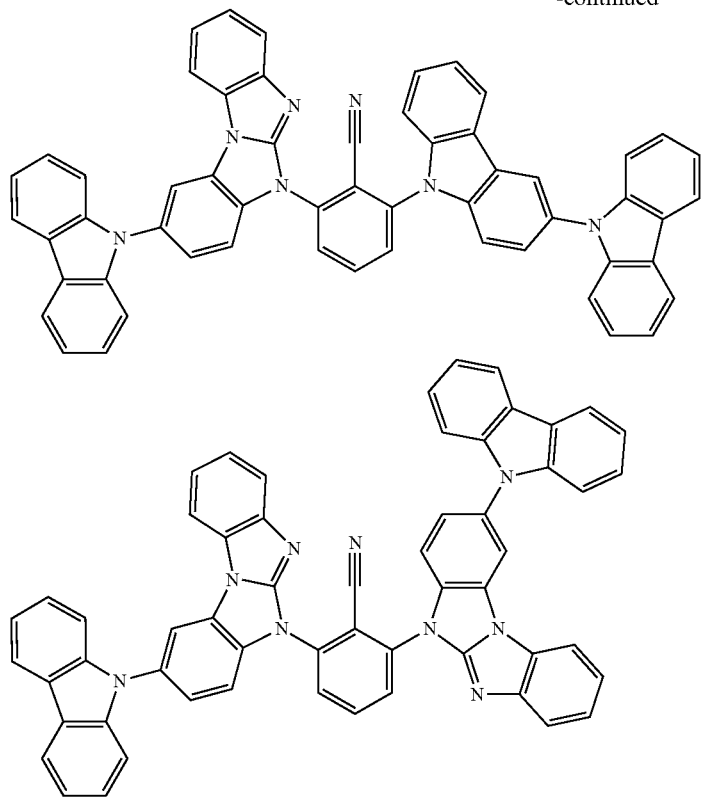

The specific aryl-nitrile or heteroaryl-nitrile benzimidazolo[1,2-a]benzimidazoles derivatives of the present invention are found to be suitable for use in organo-electroluminescent devices. In particular, certain aryl-nitrile or heteroaryl-nitrile benzimidazolo[1,2-a]benzimidazoles derivatives are suitable host materials, especially host materials for phosphorescent emitters, charge transport materials and/or charge/exciton blocker materials with good efficiency and durability.

Also, said aryl-nitrile or heteroaryl-nitrile benzimidazolo [1,2-a]benzimidazoles show low singlet triplet splitting, which makes them useful as TADF (Thermally Activated Delayed Fluorescence, Adv. Mater. 2014, 26, 7931-7958) emitter or TADF host materials in combination with fluorescent emitters. The TADF emitter or TADF host materials can be used together with one or more additional host materials.

The combination of the benzimidazolo[1,2-a]benzimidazole groups with the cyano group in the specific position of the benzimidazolo[1,2-a]benzimidazole gives rise to materials that are highly suitable in devices that emit green, or blue light. Moreover, the improved ambipolar characteristics give rise to more balanced charge transport in devices resulting in lower voltages and higher external quantum efficiencies (EQE's).

One key finding of the inventors of the present invention is the relevance of the position of the nitrile group, which is not directly substituted at the benzimidazolo[1,2-a]benzimidazole skeleton, but substituted at the aromatic or heteroaromatic residue X4. Therefore, the compounds of the present invention are characterized by a high acceptor strength, efficient bipolar characteristics and a good suitability as TADF hosts or emitters.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices (EL devices), such as, for example, organic light-emitting diodes (OLEDs). Preferably, the compounds of the present invention are used in electroluminescent devices, especially in OLEDs.

Accordingly, a further subject of the present invention is directed to an electronic device, comprising a compound according to the present invention. The electronic device is preferably an electroluminescent device (EL-device), especially an OLED.

The compounds of formula I can in principal be used in any layer of an EL device, but are preferably used as host, charge transport and/or charge/exciton blocking material. Particularly, the compounds of formula I are used as host material for green, especially blue light emitting emitters, which are preferably phosphorescent emitters.

Hence, a further subject of the present invention is directed to a charge transport layer comprising a compound of formula I according to the present invention.

A further subject of the present invention is directed to an emitting layer, comprising a compound of formula I according to the present invention. In said embodiment a compound of formula I is preferably used as host material in combination with an emitter, which is preferably a phosphorescent emitter.

A further subject of the present invention is directed to a charge/exciton blocking layer, comprising a compound of formula I according to the present invention.

Synthesis of the Compounds of Formula (I)
Base Skeleton

The synthesis of the compounds of formula (I) can be carried out in analogy to the synthesis of benzimidazolo[1,2-a]benzimidazoles mentioned in the prior art.

The synthesis of

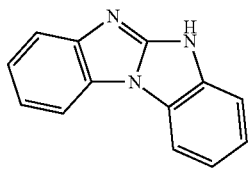 [SMILES: c1ccc2c(c1)nc1[nH]c3ccccc3n12]

is described, for example, in Achour, Reddouane; Zniber, Rachid, Bulletin des Societes Chimiques Belges 96 (1987) 787-92.

N-Arylation

The introduction of the group —$X^3$—$X^4$—CN (N-arylation) is generally carried out by reacting the base skeleton

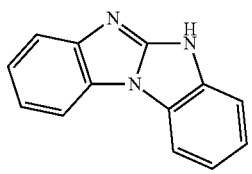 [SMILES: c1ccc2c(c1)nc1[nH]c3ccccc3n12]

with a group Hal-$X^3$—$X^4$—CN, wherein Hal is F, Cl, Br or I, preferably F, Br or I. Suitable groups $X^3$ and $X^4$ are mentioned before.

The nucleophilic aromatic substitution (N-arylation) of

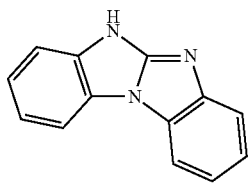 [SMILES: c1ccc2c(c1)nc1[nH]c3ccccc3n12]

with F—$X^3$—$X^4$—CN is generally performed in the presence of a base (Angew. Chem. 2012, 124, 8136-8140, Angew. Chem. Int. Ed. 2008, 47, 8104-8107). Suitable bases are known to those skilled in the art and are preferably selected from the group consisting of alkali metal alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$ or Cs$_2$CO$_3$, alkaline metal phosphates such as K$_3$PO$_4$ alkaline metal fluorides such as KF, CsF and alkali metal alkoxides such as NaOMe, NaOEt. In addition, mixtures of the aforementioned bases are suitable. K$_2$CO$_3$ or Cs$_2$CO$_3$, K$_3$PO$_4$ are preferred.

The nucleophilic aromatic substitution (N-arylation) can be performed in solvent or in a melt. Preferably, the reaction is carried out in a solvent. Suitable solvents are, for example, (polar) aprotic solvents such as dimethyl sulfoxide (DMSO), dimethylformamide (DMF), N-methyl-2-pyrrolidone (NMP) or dimethylacetamide (DMA).

The reaction temperature is strongly dependent on the reactivity of the aryl fluoride. The reaction (N-arylation) is preferably carried out at a temperature of −10 to 220° C., more preferably 60 to 150° C.

Ullmann reaction (N-arylation) of

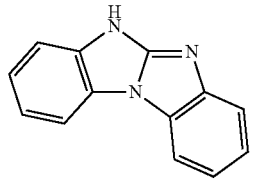 [SMILES: c1ccc2c(c1)nc1[nH]c3ccccc3n12]

with Y—$X^3$—$X^4$—CN (Y is Cl, Br, or I) generally performed in the presence of a base and a catalyst.

Reaction conditions for Ullmann reactions are, for example, described in Angew Chem Int Ed Engl., 48 (2009) 6954-71 WO14009317, WO12130709, J. Am. Chem. Soc. 131 (2009) 2009-2251, J. Org. Chem, 70 (2005) 5165.

Typically the Ullmann coupling of the compound of formula

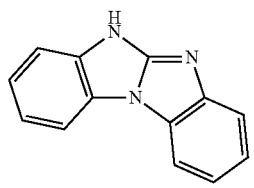 [SMILES: c1ccc2c(c1)nc1[nH]c3ccccc3n12]

with a compound of formula Y—$X^3$—$X^4$—CN (Y is Cl, Br, or I, especially Br, I very especially I) is done in the presence of copper, or a copper salt, such as, for example, CuI, CuBr, Cu$_2$O, or CuO, and a ligand, such as, for example, L-proline, trans-cyclohexane-1,2-diamine (DACH), 1,10-phenanthroline in a solvent, such as, for example, dimethylsulfoxide (DMSO), dimethylformamide (DMF), dimethylacetamide (DMA), N-methylpyrrolidone (NMP) and dioxane, or a solvent mixture. The reaction temperature is dependent on the reactivity of the starting materials, but is generally in the range of 25 to 200° C. If copper salt are used without a ligand the reaction temperatures are higher.

The N-arylation is, for example, disclosed in H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151.

An example for an N-arylation of the

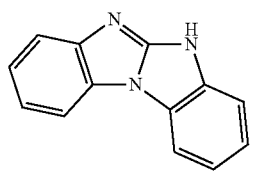 [SMILES: c1ccc2c(c1)nc1[nH]c3ccccc3n12]

skeleton by copper-catalyzed coupling is shown in the following (see also Example 18 in the Example part):

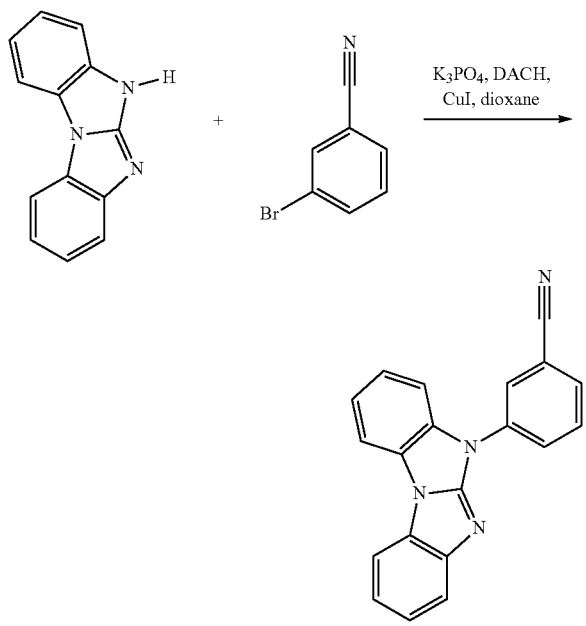 [SMILES: c1ccc2c(c1)nc1[nH]c3ccccc3n12 ; N#Cc1cccc(Br)c1 ; N#Cc1cccc(-n2c3ccccc3n3c4ccccc4nc23)c1]

DACH is (±)-trans-1,2-diaminocyclohexane

Hal-X³—X⁴—CN

The synthesis of

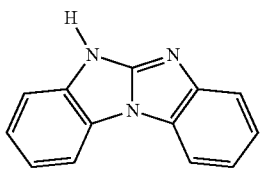 [SMILES: c1ccc2c(c1)nc1[nH]c3ccccc3n12]

is described, for example, in Achour, Reddouane; Zniber, Rachid, Bulletin des Societes Chimiques Belges 96 (1987) 787-92 and WO12130709.

The groups Hal-X³—X⁴—CN are commercially available or prepared by processes known in the art. Suitable preparation processes fore some groups Hal-X³—X⁴—CN are mentioned in the following.

Suitable base skeletons of the formula

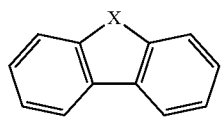

are either commercially available (especially in the cases when X is S, O, NH), or can be obtained by processes known to those skilled in the art. Reference is made to WO2010079051 and EP1885818.

The halogenation of said base skeletons

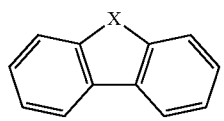

(carbazole, dibenzofuran or dibenzothiophene, which is unsubstituted or substituted) can be performed by methods known to those skilled in the art. Preference is given to brominating or iodinating in the 3 and 6 positions (dibromination, diiodation or mixed bromination/iodation) or in the 3 or 6 positions (monobromination, monoiodation) of the base skeleton in the case of carbazole, respectively in the 2 and 8 positions (dibromination, diiodation) or in the 2 or 8 positions (monobromination, monoiodation) of the base skeleton in the case of dibenzofuran and dibenzothiophene.

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with Br₂ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

For the nucleophilic substitution, Cl- or F-substituted dibenzofurans, dibenzothiophenes and carbazoles are preferred. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

Introduction of the

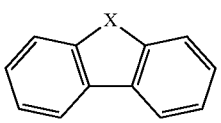

Skeleton

The introduction of the

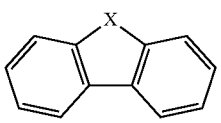

skeleton, can be affected, for example, by copper-catalyzed coupling (Ullmann reaction). Suitable reaction components and reaction conditions for carrying out the Ullmann reaction are mentioned above.

Examples for a copper catalyzed coupling are (see also Example 7B and 8A in the Example part):

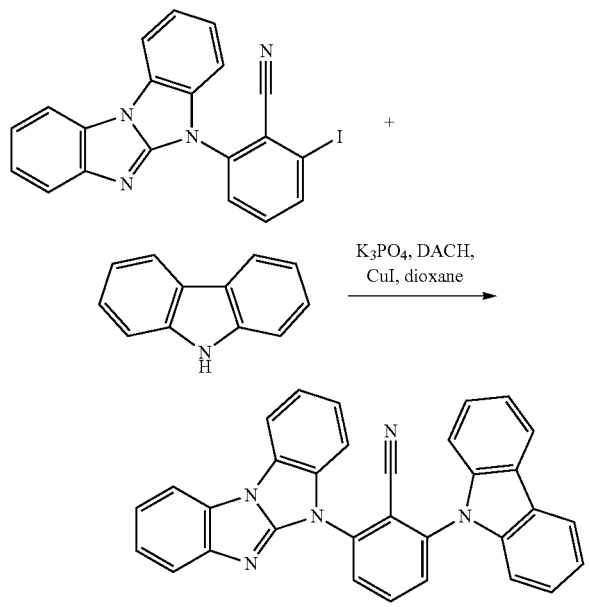

and

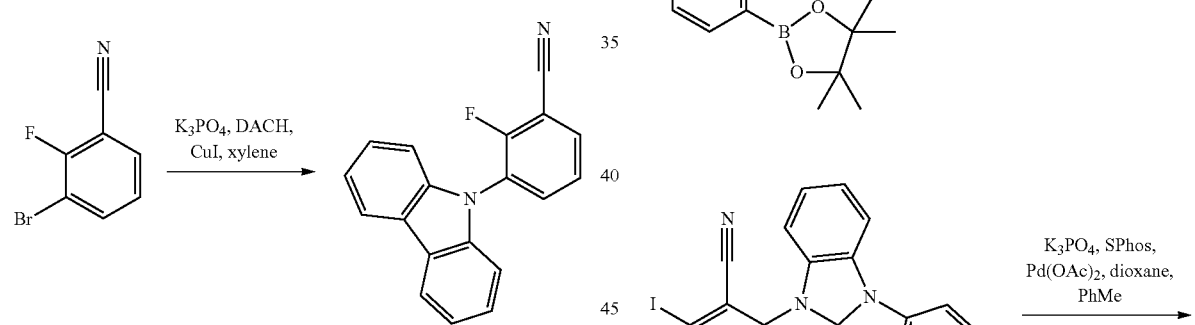

DACH is (±)-trans-1,2-diaminocyclohexane

Alternatively, the introduction of the

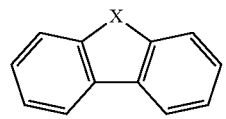

skeleton, especially in cases, wherein the

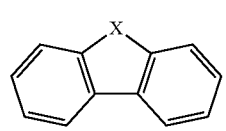

skeleton is substituted, e.g. by a group

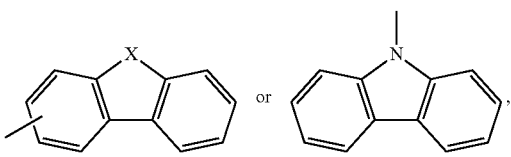

can be affected, for example, by Pd catalyzed coupling of diboronic acid or diboronate group containing dibenzofurans, dibenzothiophenes or carbazoles with halogenated aromatic groups, wherein the halogen is preferably I (Suzuki coupling).

Examples for a Pd catalyzed coupling are (see also Examples 9B and 10B in the Example part):

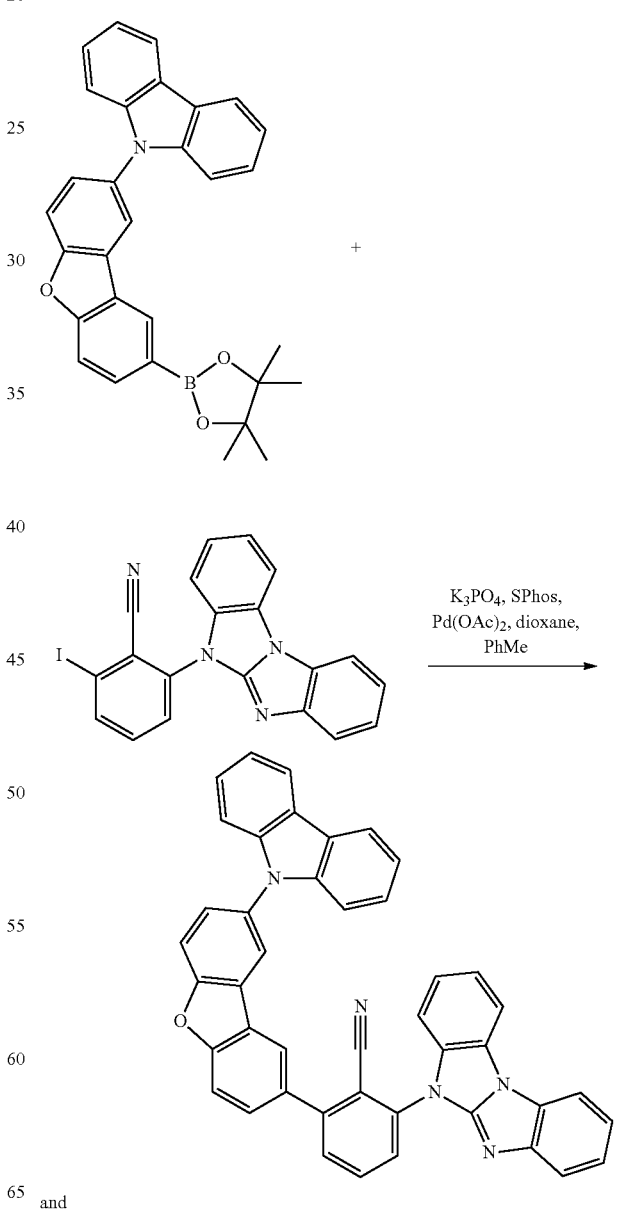

and

-continued

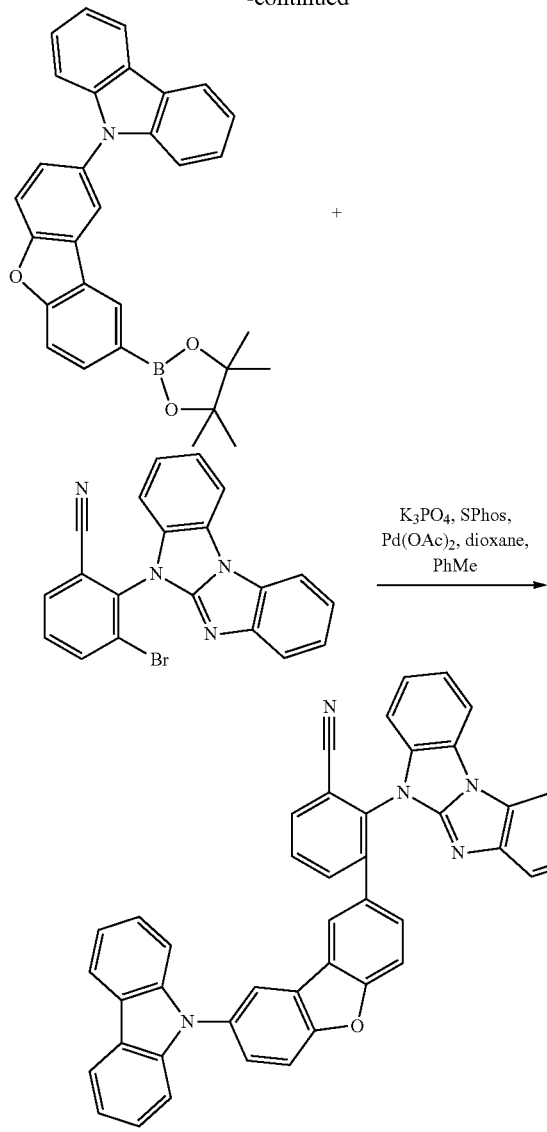

Diboronic acid or diboronate group containing dibenzofurans, dibenzothiophenes and carbazoles can be readily prepared by an increasing number of routes. An overview of the synthetic routes is, for example, given in Angew. Chem. Int Ed. 48 (2009) 9240-9261.

By one common route diboronic acid or diboronate group containing dibenzofurans, dibenzothiophenes, and carbazoles can be obtained by reacting halogenated dibenzofurans dibenzothiophenes and carbazoles with $(Y^1O)_2B$—B$(OY^1)_2$,

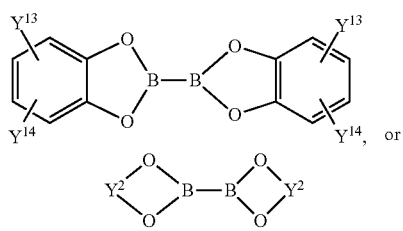

in the presence of a catalyst, such as, for example, [1,1'-bis(diphenylphosphino)ferrocene]dichloropalladium(II), complex (Pd(Cl)$_2$(dppf)), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204), wherein $Y^1$ is independently in each occurrence a $C_1$-$C_{18}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkyl group, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and $Y^{13}$ and $Y^{14}$ are independently of each other hydrogen, or a $C_1$-$C_{18}$alkyl group.

Diboronic acid or diboronate group containing dibenzofurans, dibenzothiophenes and carbazoles can also be prepared by reacting halogenated dibenzofurans, dibenzothiophenes and carbazoles with alkyl lithium reagents, such as, for example, n-butyl lithium, or t-buthyl lithium, followed by reaction with boronic esters, such as, for example, B(isopropoxy)$_3$, B(methoxy)$_3$, or

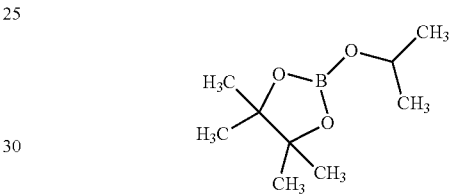

(cf. Synthesis (2000) 442-446).

Diboronic acid or diboronate group containing dibenzofurans, dibenzothiophenes and carbazoles can also be prepared by reacting dibenzofurans, dibenzothiophenes and carbazoles with lithium amides, such as, for example, lithium diisopropylamide (LDA) followed by reaction with boronic esters such as, for example, B(isopropoxy)$_3$, B(methoxy)$_3$, or

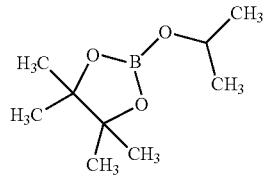

J. Org. Chem. 73 (2008) 2176-2181).

Compounds of Formula I in Organic Electronics Application

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula I.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula I.

The compounds of the formula I being particularly suitable in OLEDs for use as matrix material in a light-emitting layer and/or as electron and/or exciton blocker material and/or as hole and/or exciton blocker material and/or charge transport materials, especially in combination with a phosphorescence emitter.

In the case of use of the inventive compounds of the formula I in OLEDs, OLEDs which have good efficiencies and a long lifetime and which can be operated especially at a low use and operating voltage are obtained. The inventive compounds of the formula I are suitable especially for use as matrix and/or charge/exciton blocker materials for blue and green emitters, for example light blue or deep blue emitters, these being especially phosphorescence emitters. Furthermore, the compounds of the formula I can be used as conductor/complementary materials in organic electronics applications selected from switching elements and organic solar cells.

In the emission layer or one of the emission layers of an OLED, it is also possible to combine an emitter material with at least one matrix material of the compound of the formula I and one or more further matrix materials. This may achieve a high quantum efficiency of this emission layer.

It is likewise possible that the compounds of the formula I are present both in the light-emitting layer (preferably as matrix material) and in the blocking layers (as charge/exciton blockers).

When a compound of the formula I is used as matrix (host) material in an emission layer and additionally as charge/exciton blocker material, owing to the chemical identity or similarity of the materials, an improved interface between the emission layer and the adjacent charge/exciton blocker material, which can lead to a decrease in the voltage with equal luminance and to an extension of the lifetime of the OLED. Moreover, the use of the same material for charge/exciton blocker material and for the matrix of an emission layer allows the production process of an OLED to be simplified, since the same source can be used for the vapor deposition process of the material of one of the compounds of the formula I.

Also, the compounds of the formula I show low singlet triplet splitting, which makes them useful as TADF (Thermally Activated Delayed Fluorescence, Adv. Mater. 2014, 26, 7931-7958) emitter or TADF host materials in combination with fluorescent emitters. Therefore, the compounds of the formula I being particularly suitable in OLEDs for use as TADF emitters or TADF host materials together with a fluorescent emitter. The TADF emitters or TADF host materials is preferably used together with one or more additional host materials.

Suitable structures of organic electronic diodes are known to those skilled in the art and are specified below.

The present invention further provides an organic light-emitting diode comprising an anode (a) and a cathode (i) and a light-emitting layer (e) arranged between the anode (a) and the cathode (i), and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula I is present in the light-emitting layer (e) and/or in at least one of the further layers. The at least one compound of the formula I is preferably present in the light-emitting layer and/or the charge/exciton blocking layers.

In a preferred embodiment of the present invention, at least one compound of the formula I is used as charge transport material. Examples of preferred compounds of formula I are shown above.

Compounds carrying at least one of the following groups are for example particularly useful hole transport materials:

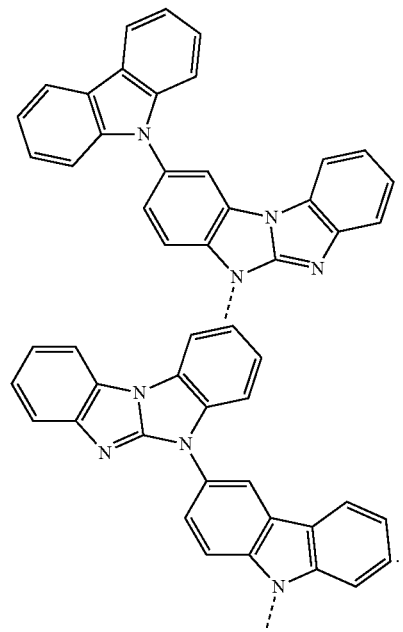

Further preferably, compounds of formula I which are particularly useful hole transport materials comprise one nitrile group.

Compounds carrying more than one nitrile group and one benzimidazolo[1,2-a]benzimidazole group are particularly useful as electron transport materials.

In another preferred embodiment of the present invention, at least one compound of the formula I is used as charge/exciton blocker material.

The present application further relates to a light-emitting layer comprising at least one compound of the formula I, preferably as host material. Examples of preferred compounds of formula I are shown above. The following compounds are examples for particularly useful compounds in the light-emitting layer, especially as host material:

Examples for compounds of formula I particularly suitable as host material for phosphorescence emitters, especially for phosphorescence emitters emitting in the blue or green area of the visible electromagnetic spectrum:

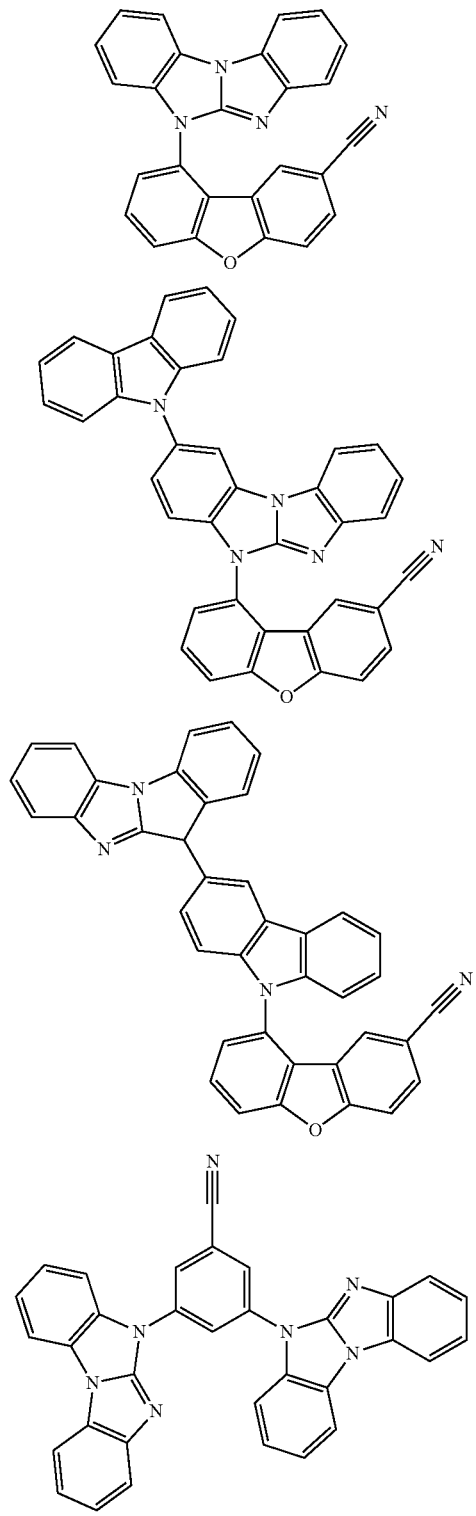

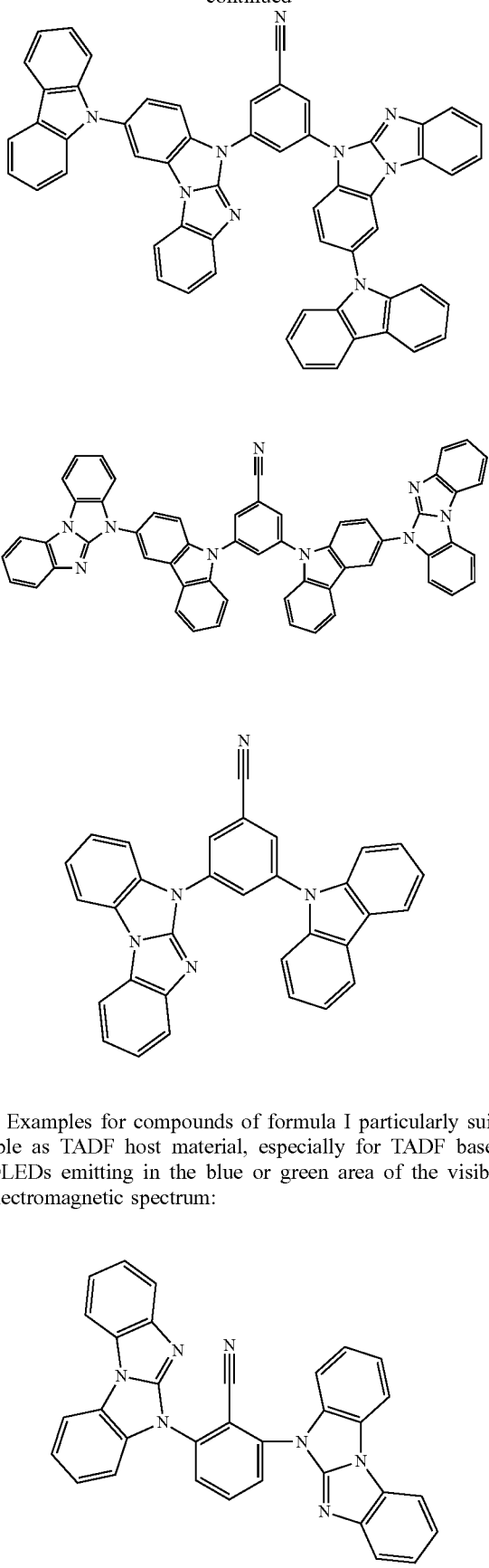

Examples for compounds of formula I particularly suitable as TADF host material, especially for TADF based OLEDs emitting in the blue or green area of the visible electromagnetic spectrum:

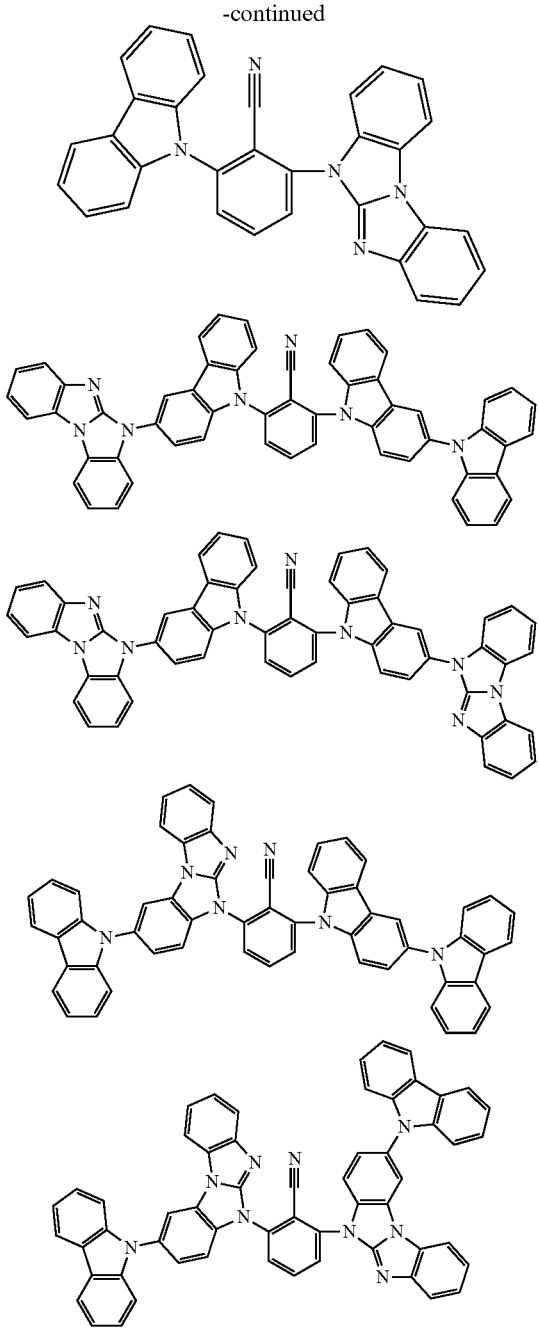

Structure of the Inventive OLED

The inventive organic light-emitting diode (OLED) thus generally has the following structure: an anode (a) and a cathode (i) and a light-emitting layer (e) arranged between the anode (a) and the cathode (i).

The inventive OLED may, for example—in a preferred embodiment—be formed from the following layers:
1. Anode (a)
2. Hole transport layer (c)
3. Light-emitting layer (e)
4. Blocking layer for holes/excitons (f)
5. Electron transport layer (g)
6. Cathode (i)

Layer sequences different than the aforementioned structure are also possible, and are known to those skilled in the art. For example, it is possible that the OLED does not have all of the layers mentioned; for example, an OLED with layers (a) (anode), (e) (light-emitting layer) and (i) (cathode) is likewise suitable, in which case the functions of the layers (c) (hole transport layer) and (f) (blocking layer for holes/excitons) and (g) (electron transport layer) are assumed by the adjacent layers. OLEDs which have layers (a), (c), (e) and (i), or layers (a), (e), (f), (g) and (i), are likewise suitable. In addition, the OLEDs may have a blocking layer for electrons/excitons (d) between the hole transport layer (c) and the Light-emitting layer (e).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used in accordance with the invention.

In a preferred embodiment the OLED according to the present invention comprises in this order:
(a) an anode,
(b) optionally a hole injection layer,
(c) optionally a hole transport layer,
(d) optionally an exciton blocking layer
(e) an emitting layer,
(f) optionally a hole/exciton blocking layer
(g) optionally an electron transport layer,
(h) optionally an electron injection layer, and
(i) a cathode.

In a particularly preferred embodiment the OLED according to the present invention comprises in this order:
(a) an anode,
(b) optionally a hole injection layer,
(c) a hole transport layer,
(d) an exciton blocking layer
(e) an emitting layer,
(f) a hole/exciton blocking layer
(g) an electron transport layer, and
(h) optionally an electron injection layer, and
(i) a cathode.

The properties and functions of these various layers, as well as example materials are known from the prior art and are described in more detail below on basis of preferred embodiments.

Anode (a):

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b):

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Hole Transport Layer (c):

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (triarylamines with (di)benzothiophen/(di)benzofuran; Nan-Xing Hu et al. Synth. Met. 111 (2000) 421 (indolocarbazoles), WO2010002850 (substituted phenylamine compounds) and WO2012/16601 (in particular the hole transport materials mentioned on pages 16 and 17 of WO2012/16601). Combination of different hole transport material may be used. Reference is made, for example, to WO2013/022419, wherein

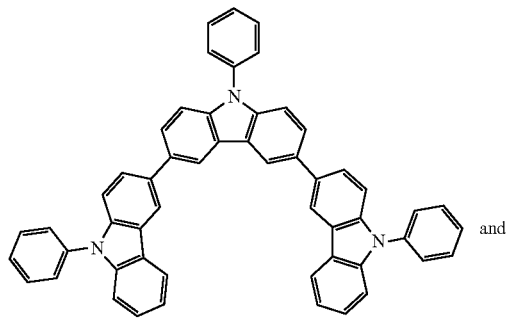

(HTL1-1)

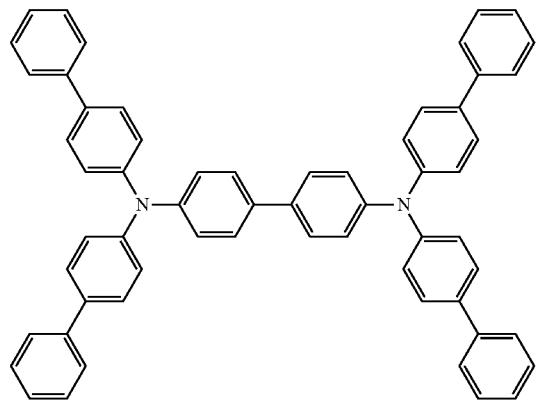 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

(HTL2-1)

constitute the hole transport layer.

Customarily used hole-transporting molecules are selected from the group consisting of

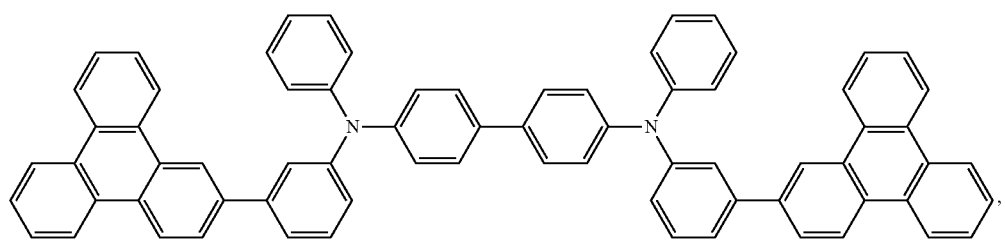

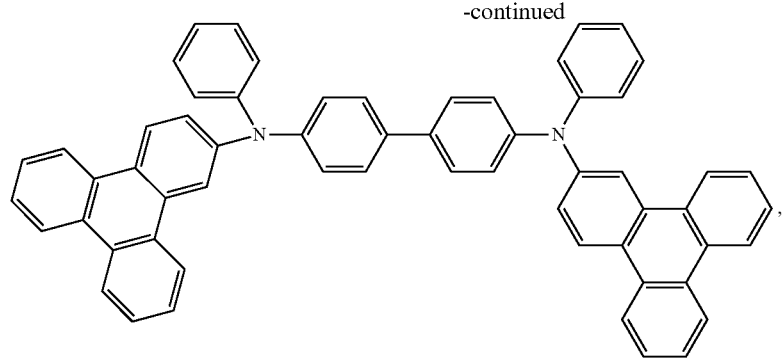
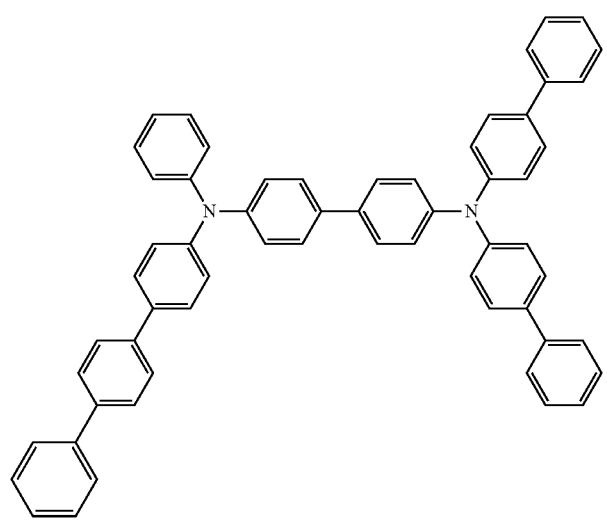
(4-phenyl-N-(4-phenylphenyl)-N-[4-[4-(N-4-(4-phenyl-phenyl)phenyl]anilino)phenyl]phenyl]aniline),
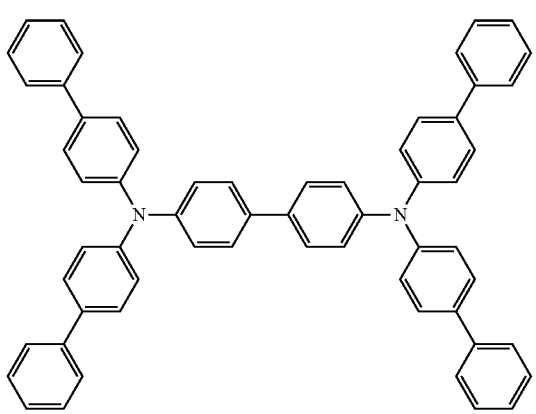
(4-phenyl-N-(4-phenylphenyl)-N-[4-[4-(4-phenyl-N-(4-phenylphenyl)anilino)phenyl]phenyl]aniline),
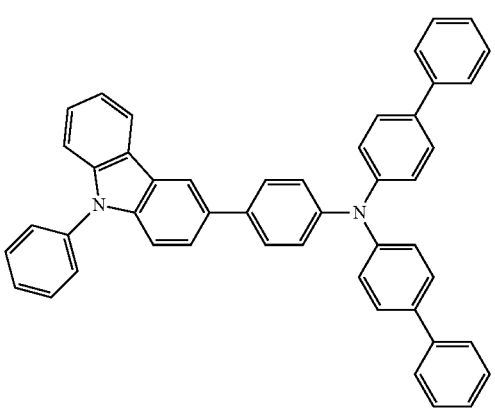 [SMILES: c1ccc(-c2ccc(N(c3ccc(-c4ccccc4)cc3)c3ccc(-c4ccc5c(c4)c4ccccc4n5-c4ccccc4)cc3)cc2)cc1]
(4-phenyl-N-[4-(9-phenylcarbazol-3-yl)phenyl]-N-(4-phe-nylphenyl)aniline),

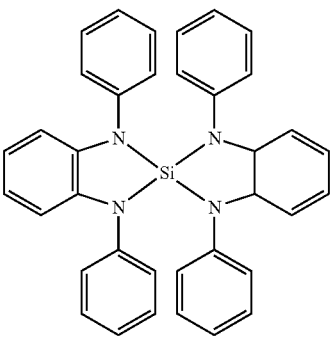 [SMILES: C1=CC2C(C=C1)N(c1ccccc1)[Si]1(N(c3ccccc3)c3ccccc3N1c1ccccc1)N2c1ccccc1]

(1,1',3,3'-tetraphenylspiro[1,3,2-benzodiazasilole-2,2'-3a,7a-dihydro-1,3,2-benzodiazasilole]),

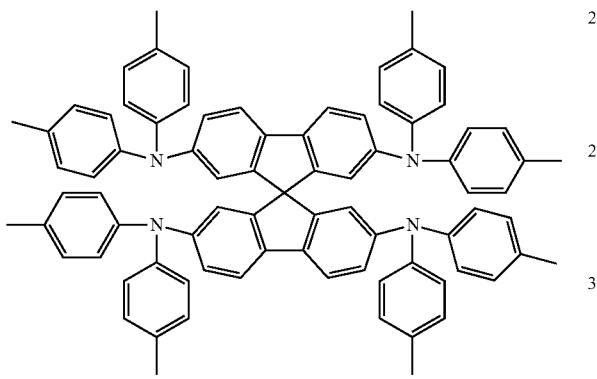

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS. Preferred examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT).

In a preferred embodiment it is possible to use metal carbene complexes as hole transport materials. Suitable carbene complexes are, for example, carbene complexes as described in WO2005/019373A2, WO2006/056418 A2, WO2005/113704, WO2007/115970, WO2007/115981, WO2008/000727 and PCT/EP2014/055520. One example of a suitable carbene complex is Ir(DPBIC)$_3$ with the formula:

(HTM-1)

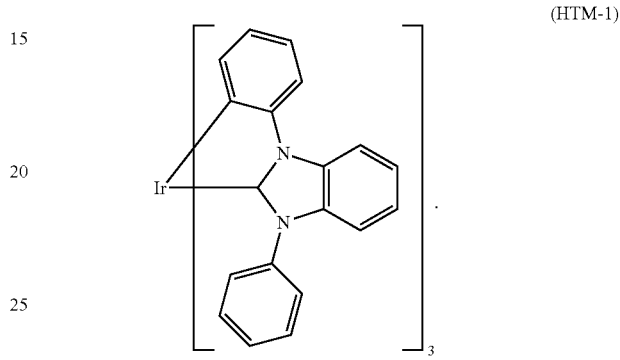

Another example of a suitable carbene complex is Ir(ABIC)$_3$ with the formula:

(HTM-2)

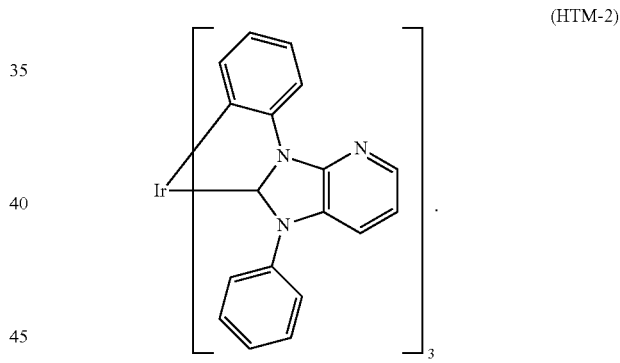

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example MoO$_2$, MoO$_3$, WO$_x$, ReO$_3$ and/or V$_2$O$_5$, preferably MoO$_3$ and/or ReO$_3$, more preferably MoO$_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane (F$_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8tetracyanoquinodimethane, dicyanomethylene-1,3,4,5,7,8-hexafluoro-6Hnaphthalen-2-ylidene)malononitrile (Fe-TNAP), Mo(tfd)$_3$ (from Kahn et al., J. Am. Chem. Soc. 2009, 131 (35), 12530-12531), compounds as described in EP1988587, US2008265216, EP2180029, US20100102709, WO2010132236, EP2180029 and quinone compounds as mentioned in EP2401254.

Preferred mixtures comprise the aforementioned carbene complexes, such as, for example, the carbene complexes HTM-1 and HTM-2, and MoO$_3$ and/or ReO$_3$, especially MoO$_3$. In a particularly preferred embodiment the hole transport layer comprises from 0.1 to 10 wt % of MoO$_3$ and 90 to 99.9 wt % carbene complex, especially of the carbene complex HTM-1 and HTM-2, wherein the total amount of the MoO$_3$ and the carbene complex is 100 wt %.

Exciton Blocking Layer (d):

Blocking layers may be used to reduce the number of charge carriers (electrons or holes) and/or excitons that leave the emissive layer. An electron/exciton blocking layer (d) may be disposed between the first emitting layer (e) and the hole transport layer (c), to block electrons from emitting layer (e) in the direction of hole transport layer (c). Blocking layers may also be used to block excitons from diffusing out of the emissive layer. Suitable metal complexes for use as electron/exciton blocker material are, for example, carbene complexes as described in WO2005/019373A2, WO2006/056418A2, WO2005/113704, WO2007/115970, WO2007/115981, WO2008/000727 and PCT/EP2014/055520. Explicit reference is made here to the disclosure of the WO applications cited, and these disclosures shall be considered to be incorporated into the content of the present application. Examples of suitable carbene complexes are compounds HTM-1 and HTM-2.

Emitting Layer (e)

The light-emitting layer (e) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs, preferably as emitter material, are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A1, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)pyridinato-N,C$^{3'}$)(acetylacetonate), tris(2-phenylquinoline)iridium(III), iridium(III) bis(2-(4,6-difluorophenyl)pyridinato-N,C$^{2}$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldibenzo[f,h]quinoxaline)acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-pyridine)(acetylacetonato) iridium(III).

In addition, the following commercially available materials are suitable: tris(dibenzoylacetonato)mono(phenanthroline)europium(III), tris(dibenzoylmethane)-mono (phenanthroline)europium(III), tris(dibenzoylmethane) mono(5-aminophenanthroline)-europium(III), tris(di-2-naphthoylmethane)mono(phenanthroline)europium(III), tris (4-bromobenzoylmethane)mono(phenanthroline)europium (III), tris(di(biphenyl)methane)-mono(phenanthroline) europium(III), tris(dibenzoylmethane)mono(4,7-diphenylphenanthroline)europium(III), tris(dibenzoylmethane)mono (4,7-di-methyl-phenanthroline)europium(III), tris (dibenzoylmethane)mono(4,7-dimethylphenanthrolinedisulfonic acid)europium(III) disodium salt, tris[di(4-(2-(2-ethoxyethoxy)ethoxy)benzoylmethane)]mono-(phenanthroline)europium(III) and tris[di [4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)-pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Preferred phosphorescence emitters are carbene complexes.

Suitable phosphorescent blue emitters are specified in the following publications: WO2006/056418A2, WO2005/113704, WO2007/115970, WO2007/115981, WO2008/000727, WO2009050281, WO2009050290, WO2011051404, US2011/057559 WO2011/073149, WO2012/121936A2, US2012/0305894A1, WO2012/170571, WO2012/170461, WO2012/170463, WO2006/121811, WO2007/095118, WO2008/156879, WO2008/156879, WO2010/068876, US2011/0057559, WO2011/106344, US2011/0233528, WO2012/048266, WO2012/172482, PCT/EP2014/064054 and PCT/EP2014/066272.

Preferably, the light emitting layer (e) comprises at least one carbene complex as phosphorescence emitter. Suitable carbene complexes are, for example, compounds of the formula

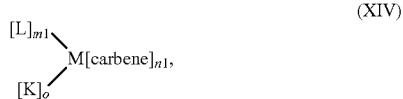

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom; carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand, preferably selected from the group consisting of phosphines; phosphonates and derivatives thereof, arsenates and derivatives thereof; phosphites; CO; pyridines; nitriles and conjugated dienes which form a π complex with $M^1$;

n1 is the number of carbene ligands, where n1 is at least 1 and when n1>1 the carbene ligands in the complex of the formula I can be identical or different;

m1 is the number of ligands L, where m1 can be 0 or ≥1 and when m1>1 the ligands L can be identical or different;

o is the number of ligands K, where o can be 0 or ≥1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

More preferred are metal-carbene complexes of the general formula

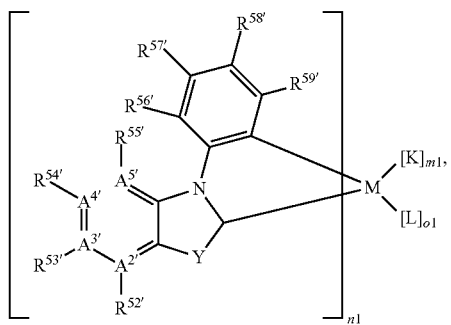

which are described in WO2011/073149, where M is Ir, or Pt, n1 is an integer selected from 1, 2 and 3, Y is $NR^{51'}$, O, S or $C(R^{25'})_2$, $A^{2'}$, $A^{3'}$, $A^{4'}$, and $A^{5'}$ are each independently N or C, where 2 A'=nitrogen atoms and at least one carbon atom is present between two nitrogen atoms in the ring, $R^{51'}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52'}$, $R^{53'}$, $R^{54'}$ and $R^{55'}$ are each, if $A^{2'}$, $A^{3'}$, $A^{4'}$ and/or $A^{5'}$ is N, a free electron pair, or, if $A^{2'}$, $A^{3'}$, $A^{4'}$ and/or $A^{5'}$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53'}$ and $R^{54'}$ together with $A^{3'}$ and $A^{4'}$ form an optionally substituted, unsaturated ring optionally interrupted by at least one further heteroatom and having a total of 5 to 18 carbon atoms and/or heteroatoms, $R^{56'}$, $R^{57'}$, $R^{58'}$ and $R^{59'}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56'}$ and $R_{57'}$, $R^{57'}$ and $R^{58'}$ or $R^{58'}$ and $R^{59'}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^{5'}$ is C, $R^{55'}$ and $R^{56'}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25'}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand,
L is a mono- or dianionic ligand, preferably monoanionic ligand, which may be mono- or bidentate,
m1 is 0, 1 or 2, where, when m1 is 2, the K ligands may be the same or different,
o1 is 0, 1 or 2, where, when o1 is 2, the L ligands may be the same or different
The compound of formula XIV is preferably a compound of the formula:
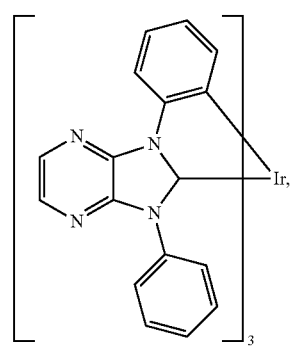
(BE-1)
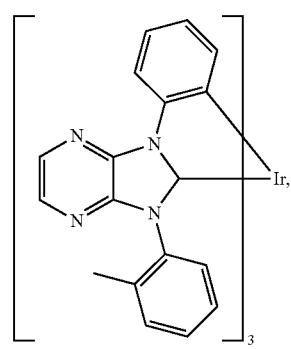
(BE-2)
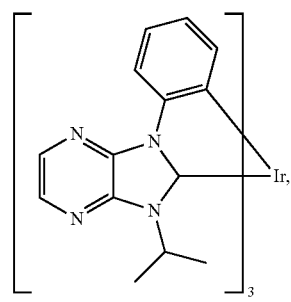
(BE-3)
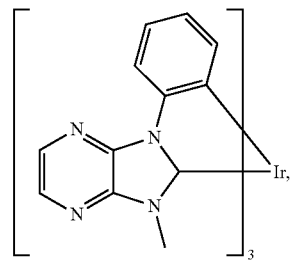
(BE-4)
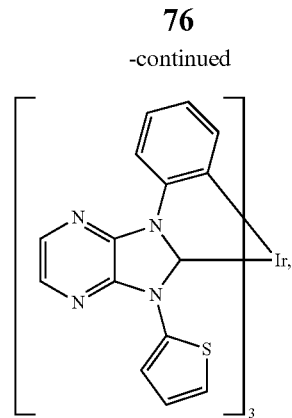
(BE-5)
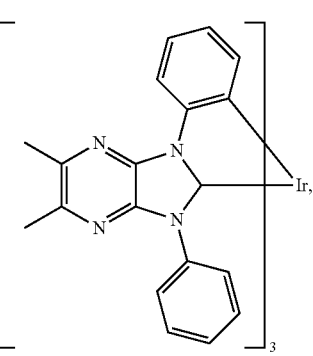
(BE-6)
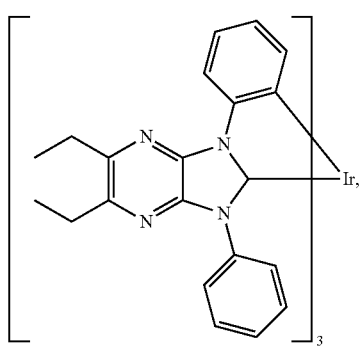
(BE-7)
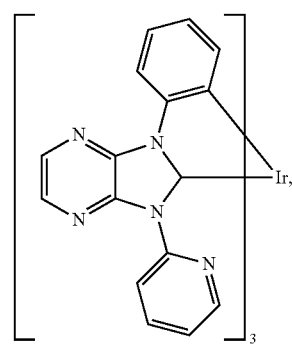
(BE-8)

(BE-9)
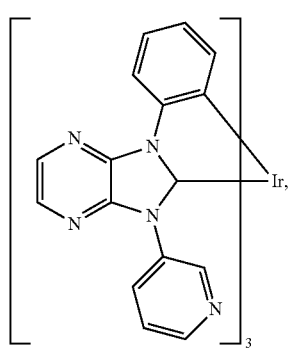
(BE-10)
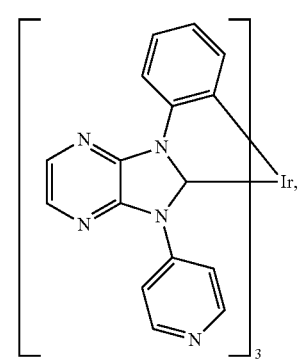
(BE-11)
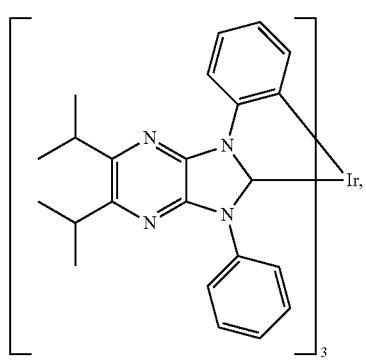
(BE-12)
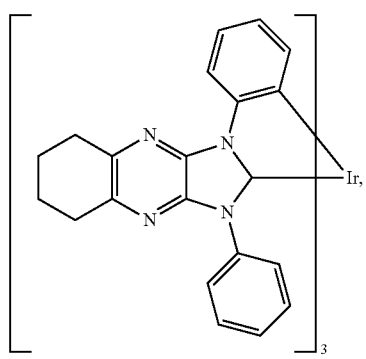
(BE-13)
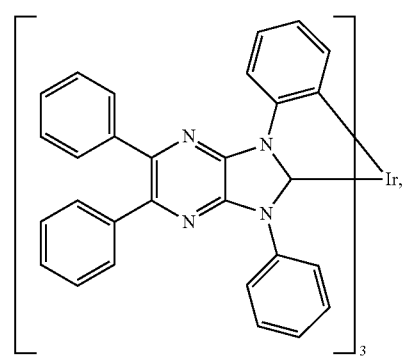
(BE-14)
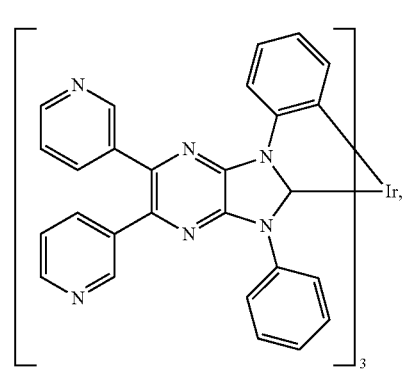
(BE-15)
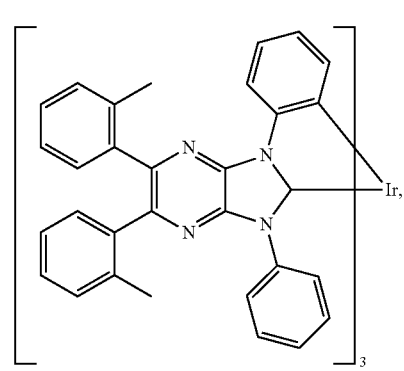
(BE-16)
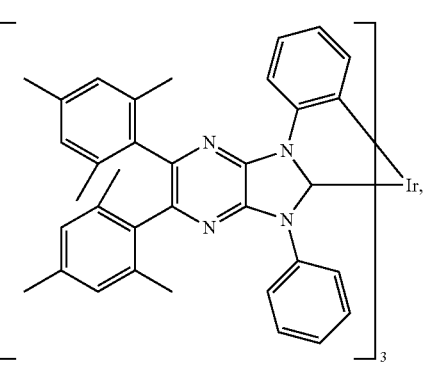

(BE-17)
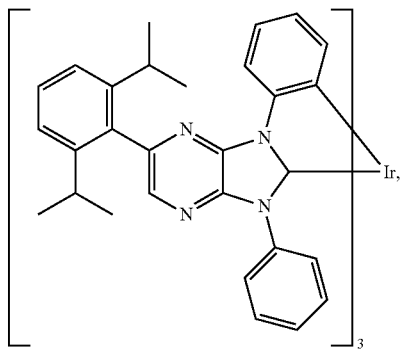
(BE-18)
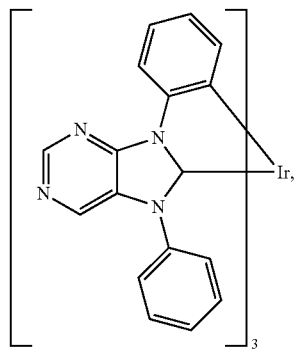
(BE-19)
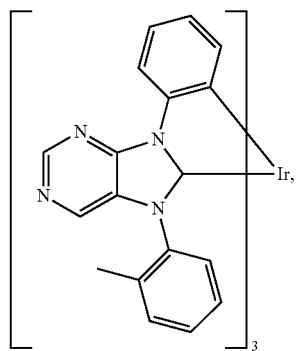
(BE-20)
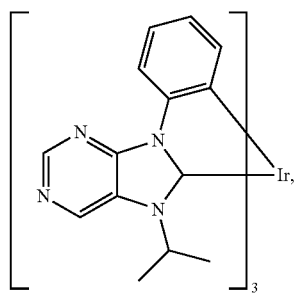
(BE-21)
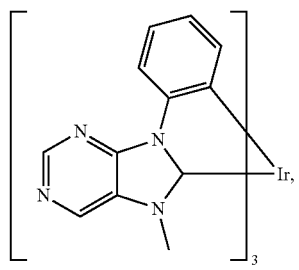
(BE-22)
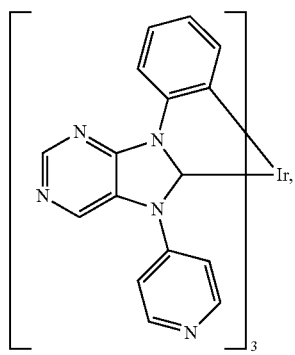
(BE-23)
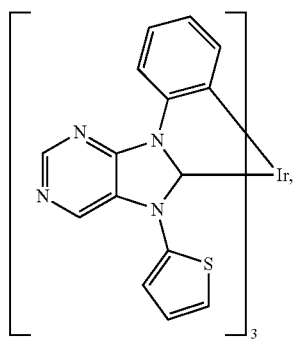
(BE-24)
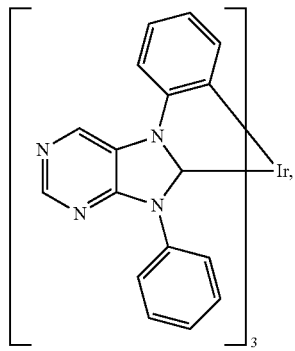
(BE-25)
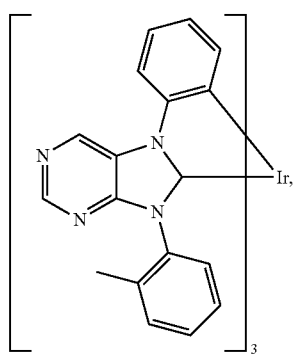

(BE-26)
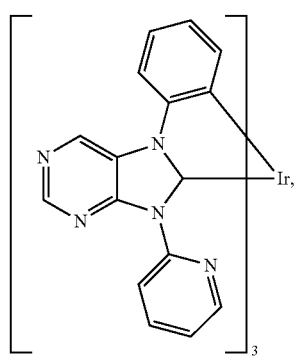
(BE-27)
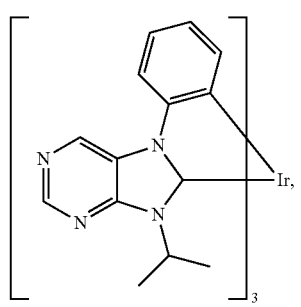
(BE-28)
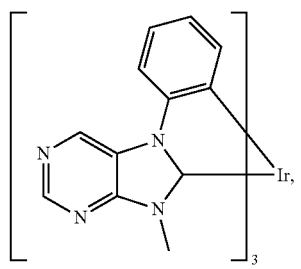
(BE-29)
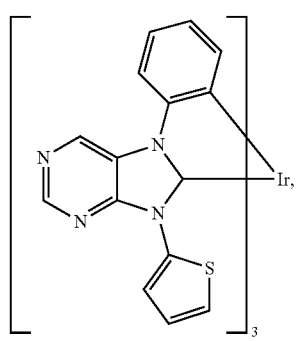
(BE-30)
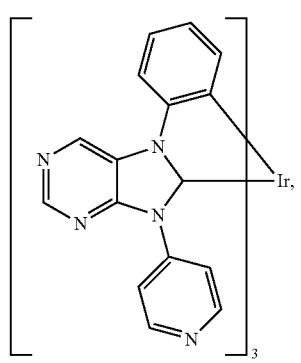
(BE-31)
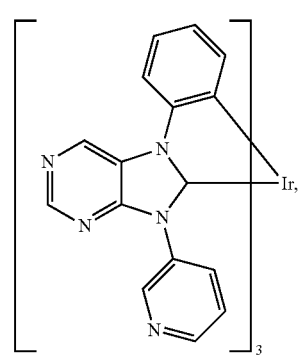
(BE-32)
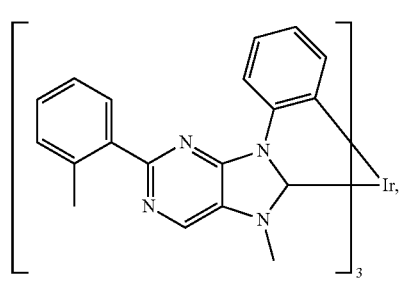
(BE-33)
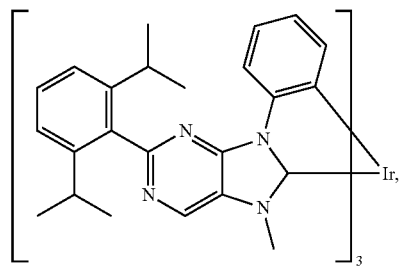
(BE-34)
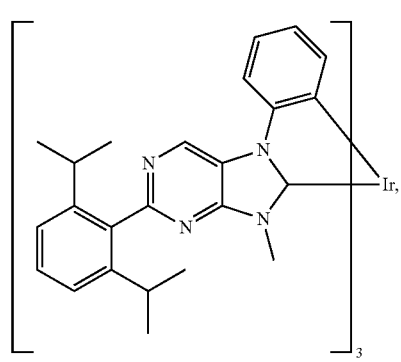
(BE-35)
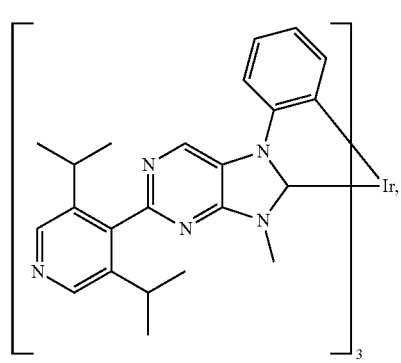

(BE-36)
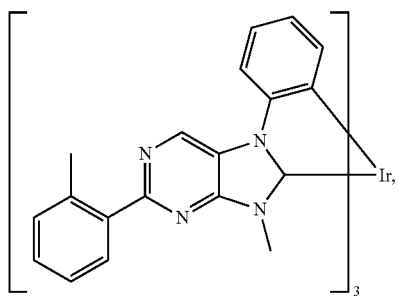
(BE-37)
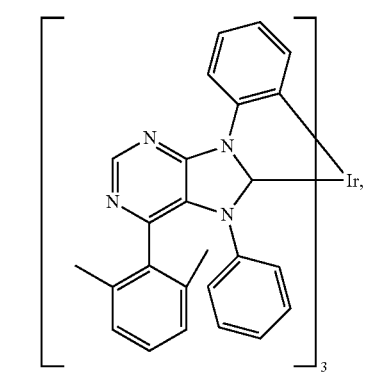
(BE-38)
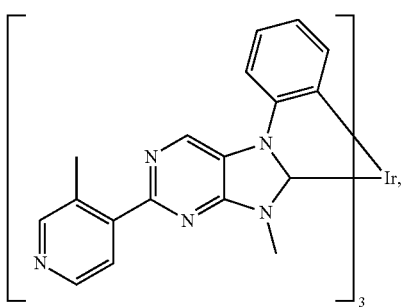
(BE-39)
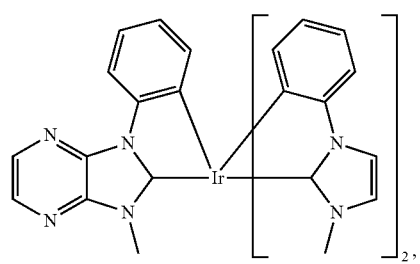
(BE-40)
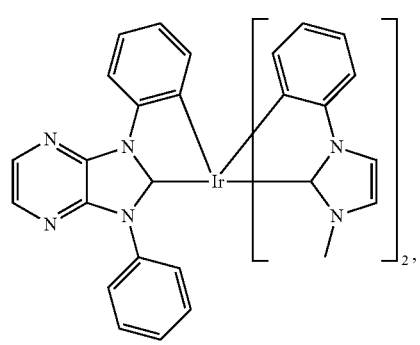
(BE-41)
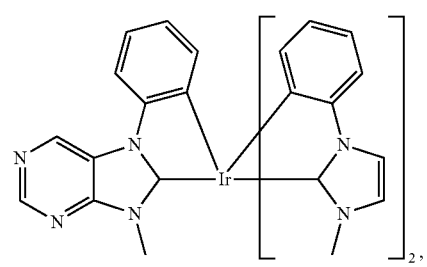
(BE-42)
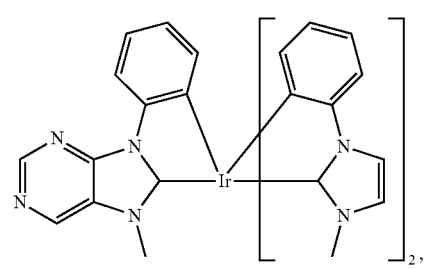
(BE-43)
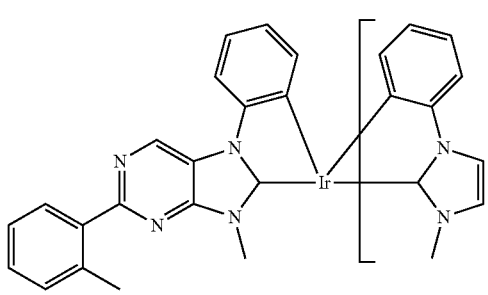
(BE-44)
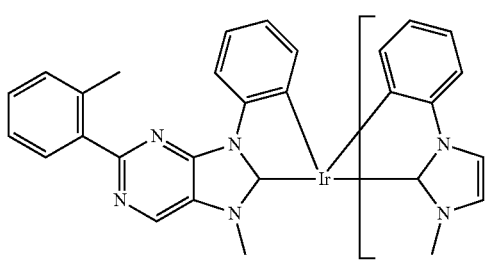
(BE-45)
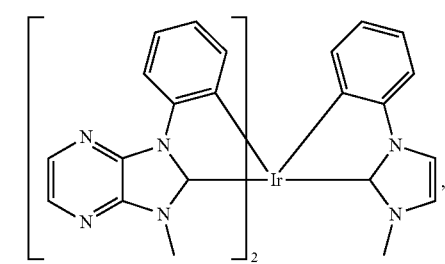

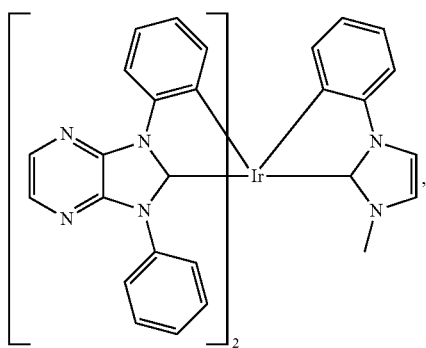
(BE-46)
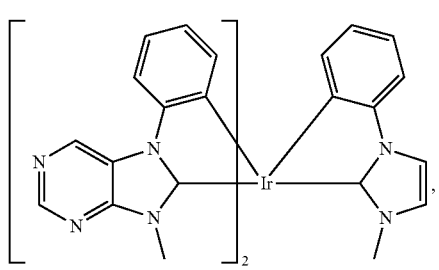
(BE-47)
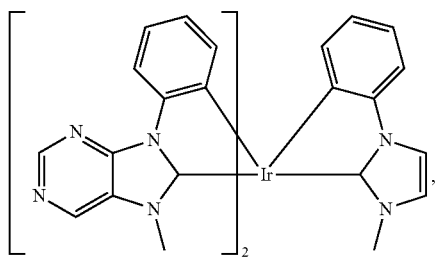
(BE-48)
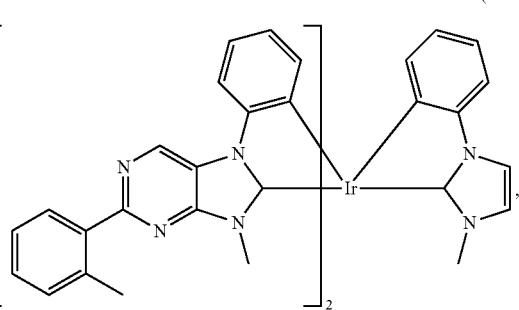
(BE-49)
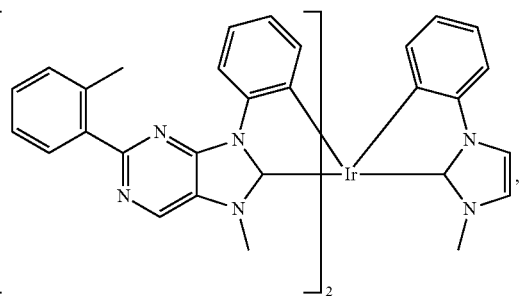
(BE-50)
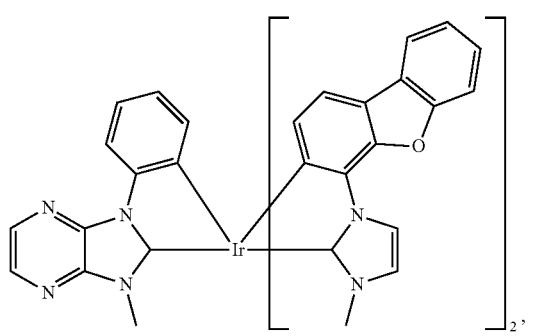
(BE-51)
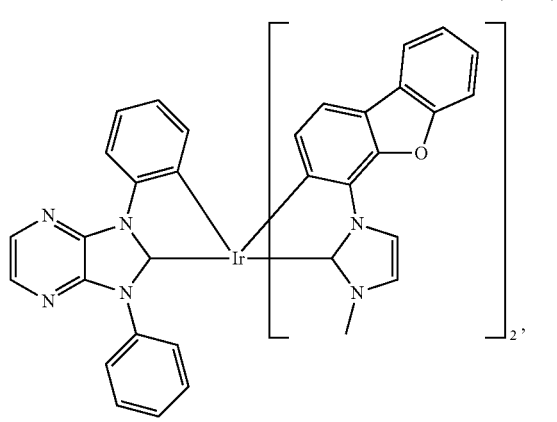
(BE-52)
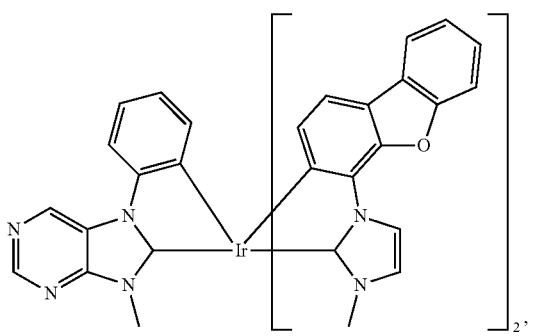
(BE-53)
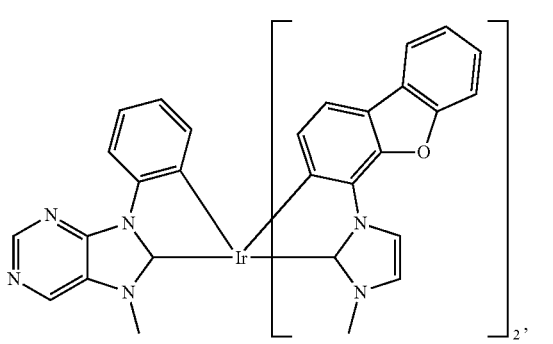
(BE-54)

(BE-55)
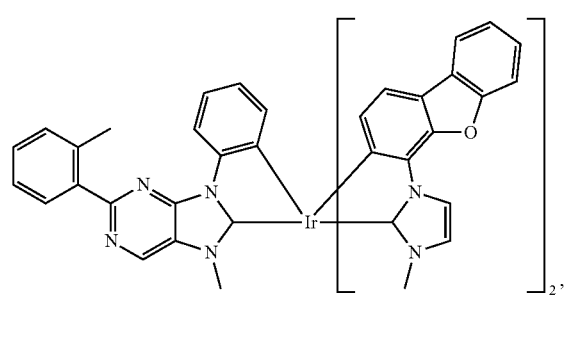
(BE-59)
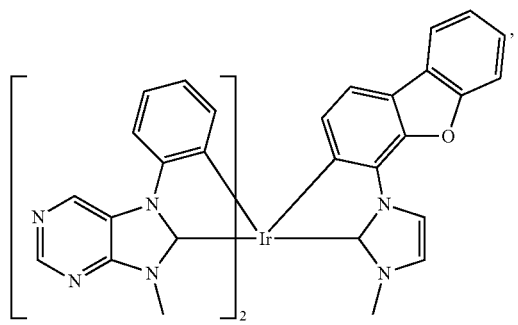
(BE-56)
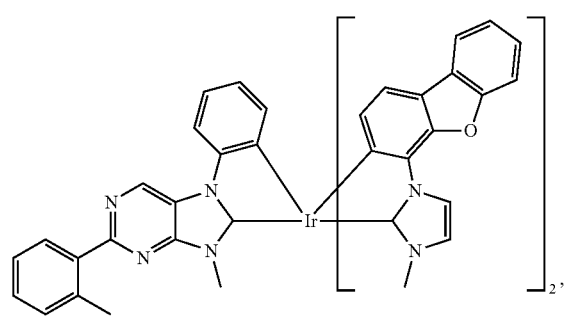
(BE-60)
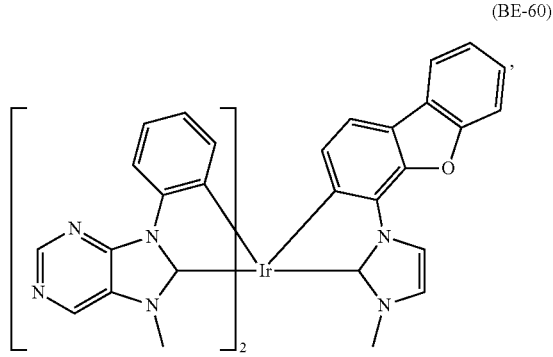
(BE-57)
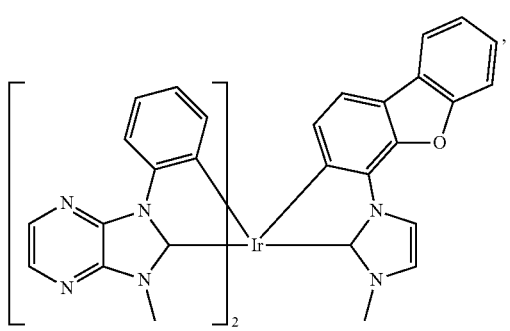
(BE-61)
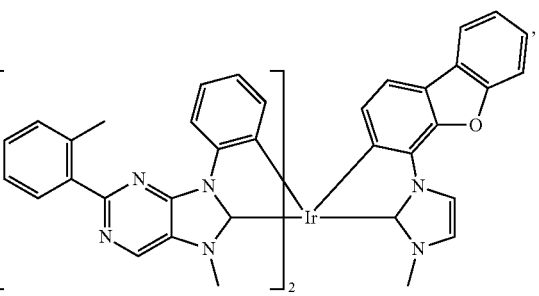
(BE-58)
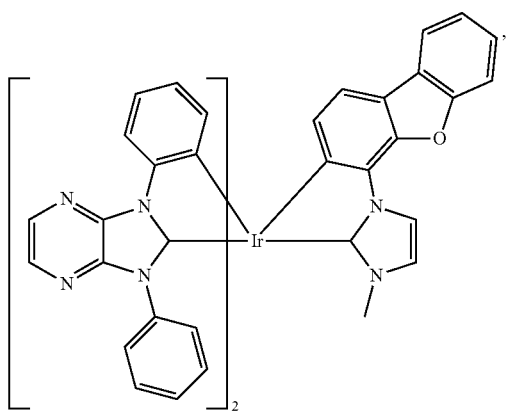
(BE-62)

(BE-63)
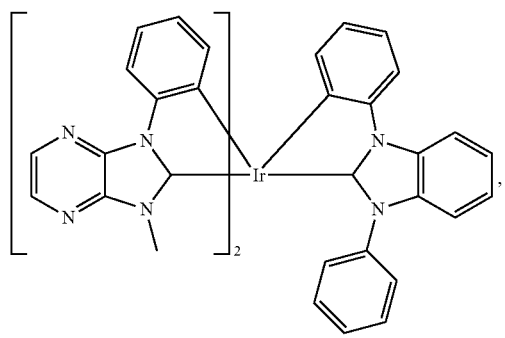
(BE-67)
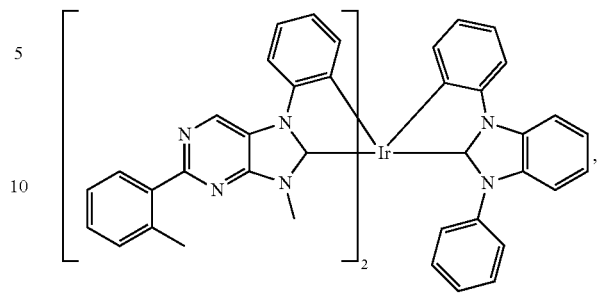
(BE-64)
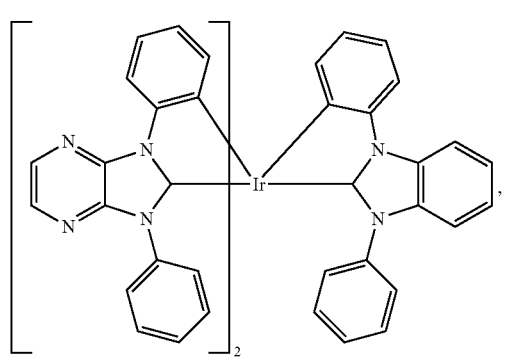
(BE-68)
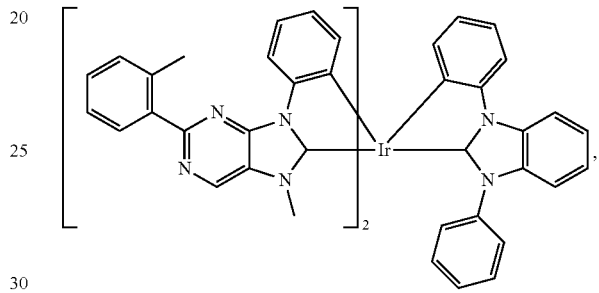
(BE-65)
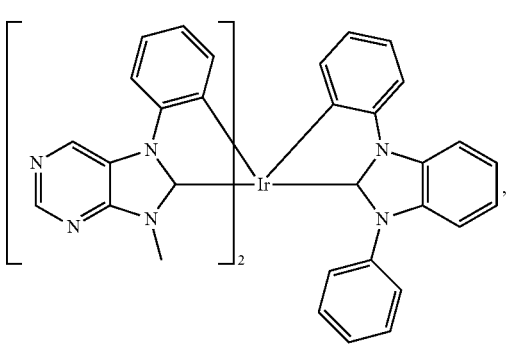
(BE-69)
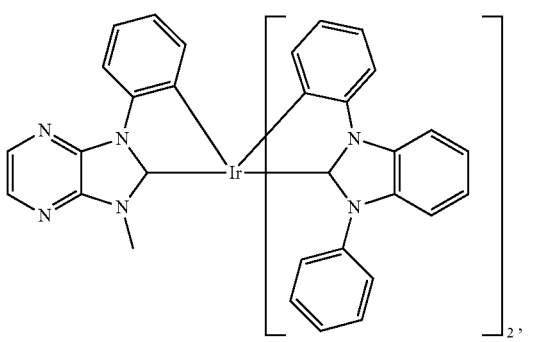
(BE-66)
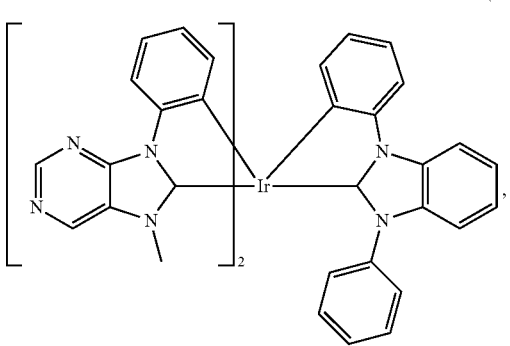
(BE-70)
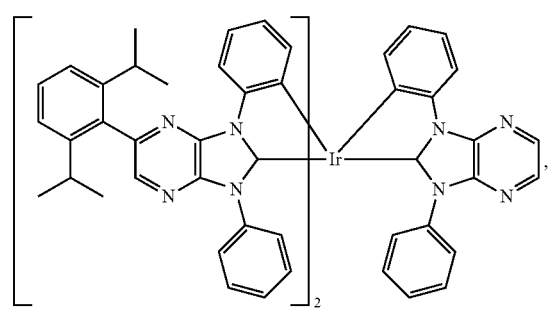

-continued
(BE-71)
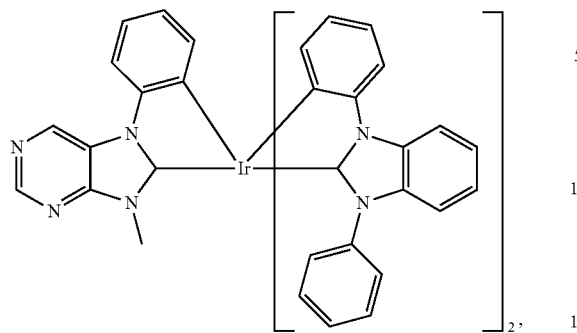
(BE-75)
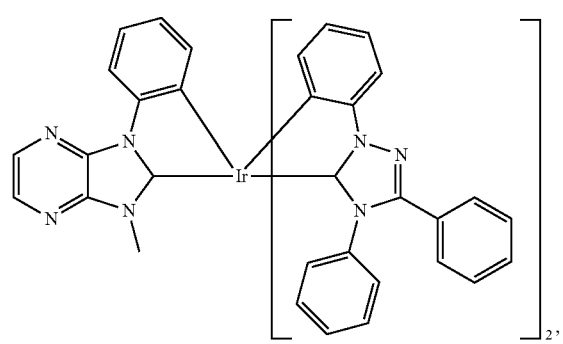
(BE-72)
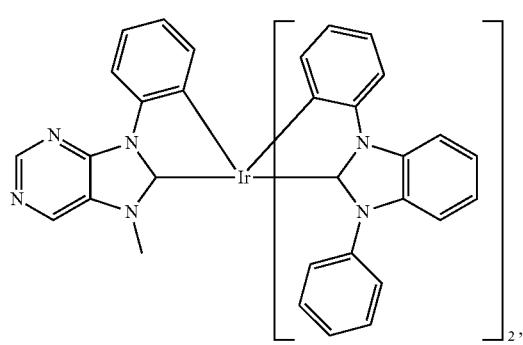
(BE-76)
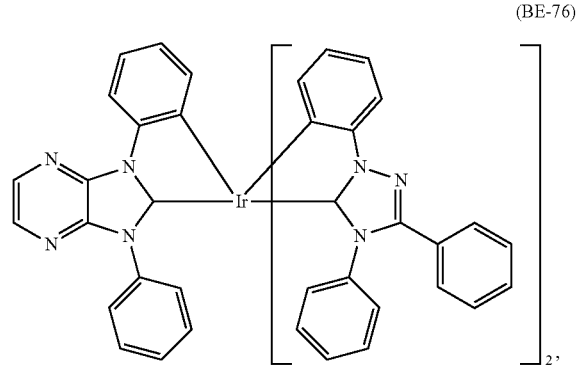
(BE-73)
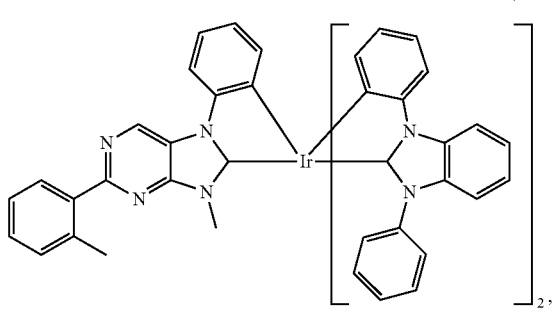
(BE-77)
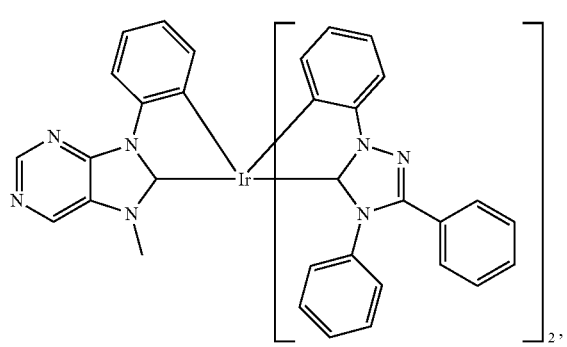
(BE-74)
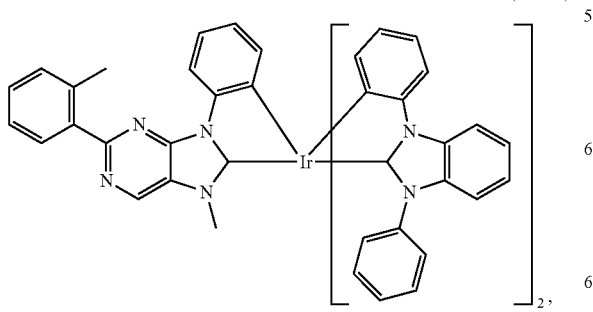
(BE-78)
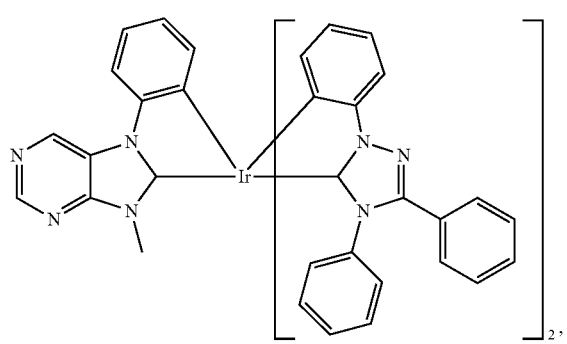

(BE-79)
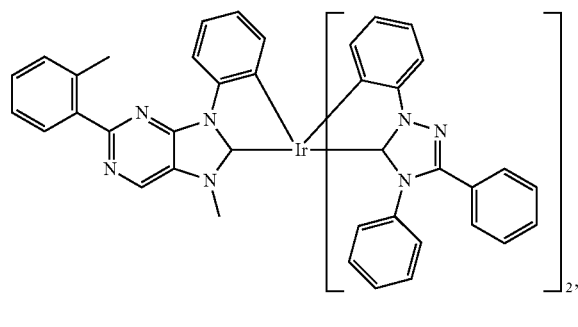
(BE-83)
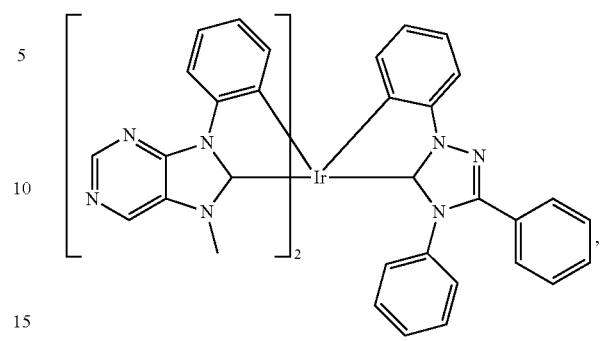
(BE-80)
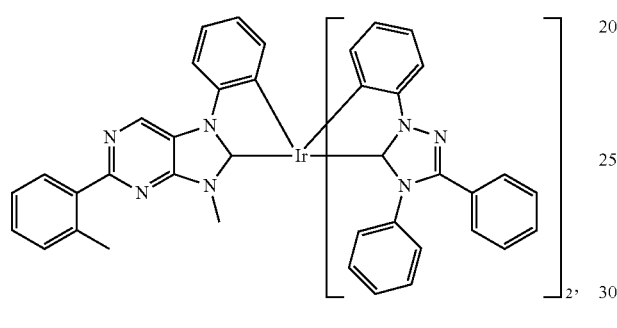
(BE-84)
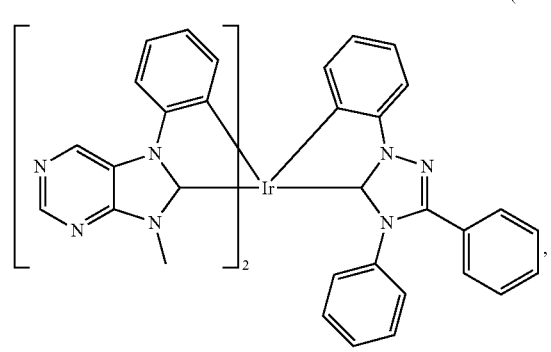
(BE-81)
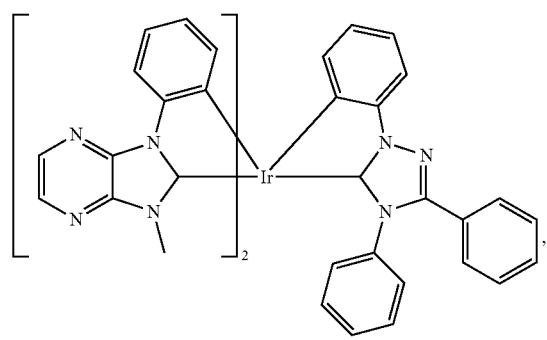
(BE-85)
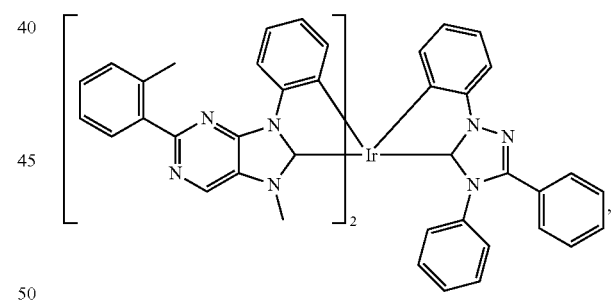
(BE-82)
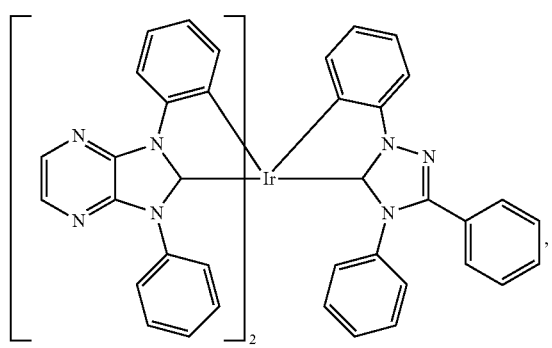
(BE-86)
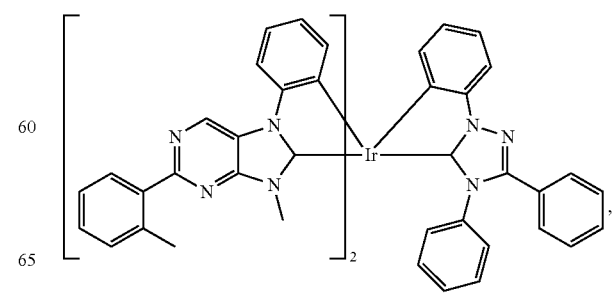

(BE-87)
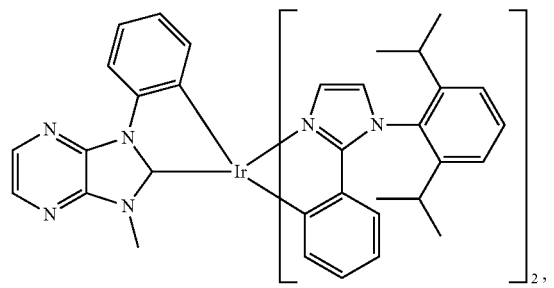
(BE-91)
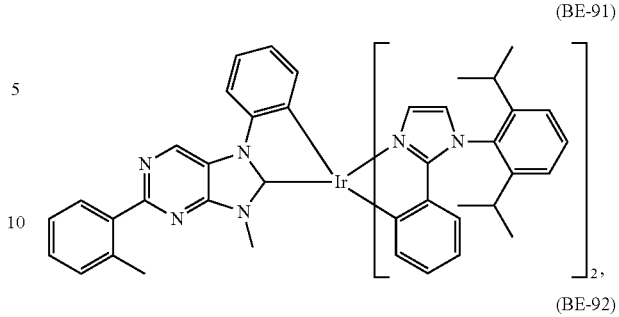
(BE-87)
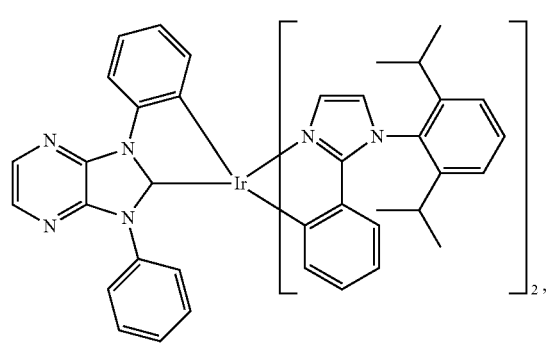
(BE-92)
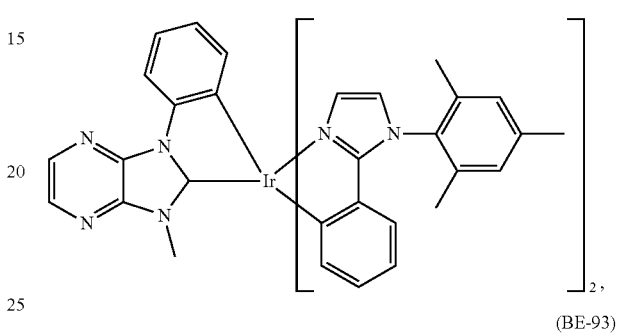
(BE-88)
(BE-93)
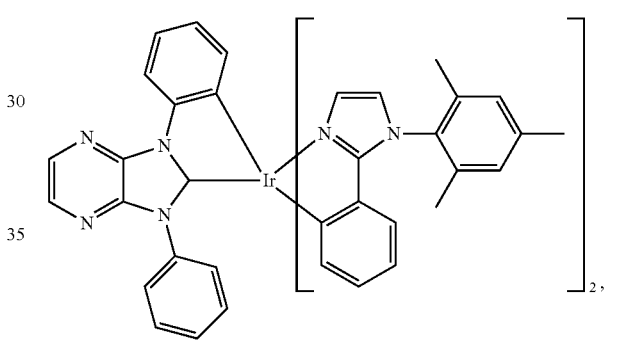
(BE-89)
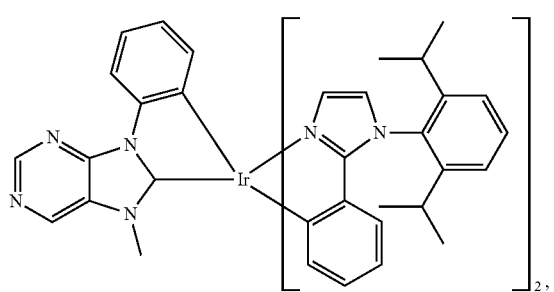
(BE-94)
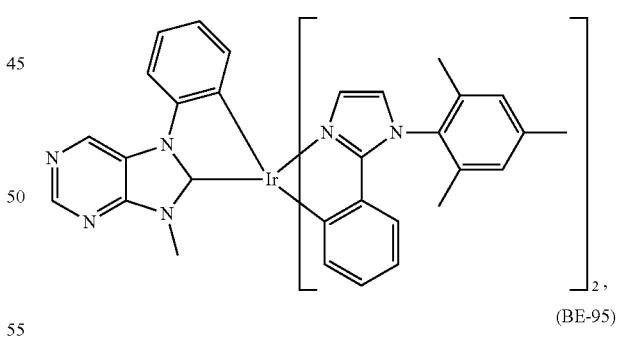
(BE-90)
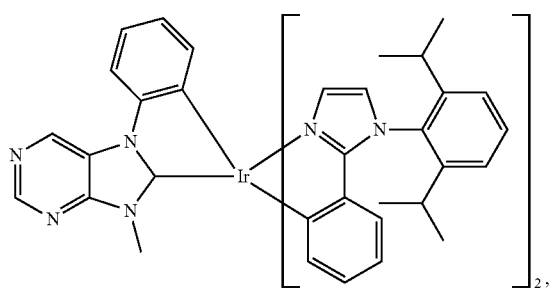
(BE-95)
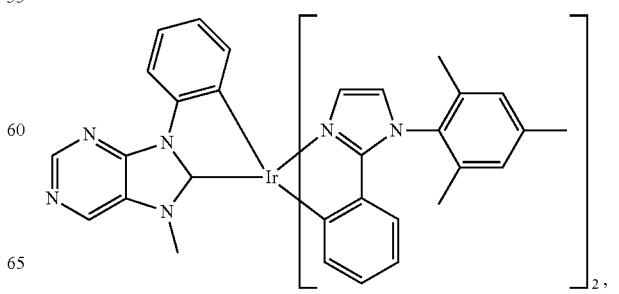
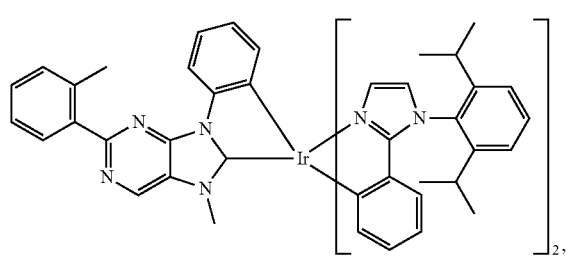

(BE-96)
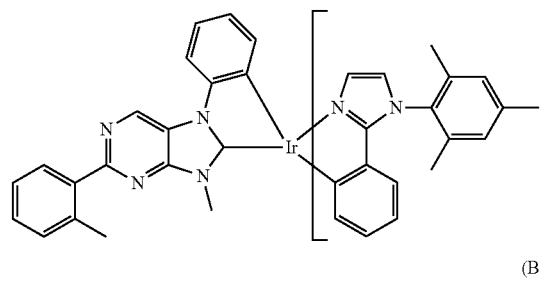
(BE-97)
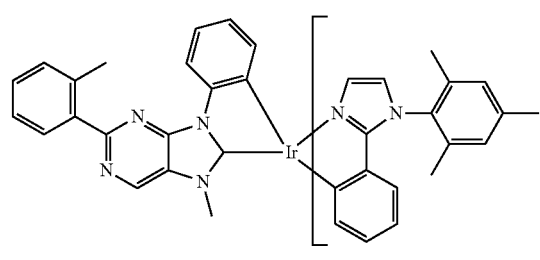
(BE-98)
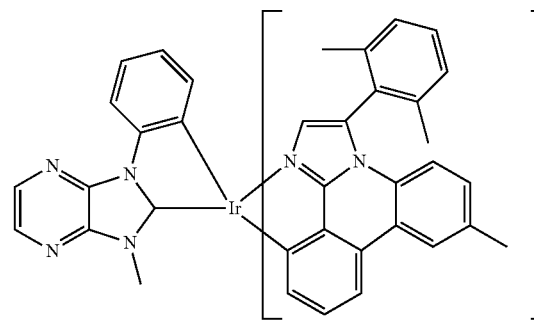
(BE-99)
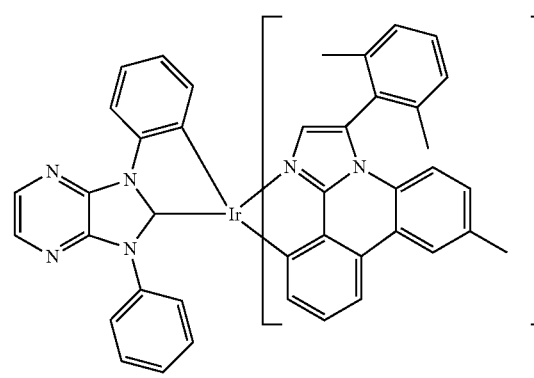
(BE-100)
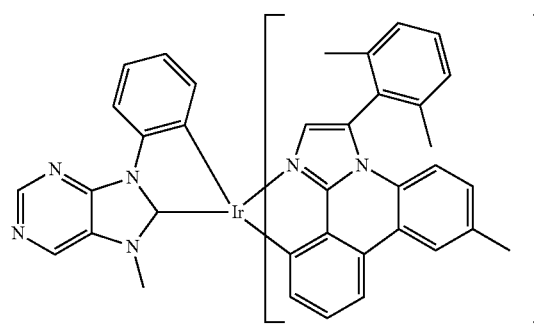
(BE-101)
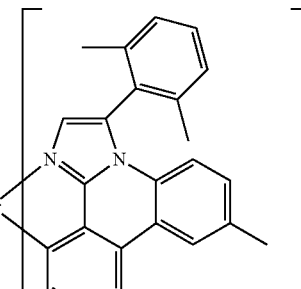
(BE-102)
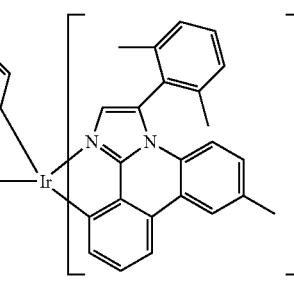
(BE-103)
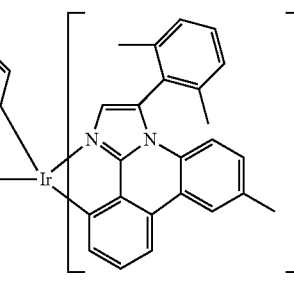
Further suitable non-carbene emitter materials are mentioned below:
(BE-104)
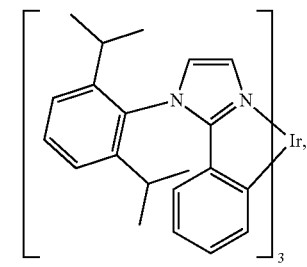
(BE-105)
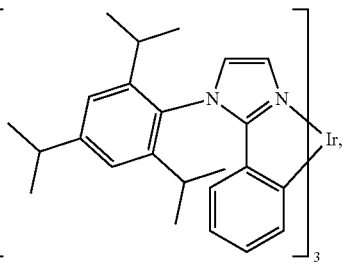

(BE-106)
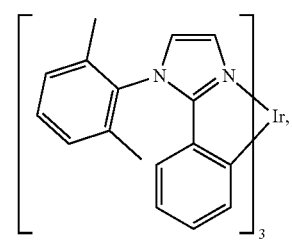
(BE-107)
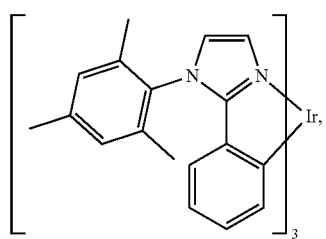
(BE-108)
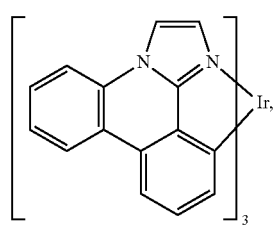
(BE-109)
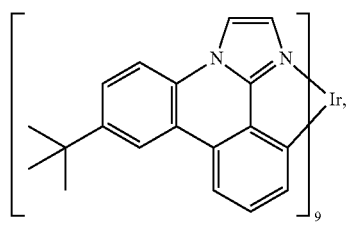
(BE-110)
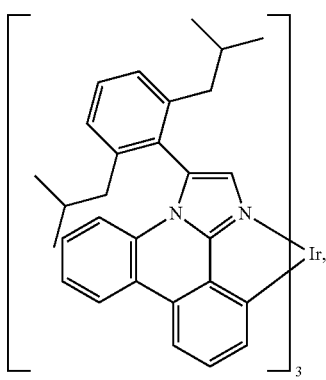
(BE-111)
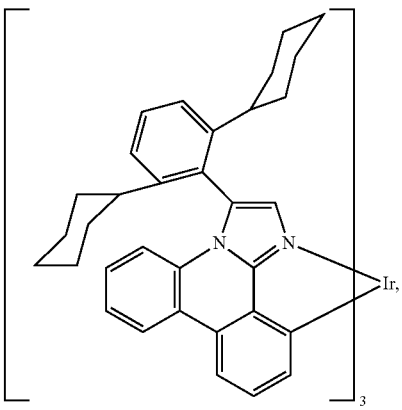
(BE-112)
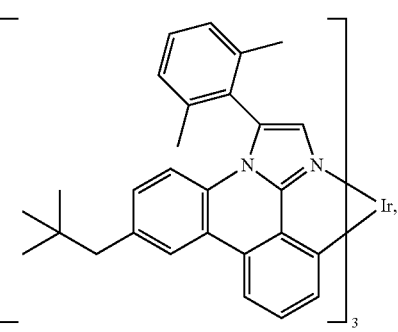
(BE-113)
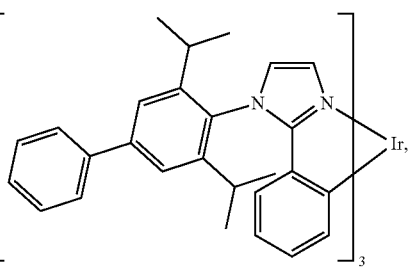
(BE-114)
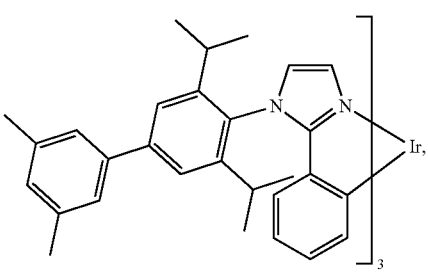
(BE-115)
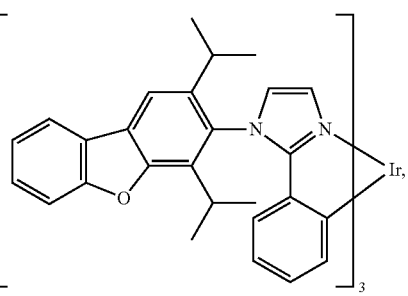

-continued
(BE-116)
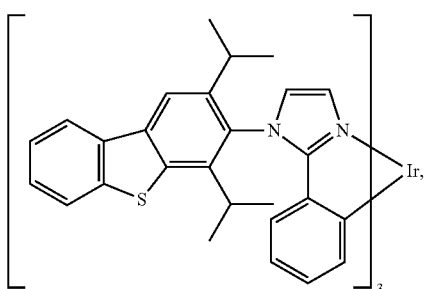
(BE-117)
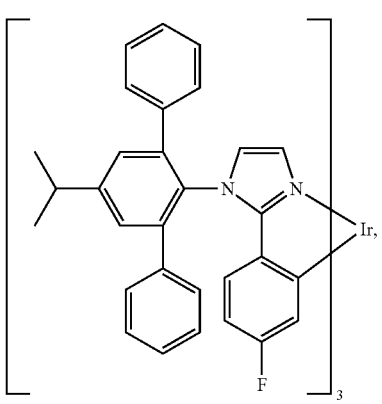
(BE-118)
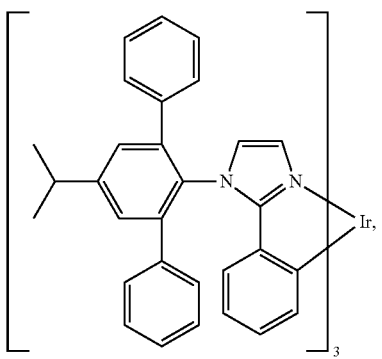
(BE-119)
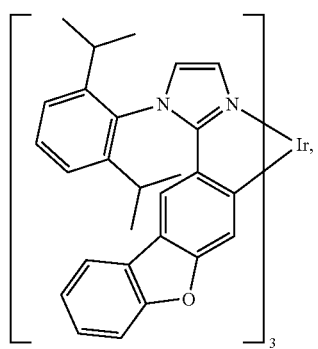
(BE-120)
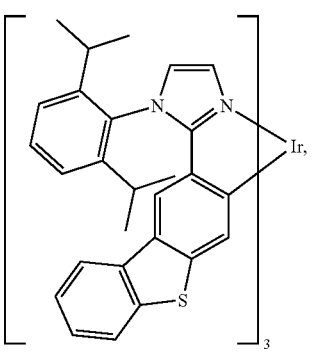
(BE-121)
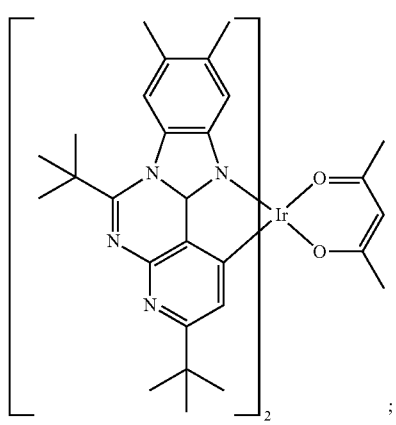
(BE-122)
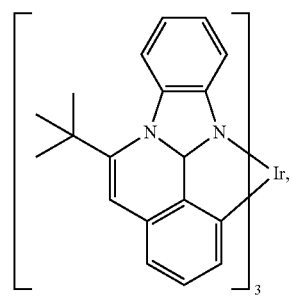
(BE-123)
(BE-124)
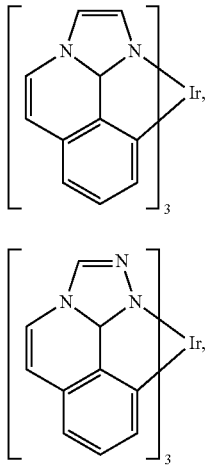

(BE-125)

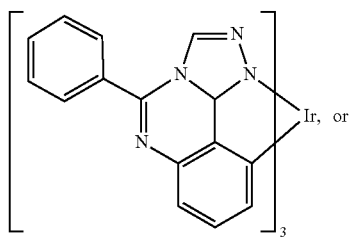

or (BE-126)

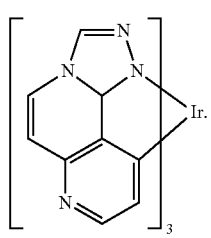

The compound of formula XIV is more preferably a compound (BE-1), (BE-2), (BE-7), (BE-12), (BE-16), (BE-64), or (BE-70). The most preferred phosphorescent blue emitters are compounds (BE-1) and (BE-12).

The homoleptic metal-carbene complexes may be present in the form of facial or meridional isomers or mixtures thereof, preference being given to the facial isomers.

Suitable carbene complexes of formula (XIV) and their preparation process are, for example, described in WO2011/073149.

The compounds of the present invention can also be used as host for phosphorescent green emitters. Suitable phosphorescent green emitters are, for example, specified in the following publications: WO2006014599, WO20080220265, WO2009073245, WO2010027583, WO2010028151, US20110227049, WO2011090535, WO2012/08881, WO20100056669, WO20100118029, WO20100244004, WO2011109042, WO2012166608, US20120292600, EP2551933A1; U.S. Pat. No. 6,687,266, US20070190359, US20070190359, US20060008670; WO2006098460, US20110210316, WO2012053627; U.S. Pat. No. 6,921,915, US20090039776; JP2007123392 and European patent application no. 14180422.9.

Examples of suitable phosphorescent green emitters are shown below:

(GE-1)

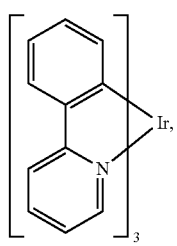

(GE-2)

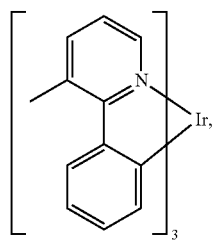

(GE-3)

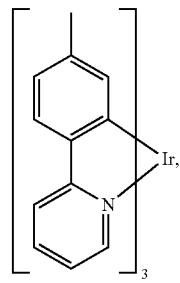

(GE-4)

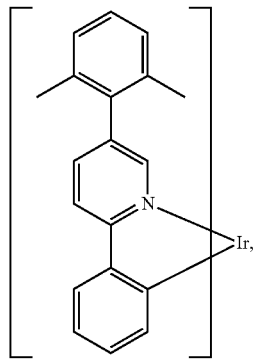

(GE-5)

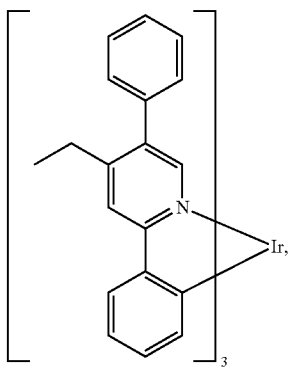

(GE-6)

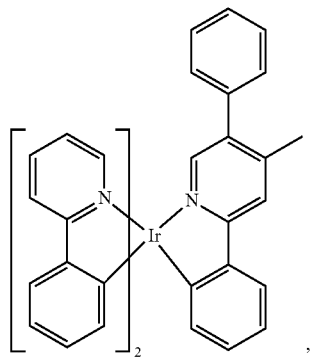

(GE-7)
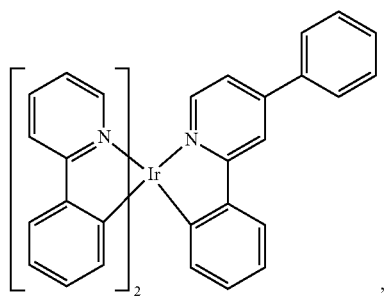
(GE-8)
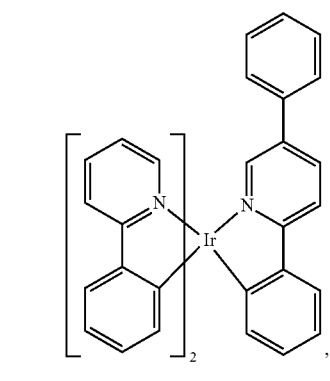
(GE-9)
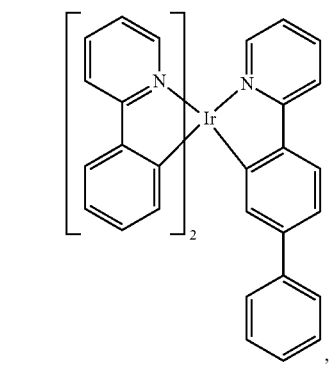
(GE-10)
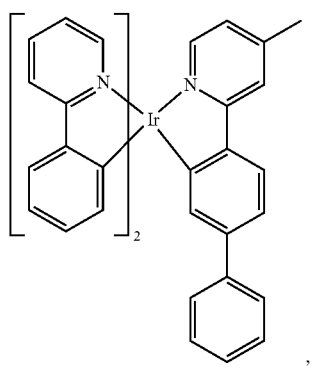
(GE-11)
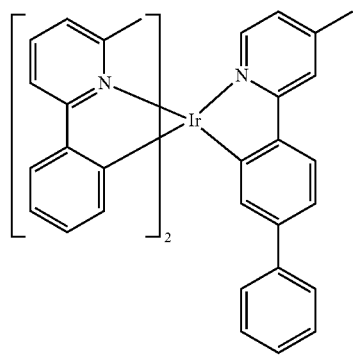
(GE-12)
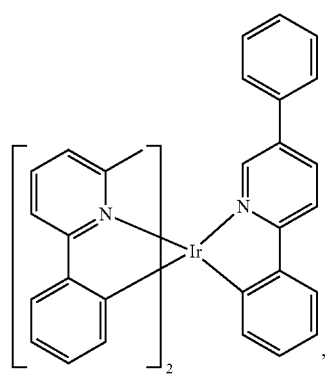
(GE-13)
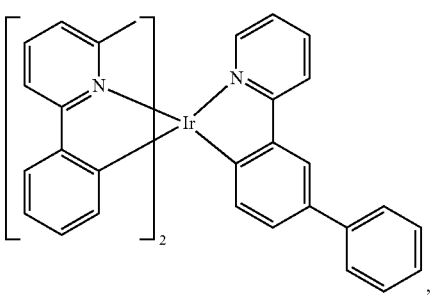
(GE-14)
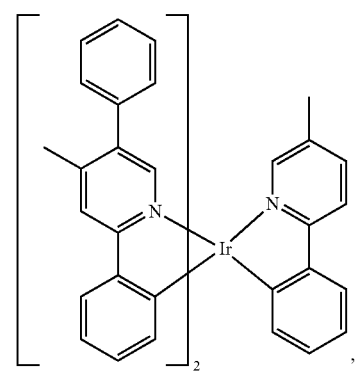

(GE-15)
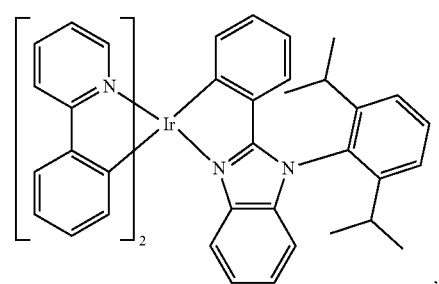
(GE-16)
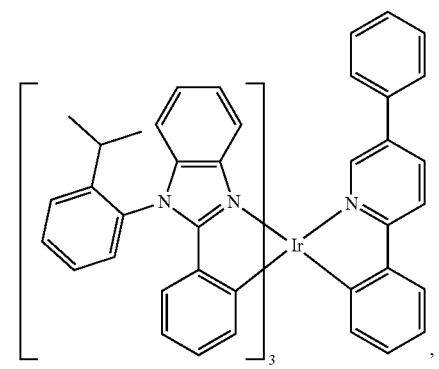
(GE-17)
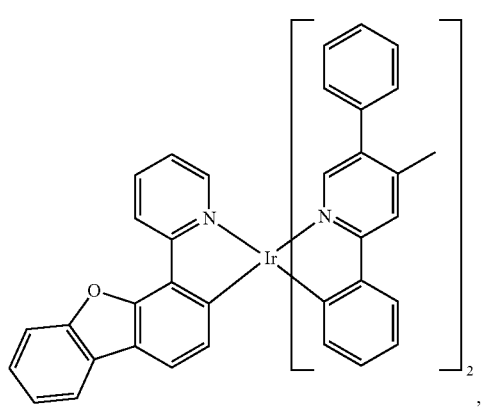
(GE-18)
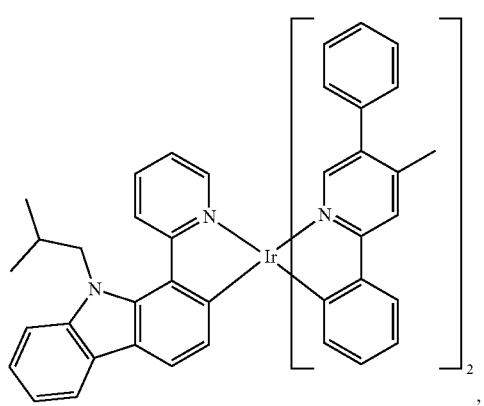
(GE-19)
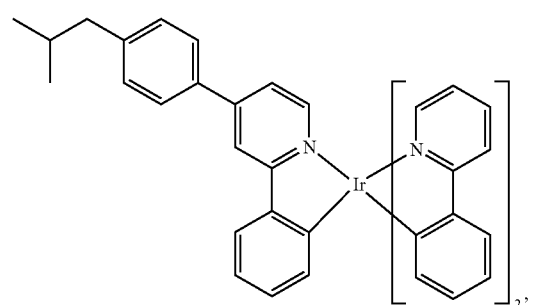
(GE-20)
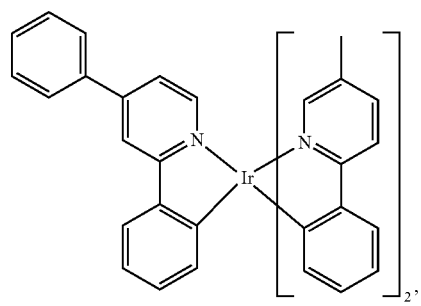
(GE-21)
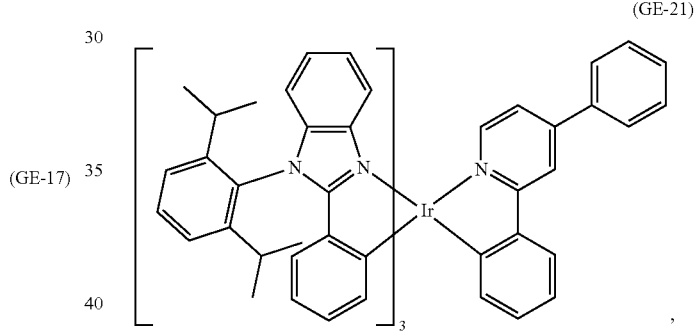
(GE-22)
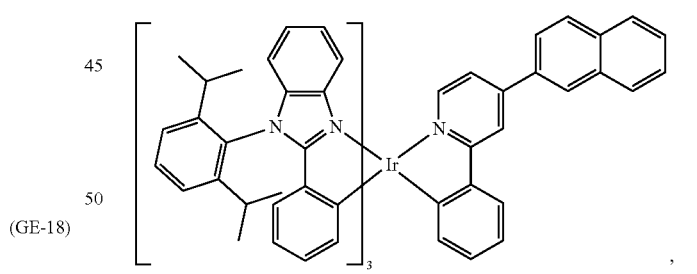
(GE-23)
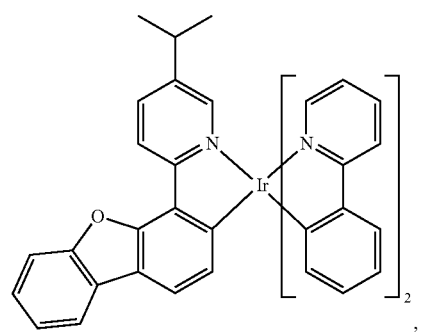

(GE-24)
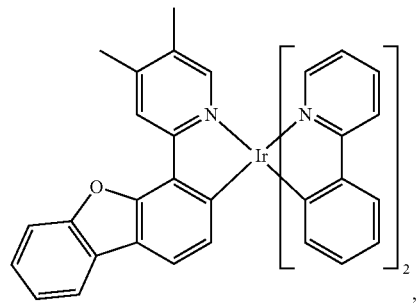
(GE-25)
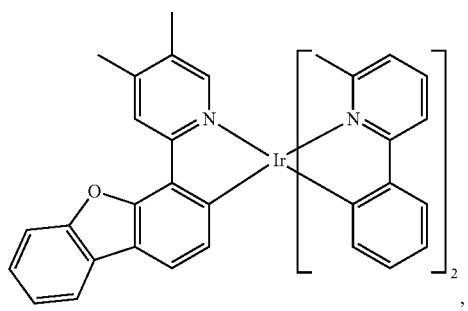
(GE-26)
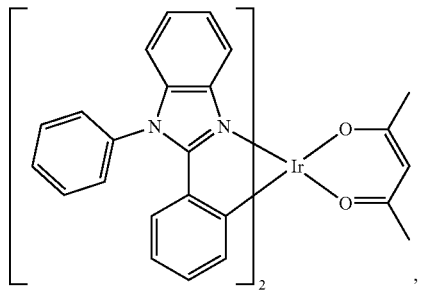
(GE-27)
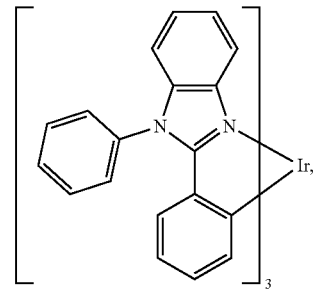
(GE-28)
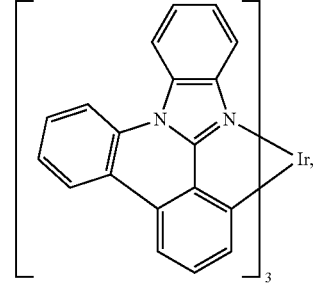
(GE-29)
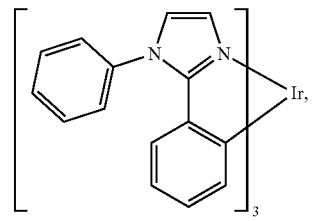
(GE-30)
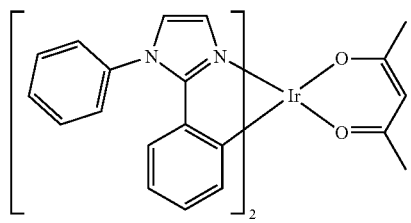
(GE-31)
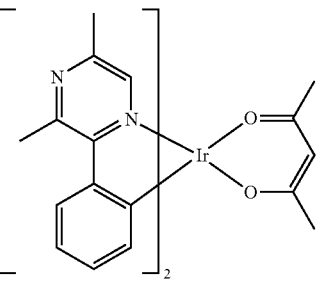
(GE-32)
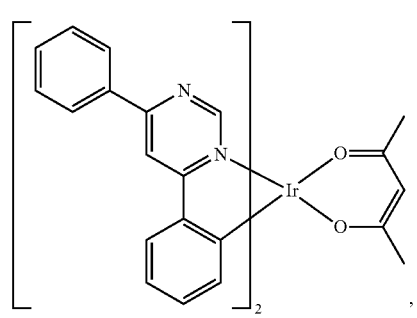
(GE-33)
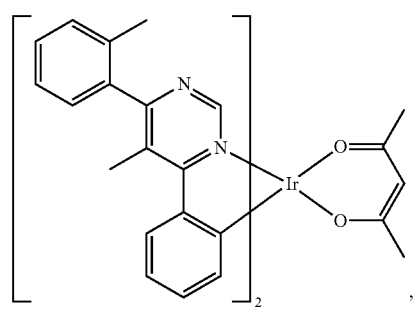
(GE-34)
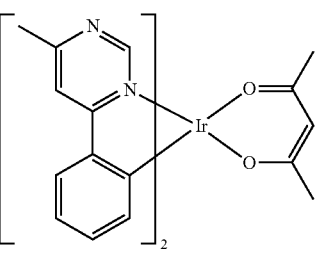

-continued (GE-35)
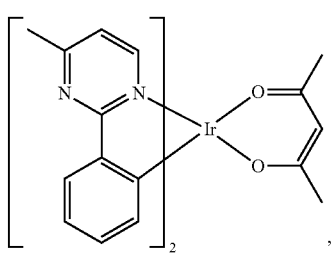

(GE-36)
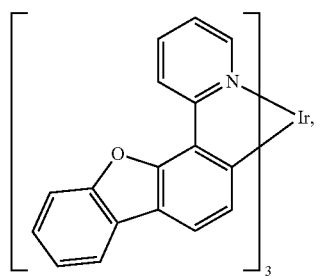

(GE-37)
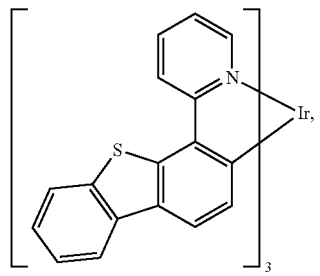

(GE-38)
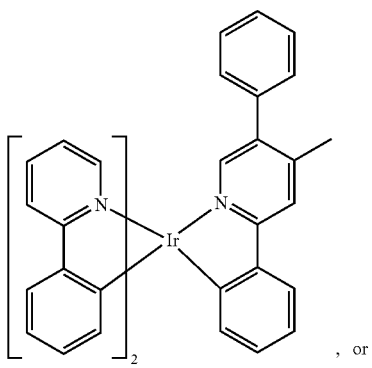, or (GE-39)
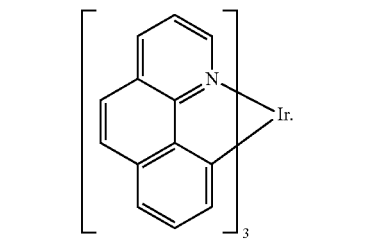

Host (Matrix) Materials

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA.

In a preferred embodiment, the light-emitting layer is formed of at least one emitter material and of at least one of the matrix materials—in one embodiment at least one compound of the formula I. Suitable emitter materials and matrix materials are mentioned in the specification. In one embodiment, the light-emitting layer comprises at least one emitter material and at least to matrix materials, wherein one of the matrix materials is a first host material and the other is a second host material. The matrix materials mentioned in the specification are suitable as first and second host materials.

In another preferred embodiment of the present invention, at least one compound of the formula I is used as host material. Examples of preferred compounds of formula I useful as host material are shown above.

In a more preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the matrix materials mentioned in the specification—in one embodiment at least one compound of the formula I—where the sum total of the emitter material and of the matrix material adds up to 100% by weight.

In a particularly preferred embodiment, the light-emitting layer comprises a compound of formula I and two carbene complexes, preferably BE-1 and HTM-1, or HTM-2. In said embodiment, the light-emitting layer is formed from 2 to 40% by weight, preferably 5 to 35% by weight, of BE-1 and 60 to 98% by weight, preferably 65 to 95% by weight, of a compound of the formula I and and HTM-1, or HTM-2, where the sum total of the carbon complexes and of the compound of formula I adds up to 100% by weight.

Suitable metal complexes for use as matrix material in OLEDs, preferably together with the compounds of the formula I, are, for example, also carbene complexes as described in WO 2005/019373 A2, WO 2006/056418 A2, WO 2005/113704, WO 2007/115970, WO 2007/115981 and WO 2008/000727.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7, EP12185230.5 and EP12191408.9 (in particular page 25 to 29 of EP12191408.9).

The above-mentioned small molecules are more preferred than the above-mentioned (co)polymers of the small molecules.

Further suitable host materials, are described in WO2011137072 (for example

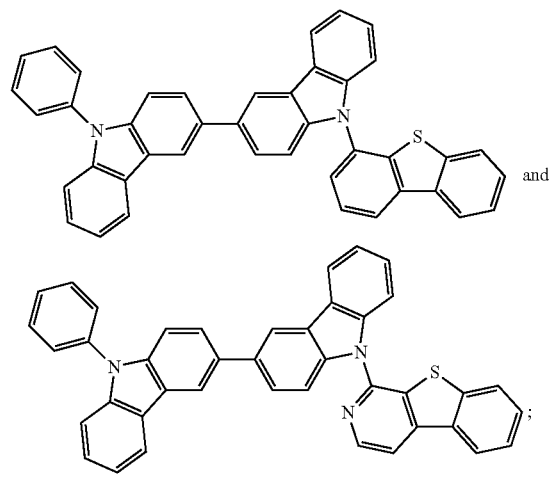

best results are achieved if said compounds are combined with

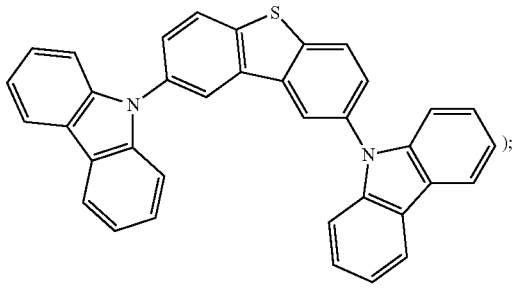 [SMILES: c1ccc2c(c1)c1ccccc1n2-c1ccc2sc3ccc(-n4c5ccccc5c5ccccc54)cc3c2c1]

WO2012048266 (for example,

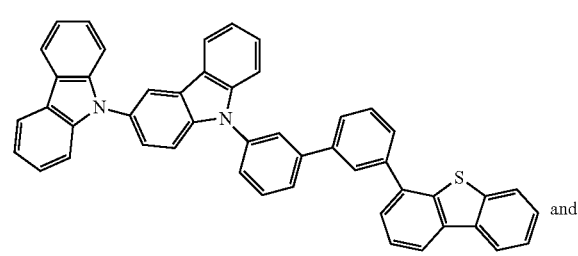

and

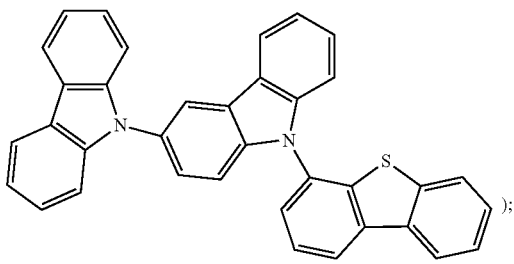

);

WO2012162325 (for example,

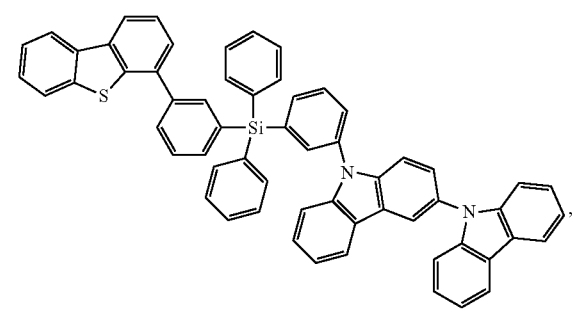

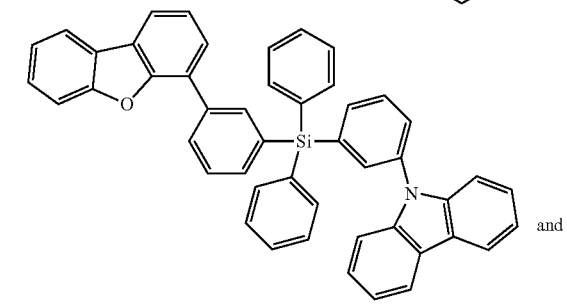

and

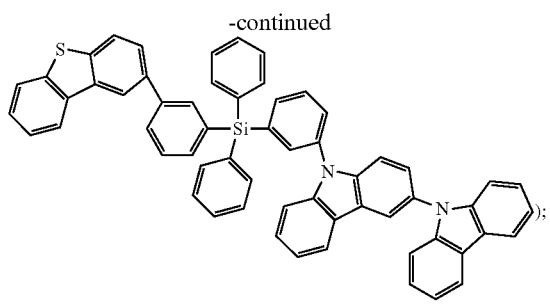

and EP2551932 (for example,

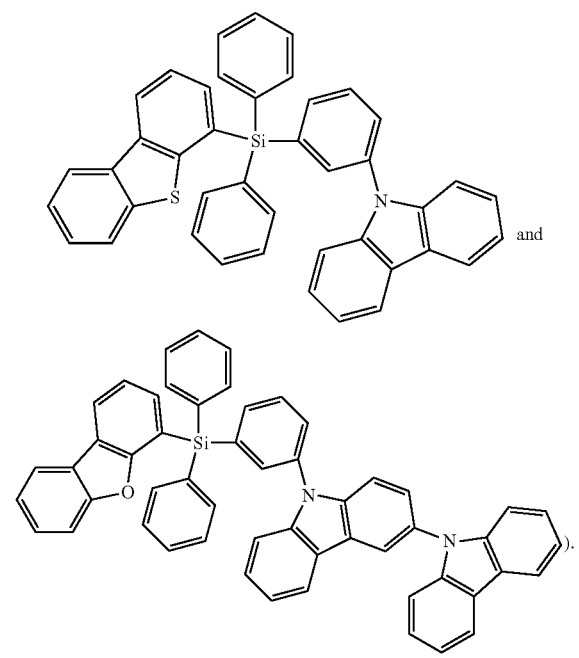

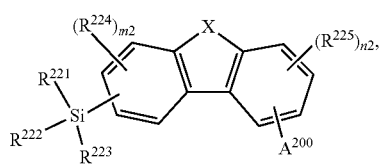

In a particularly preferred embodiment, one or more compounds of the general formula (XV) specified hereinafter are used as host material.

(XV)

wherein

X is NR, S, O or PR;

R is aryl, heteroaryl, alkyl, cycloalkyl, or heterocycloalkyl;

$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;

$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;

$R^{224}$ and $R^{225}$ are independently of each other alkyl, cycloalkyl, heterocycloalkyl, aryl, heteroaryl, a group $A^{200}$, or a group having donor, or acceptor characteristics;

n2 and m2 are independently of each other 0, 1, 2, or 3;

$R^{206}$ and $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ und $R^{215}$ are independently of each other aryl, heteroaryl, alkyl, cycloalkyl, or heterocycloalkyl. Compounds of formula XV, such as, for example,

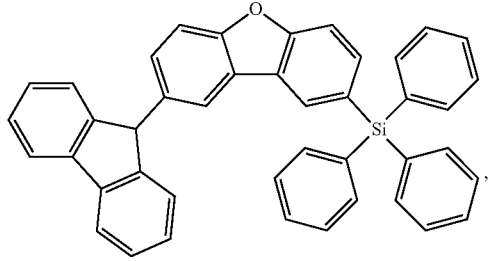
(SH-4)

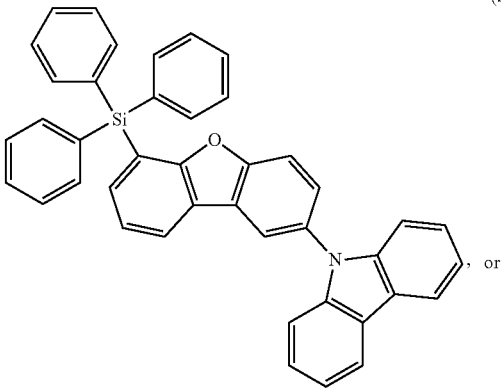
(SH-5)

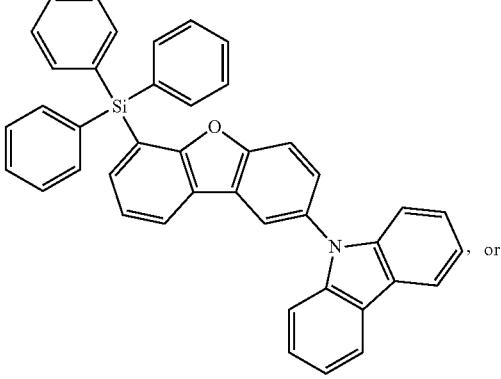

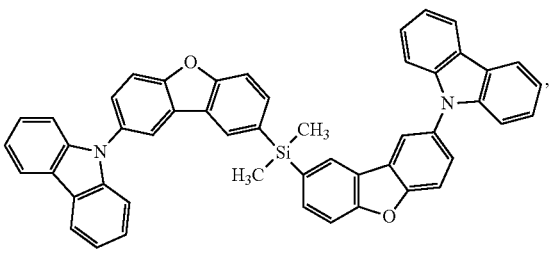
(SH-6)

are described in WO2010079051 (in particular pages on 19 to 26 and in tables on pages 27 to 34, pages 35 to 37 and pages 42 to 43).

Additional host materials on basis of dibenzofurane are, for example, described in US2009066226, EP1885818B1, EP1970976, EP1998388, EP2034538 and European patent application no. 14160197.1. Examples of particularly preferred host materials are shown below:

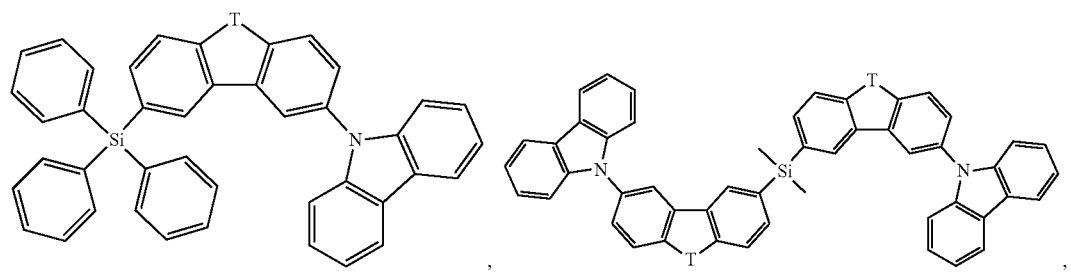
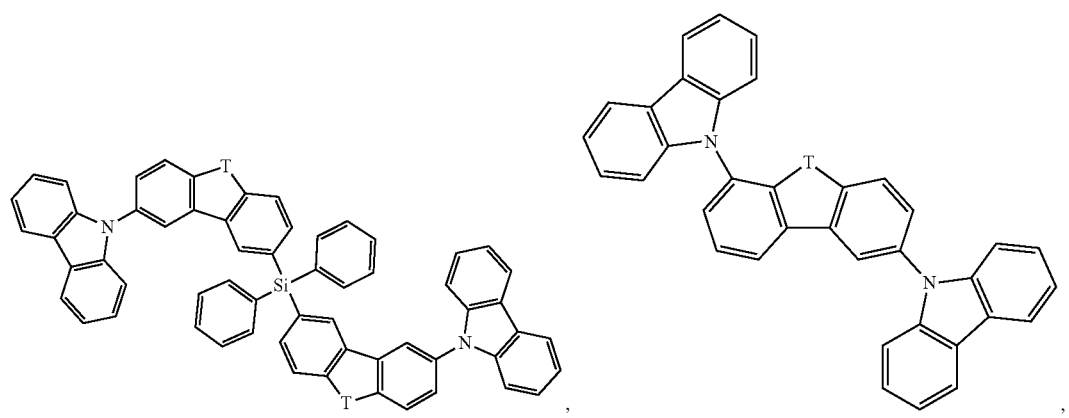
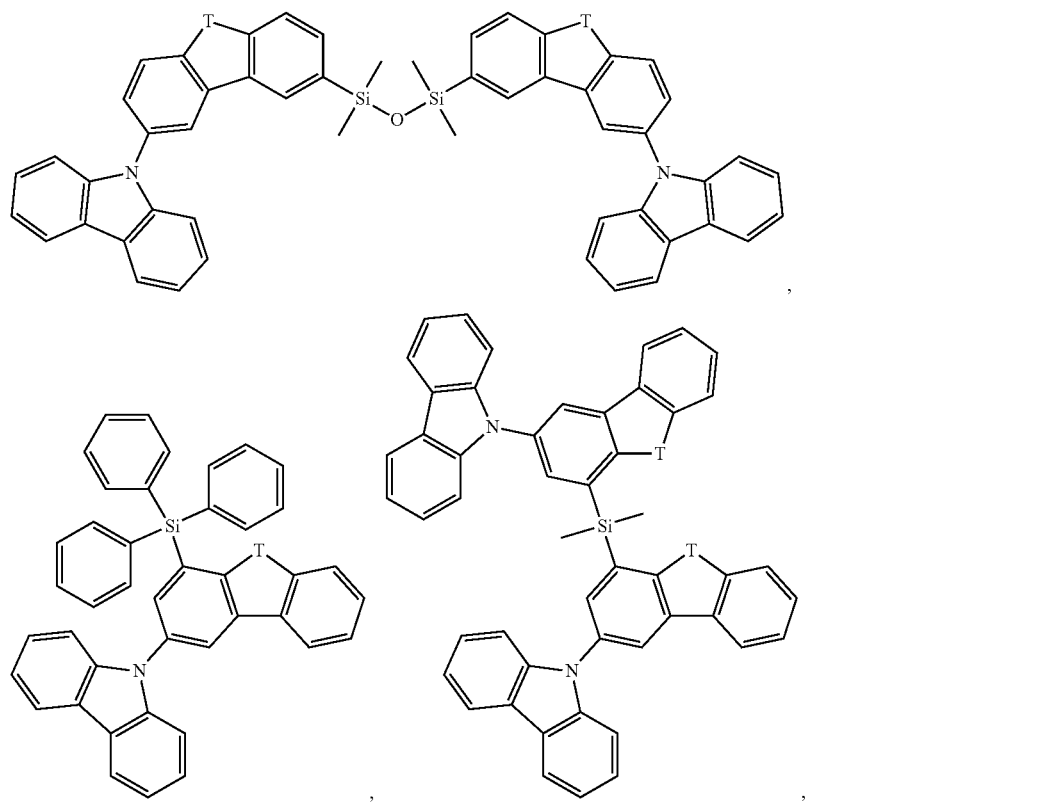

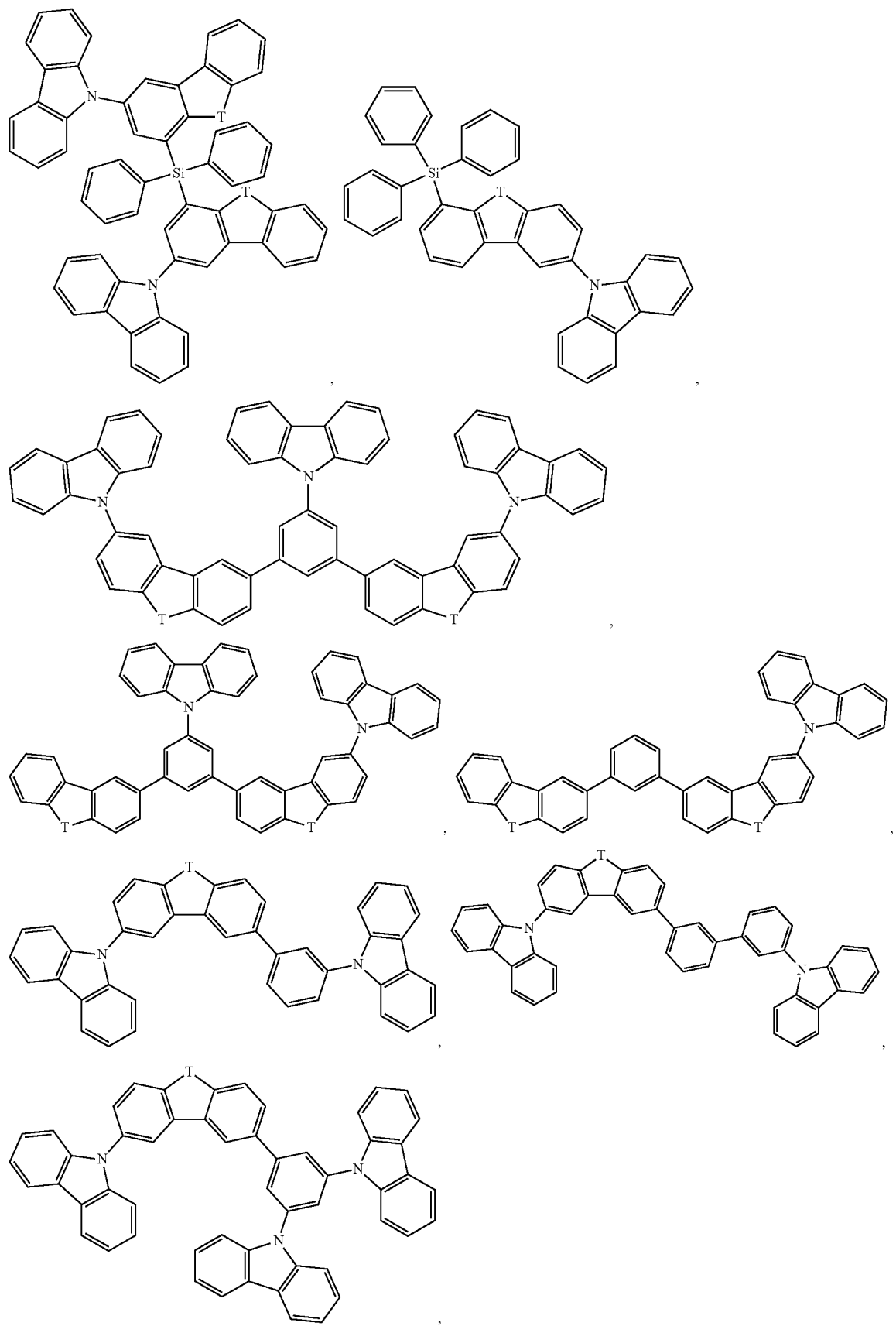

-continued
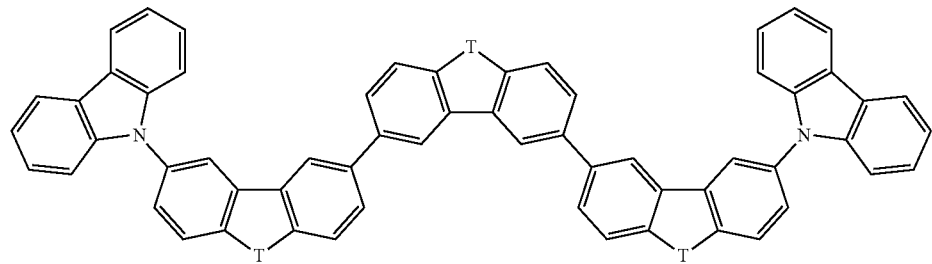,
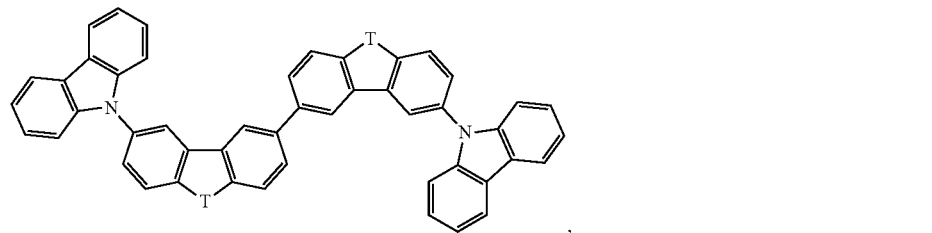,
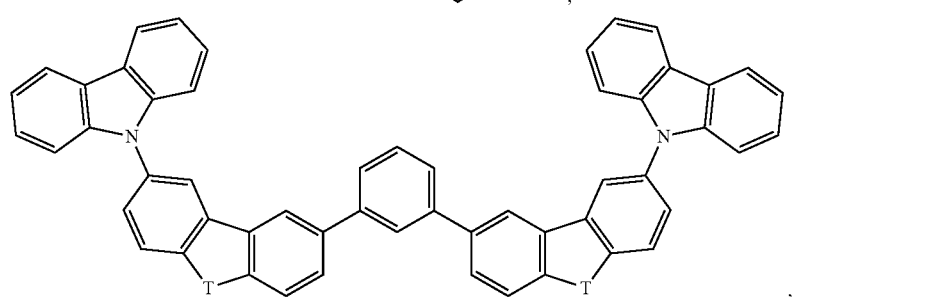,
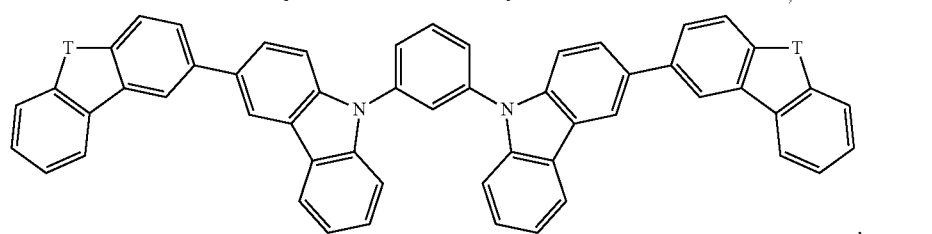,
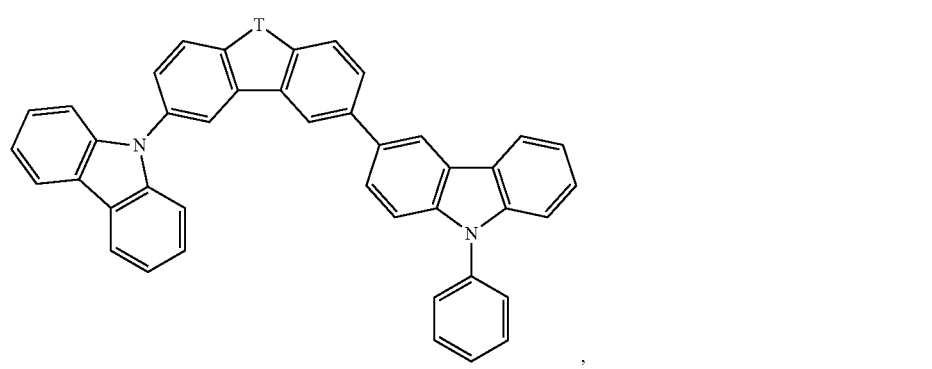,
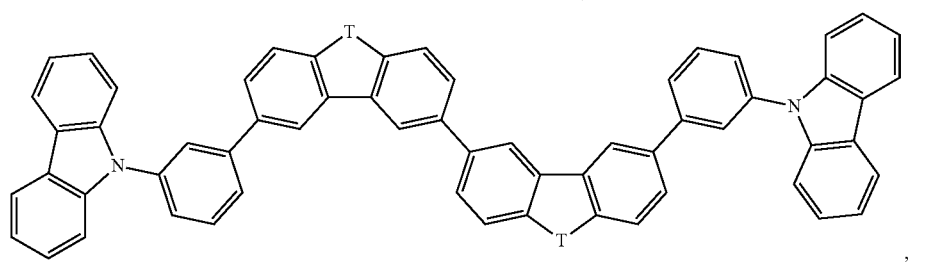,

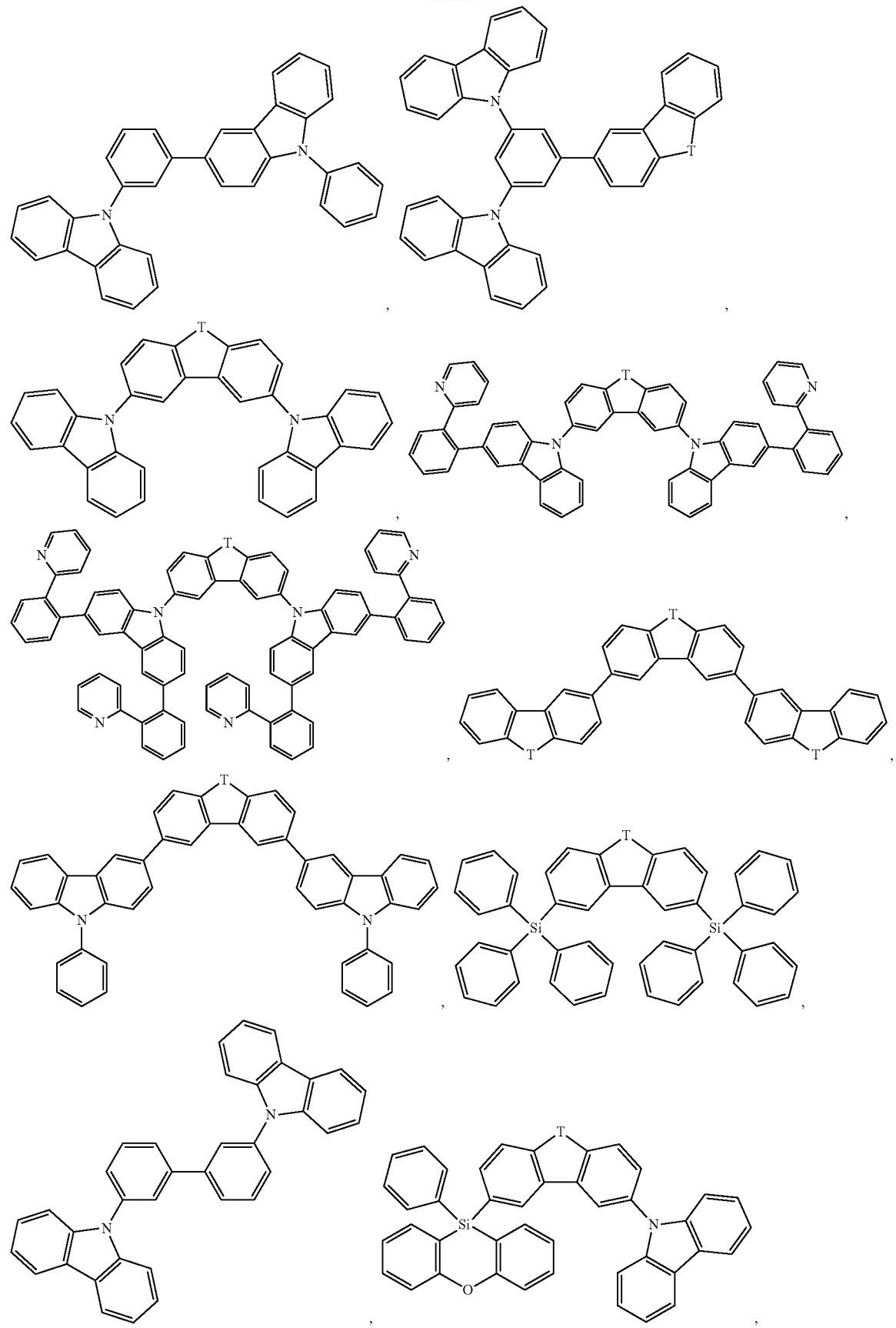

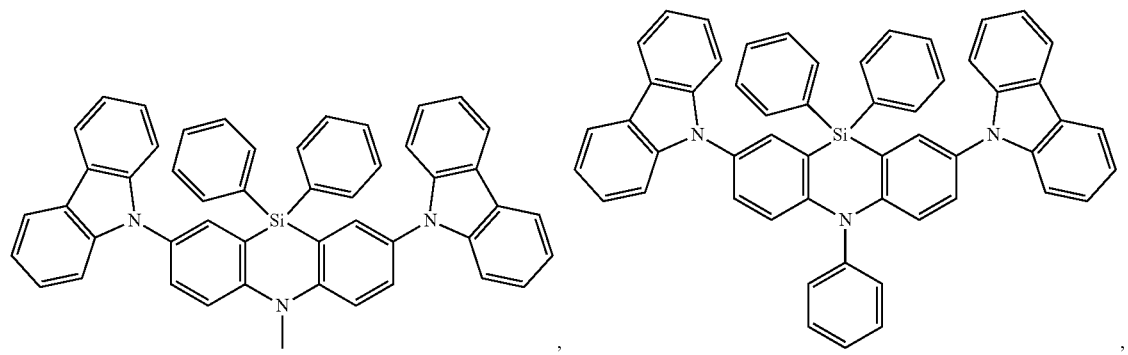
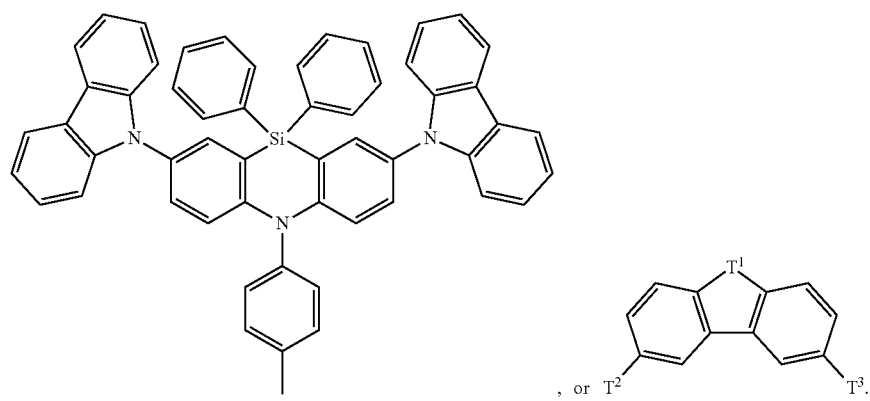
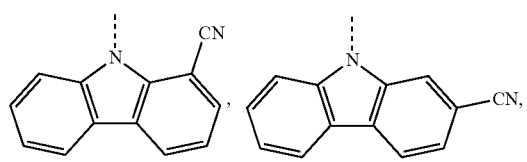, or 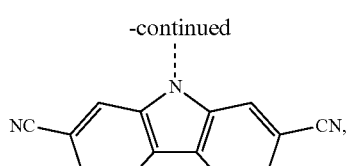
In the above-mentioned compounds T is O, or S, preferably O. If T occurs more than one time in a molecule, all groups T have the same meaning. $T^1$ is O, or S, preferably O. $T^1$ and $T^2$ are independently of each other
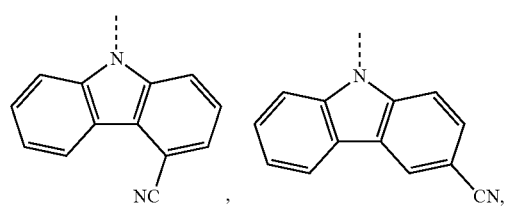
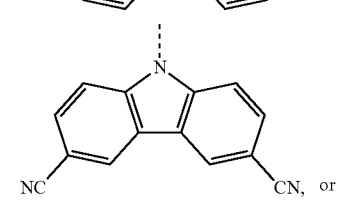
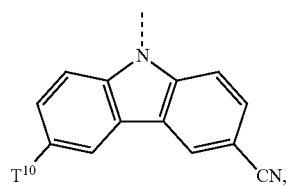, or
wherein $T^{10}$ is a $C_1$-$C_{25}$ alkyl group.

Compounds
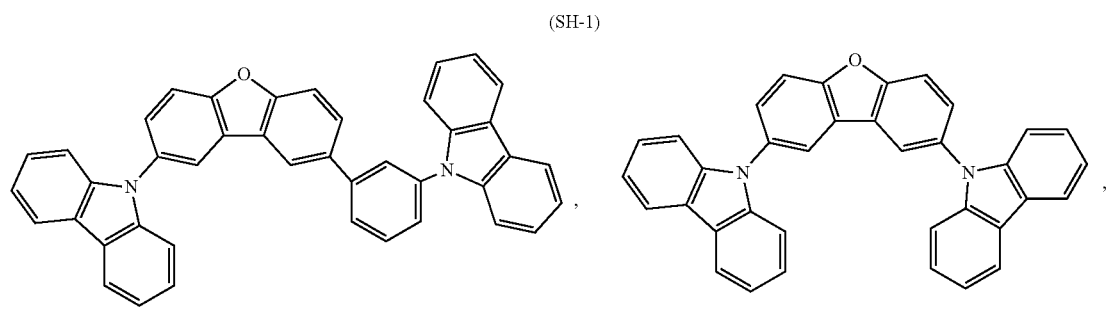
(SH-1) (SH-2)
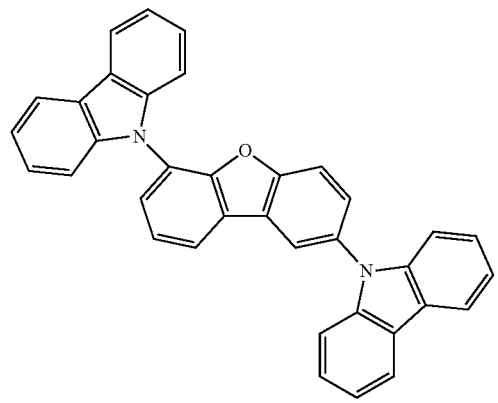
(SH-3), SH-4, SH-5, SH-6
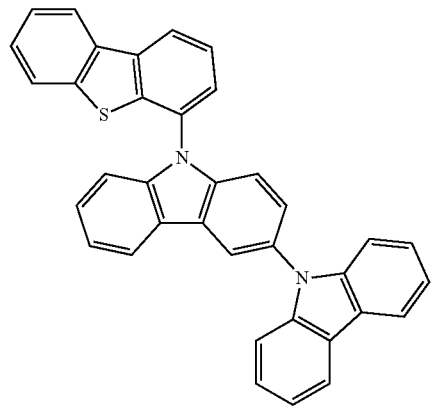
(SH-7)
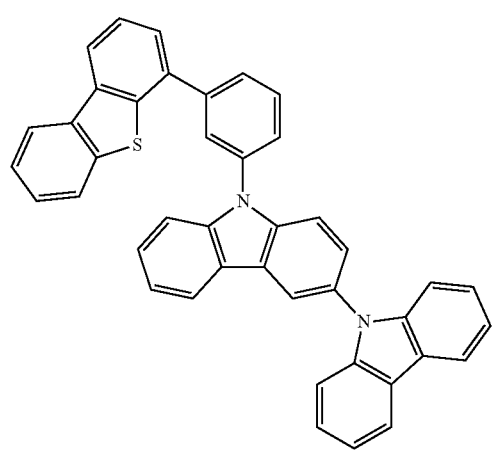
(SH-8)
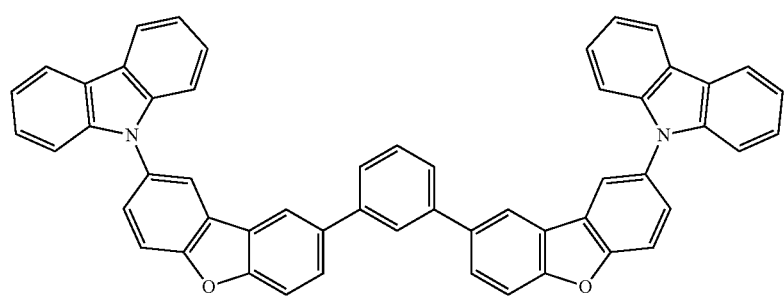
(SH-9)

(SH-10)

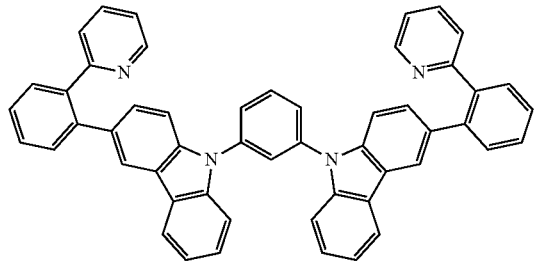

and (SH-11)

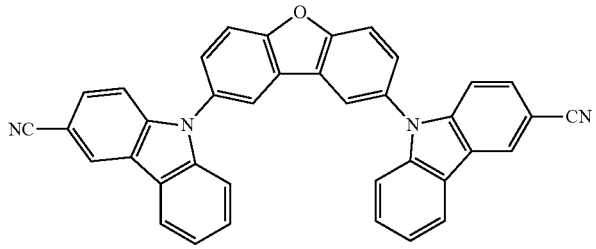

are most preferred.

TADF Material

In a further embodiment of the present invention, the compounds of formula I are employed as TADF material in the light-emitting layer of an OLED. The compounds of formula I are used as TADF emitter or as TADF host materials in combination with fluorescent emitters.

Suitable host materials in combination with the compounds of formula I as emitter material as well as suitable fluorescent emitter material in combination with the compounds of formula I as TADF host material are known by a person skilled in the art.

Hole/Exciton Blocking Layer (f):

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer.

Additional hole blocker materials typically used in OLEDs are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato) aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]-phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO2009/003919 and WO2009003898 and disilyl compounds as disclosed in WO2008/034758, as a blocking layer for holes/excitons (f).

In another preferred embodiment compounds (SH-1), (SH-2), (SH-3), SH-4, SH-5, SH-6, (SH-7), (SH-8), (SH-9), (SH-10) and (SH-11) may be used as hole/exciton blocking materials.

Electron Transport Layer (g):

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

It is likewise possible to use mixtures of at least two materials in the electron-transporting layer, in which case at least one material is electron-conducting. Preferably, in such mixed electron-transport layers, at least one phenanthroline compound is used, preferably BCP, or at least one pyridine compound according to the formula (XVI) below, preferably a compound of the formula (XVIa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula XVII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP1786050, or with compounds described in EP1837926B1, EP1837927, EP2246862 and WO2010132236.

In a preferred embodiment, the electron-transport layer comprises at least one compound of the general formula (XVII)

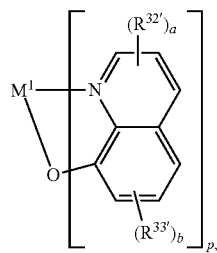

in which $R^{32'}$ and $R^{33'}$ are each independently F, $C_1$-$C_8$-alkyl, or $C_6$-$C_{14}$-aryl, which is optionally substituted by one or more $C_1$-$C_8$-alkyl groups, or two $R^{32'}$ and/or $R^{33'}$ substituents together form a fused benzene ring which is optionally substituted by one or more $C_1$-$C_8$-alkyl groups;

a and b are each independently 0, or 1, 2 or 3, $M^1$ is an alkaline metal atom or alkaline earth metal atom, p is 1 when $M^1$ is an alkali metal atom, p is 2 when $M^1$ is an earth alkali metal atom.

A very particularly preferred compound of the formula (XVII) is

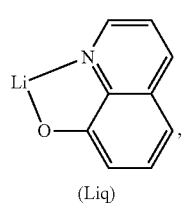

(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (XVI),

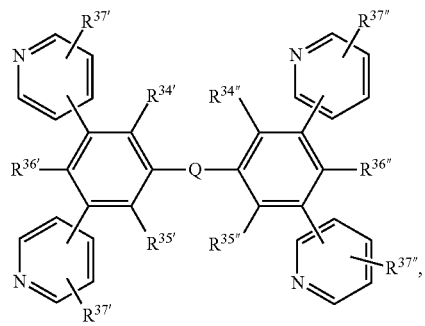

(XVI)

in which $R^{34''}$, $R_{35'''}$, $R^{36''}$, $R^{37''}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E' and/or interrupted by D', $C_6$-$C_{24}$-aryl, $C_6$-$C_{24}$-aryl which is substituted by G', $C_2$-$C_{20}$-heteroaryl or $C_2$-$C_{20}$-heteroaryl which is substituted by G', Q is an arylene or heteroarylene group, each of which is optionally substituted by G';

D' is —CO—; —COO—; —S—; —SO—; —$SO_2$—; —O—; —$NR^{40'}$—; —$SiR^{45'}R^{46'}$—; —$POR^{47'}$—; —$CR^{38'}$=$CR^{39'}$—; or —C≡C—;

E' is —$OR^{44'}$; —$SR^{44'}$; —$NR^{40'}R^{41'}$; —$COR^{43'}$; —$COOR^{42'}$; —$CONR^{40'}R^{41'}$; —CN; or F;

G' is E', $C_1$-$C_{18}$-alkyl, $C_1$-$C_{18}$-alkyl which is interrupted by D', $C_1$-$C_{18}$-perfluoroalkyl, $C_1$-$C_{18}$-alkoxy, or $C_1$-$C_{18}$-alkoxy which is substituted by E' and/or interrupted by D', in which $R^{38'}$ and $R^{39'}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40'}$ and $R^{41'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40'}$ and $R^{41'}$ together form a 6-membered ring;

$R^{42'}$ and $R^{43'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44'}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R_{45'}$ and $R^{46'}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47'}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (XVI) are compounds of the formula (XVIa)

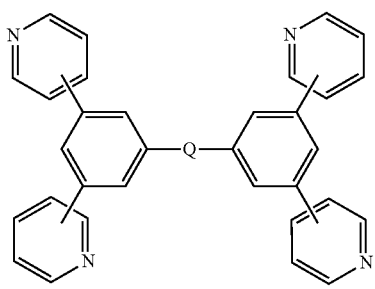
(XVIa)

in which Q is:

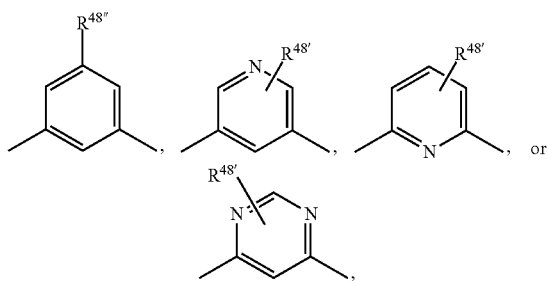, or

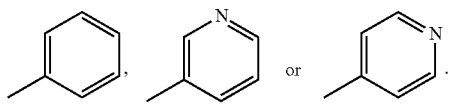, $R^{48'}$ is H or $C_1$-$C_{18}$-alkyl and
$R^{48''}$ is H, $C_1$-$C_{18}$-alkyl or

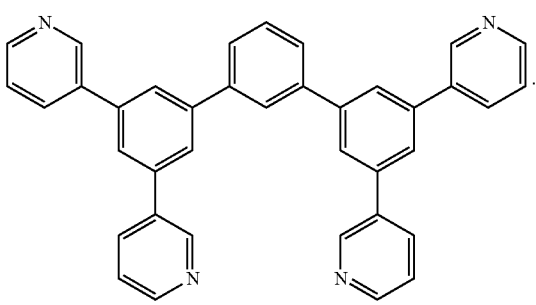

Particular preference is given to a compound of the formula

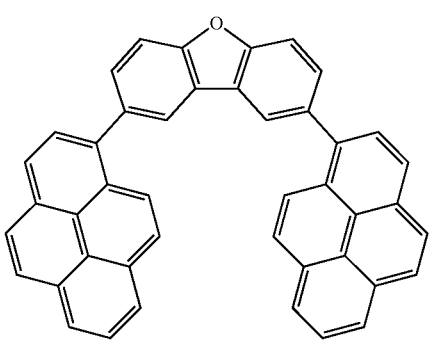 [SMILES: c1cc2ccc3ccc(-c4ccc5oc6ccc(-c7ccc8ccc9cccc%10ccc7c8c9%10)cc6c5c4)c4ccc(c1)c2c34]
(ETM-2)

In a further, very particularly preferred embodiment, the electron-transport layer comprises a compound Liq and a compound ETM-2.

In a preferred embodiment, the electron-transport layer comprises at least one compound of the formula (XVII) in an amount of 99 to 1% by weight, preferably 75 to 25% by weight, more preferably about 50% by weight, and at least one compound of the formula (XVI) in an amount of 1 to 99% by weight, preferably 25 to 75% by weight, more preferably about 50% by weight, where the amount of the compounds of the formulae (XVII) and the amount of the compounds of the formulae (XVI) adds up to a total of 100% by weight The preparation of the compounds of the formula (XVI) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound (A-10; =ETM-1) is most preferred.

In a preferred embodiment, the electron-transport layer comprises Liq in an amount of 99 to 1% by weight, preferably 75 to 25% by weight, more preferably about 50% by weight, and at least one dibenzofuran compound in an amount of 1 to 99% by weight, preferably 25 to 75% by weight, more preferably about 50% by weight, where the amount of Liq and the amount of the dibenzofuran compound(s), especially ETM-1, adds up to a total of 100% by weight In a preferred embodiment, the electron-transport layer comprises at least one phenanthroline derivative and/or pyridine derivative.

In a further preferred embodiment, the electron-transport layer comprises at least one phenanthroline derivative and/or pyridine derivative and at least one alkali metal hydroxyquinolate complex.

In a further preferred embodiment, the electron-transport layer comprises at least one of the dibenzofuran compounds A-1 to A-36 and B-1 to B-22 described in WO2011/157790, especially ETM-1.

In a further preferred embodiment, the electron-transport layer comprises a compound described in WO2012/111462, WO2012/147397, WO2012014621, such as, for example, a compound of formula

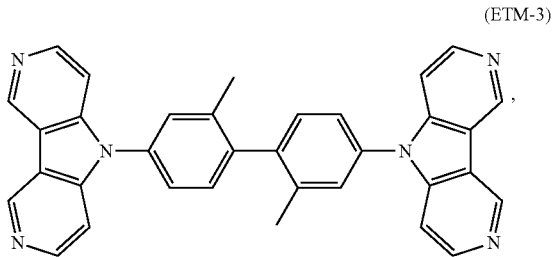 [SMILES: Cc1cc(-n2c3ccncc3c3cnccc32)ccc1-c1ccc(-n2c3ccncc3c3cnccc32)cc1C]

US2012/0261654, such as, for example, a compound of formula

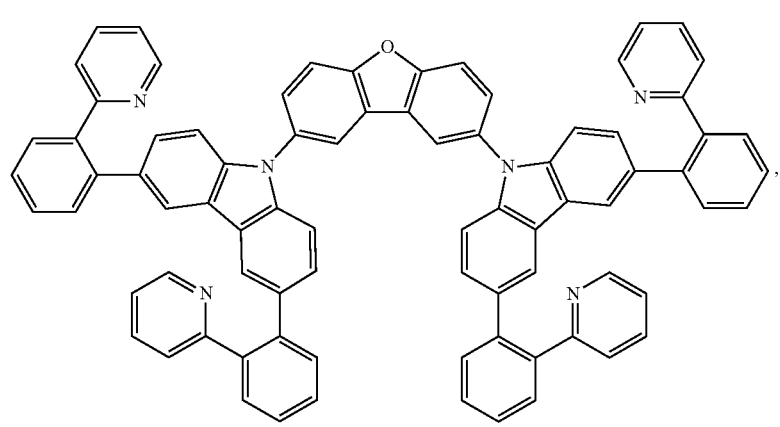

and WO2012/115034, such as for example, such as, for example, a compound of formula

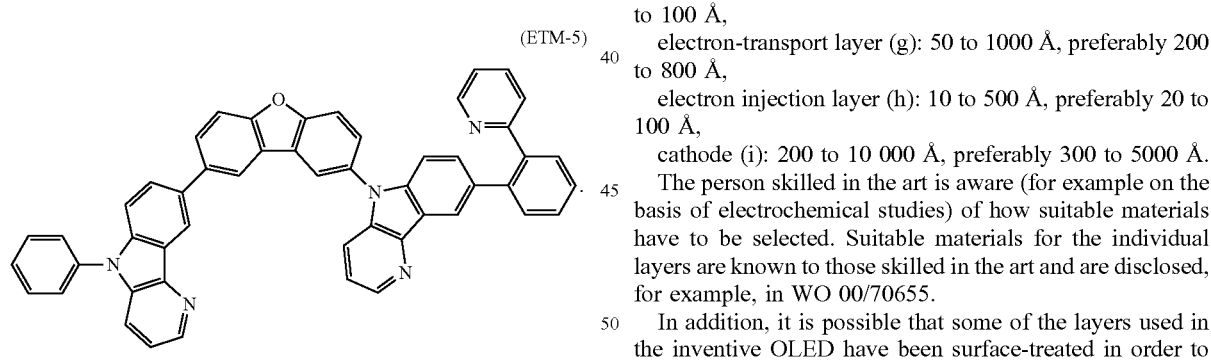

Electron Injection Layer (h):

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i):

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:

anode (a): 500 to 5000 Å (ångström), preferably 1000 to 2000 Å;
hole injection layer (b): 50 to 1000 Å, preferably 200 to 800 Å,
hole-transport layer (c): 50 to 1000 Å, preferably 100 to 800 Å,
exciton blocking layer (d): 10 to 500 Å, preferably 50 to 100 Å,
light-emitting layer (e): 10 to 1000 Å, preferably 50 to 600 Å,
hole/exciton blocking layer (f): 10 to 500 Å, preferably 50 to 100 Å,
electron-transport layer (g): 50 to 1000 Å, preferably 200 to 800 Å,
electron injection layer (h): 10 to 500 Å, preferably 20 to 100 Å,
cathode (i): 200 to 10 000 Å, preferably 300 to 5000 Å.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

Use of the compounds of the formula I in at least one layer of the OLED, preferably in the light-emitting layer (preferably as a matrix material), charge transport layer and/or in the charge/exciton blocking layer makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

I Preparation Examples

Example 1

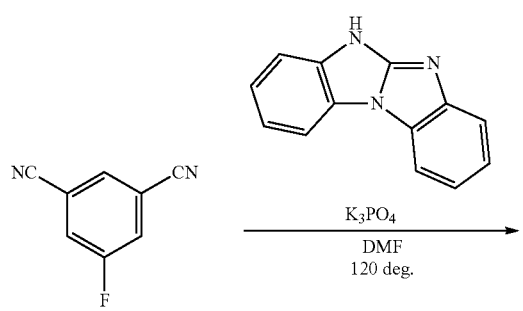

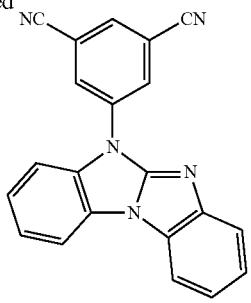

2.92 g (20.0 mmol) of 1,3-dicyano-5-fluoro-benzene, 4.14 g (20.0 mmol) of 6H-benzimidazolo[1,2-a]benzimidazole and 4.25 g (20.0 mmol) of tripotassium phosphate in 50 ml of DMF are stirred for 2 h at 120° C. The reaction mixture is cooled at room temperature and added water, then the precipitate is filtered off. Gradient column chromatography on silica gel with dichloromethane/ethyl acetate (dichloromethane 100%, 9/1, 4/1) gives the product. Yield 6.13 g (92%).

$^1$H NMR (400 MHz, CDCl$_3$): δ 8.61 (d, 2H); 7.96 (t, 1H); 7.89 (td, 2H); 7.83 (dd, 1H); 7.66 (dd, 1H); 7.52 (td, 1H); 7.49-7.43 (m, 2H); 7.40 (td, 1H).

Example 2

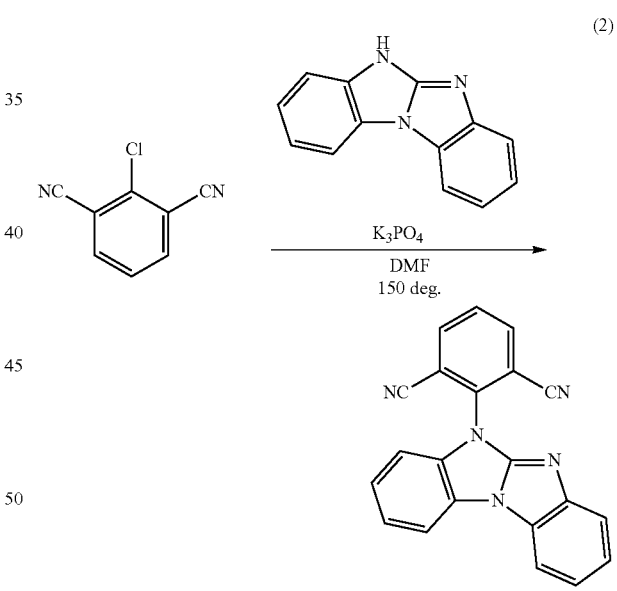

1.63 g (10.0 mmol) of 2-chloro-1,3-dicyano-benzene, 2.07 g (10.0 mmol) of 6H-benzimidazolo[1,2-a]benzimidazole and 2.12 g (10.0 mmol) of tripotassium phosphate in 50 ml of DMF are stirred for 24 h at 150° C. The reaction mixture is cooled at room temperature and added water, then the precipitate is filtered off. Gradient column chromatography on silica gel with dichloromethane/ethyl acetate (dichloromethane 100%, 9/1, 4/1) gives the product. Yield 2.80 g (84%).

$^1$H NMR (400 MHz, CDCl$_3$): δ 8.19 (d, 2H); 7.95-7.87 (m, 2H); 7.86 (t, 1H); 7.79 (dd, 1H); 7.49 (td, 1H); 7.46-7.35 (m, 3H); 7.15 (dt, 1H).

Example 3

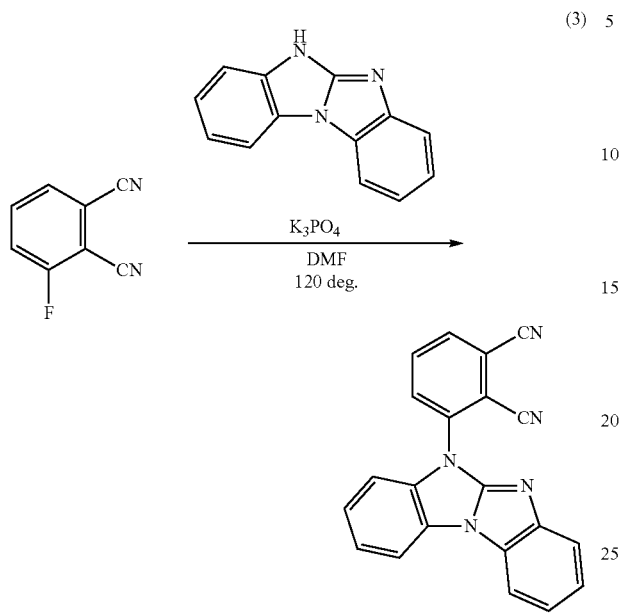

1.46 g (10.0 mmol) of 1,2-dicyano-3-fluoro-benzene, 2.07 g (10.0 mmol) of 6H-benzimidazolo[1,2-a]benzimidazole and 2.12 g (10.0 mmol) of tripotassium phosphate in 50 ml of DMF are stirred for 24 h at 120° C. The reaction mixture is cooled at room temperature and added water, then the precipitate is filtered off. Gradient column chromatography on silica gel with dichloromethane/ethyl acetate (dichloromethane 100%, 9/1, 4/1) gives the product. Yield 3.10 g (93%).

$^1$H NMR (400 MHz, CDCl$_3$): δ 8.20 (dd, 1H); 8.05-7.96 (m, 2H); 7.90 (dd, 2H); 7.79 (dd, 1H); 7.49 (td, 1H); 7.46-7.36 (m, 3H); 7.32-7.26 (m, 1H).

Example 4

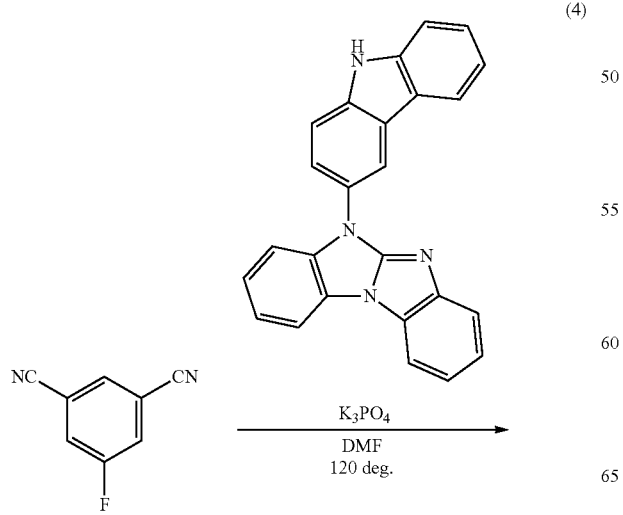

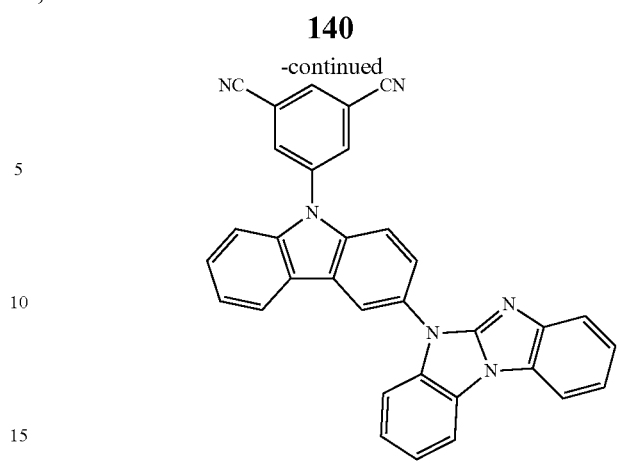

0.98 g (6.71 mmol) of 1,3-dicyano-5-fluoro-benzene, 2.50 g (6.71 mmol) of 6-(3-carbazolyl)-benzimidazolo[1,2-a]benzimidazole and 1.42 g (6.71 mmol) of tripotassium phosphate in 20 ml of DMF are stirred for 24 h at 120° C. The reaction mixture is cooled at room temperature and added water, then the precipitate is filtered off. Gradient column chromatography on silica gel with dichloromethane/ethyl acetate (dichloromethane 100%, 9/1, 4/1) gives the product. Yield 2.94 g (88%).

$^1$H NMR (400 MHz, CDCl$_3$): δ 8.56 (dd, 1H); 8.24 (d, 2H); 8.23-8.19 (m, 1H); 8.07 (t, 1H); 7.94-7.89 (m, 3H); 7.81 (dt, 1H); 7.62 (dd, 1H); 7.60-7.53 (m, 2H); 7.48-7.32 (m, 6H).

Example 5

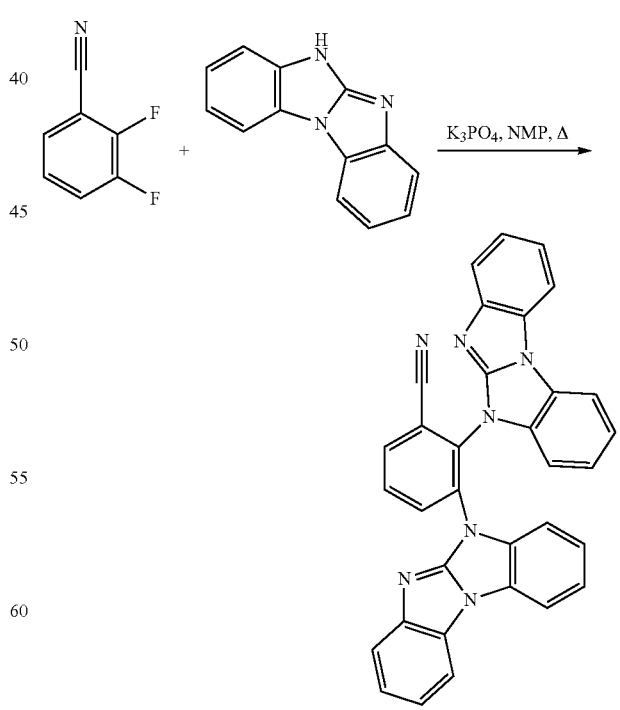

5.00 g (36.0 mmol) 2,3-difluorobenzonitrile, 14.9 g (72.0 mmol) 6H-benzimidazolo[1,2-a]benzimidazole and 30.5

(144 mmol) potassium phosphate tribasic in 120 ml NMP (N-Methyl-2-pyrrolidon) are stirred at 185° C. under nitrogen for 6 h.

The reaction mixture is filtered hot and the organic phase is poured on water. The product is filtered of. Column chromatography on silica gel with chloroform gives 6.25 g 33.9% of the product.

$^1$H NMR (300 MHz, DMSO-D6): rotamers: δ 8.43-8.57 (m, 2H), 7.58-8.20 (m, 6H), 6.86-7.42 (m, 9H), 6.63-7.78 (m, 1H), 6.48-6.54 (m, 1H).

Example 6

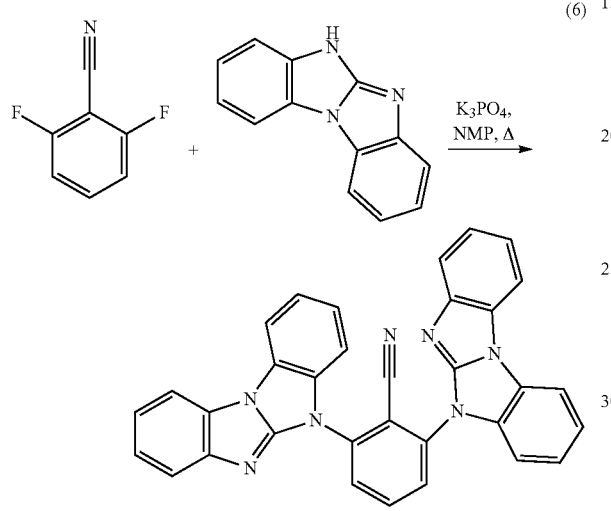

(6)

5.00 g (36.0 mmol) 2,6-difluorobenzonitrile, 14.9 g (72.0 mmol) 6H-benzimidazolo[1,2-a]benzimidazole and 30.5 g (144 mmol) potassium phosphate tribasic in 150 ml NMP (N-Methyl-2-pyrrolidon) are stirred at 170° C. under nitrogen for 6 h. The reaction mixture is filtered hot and the precipitated product was filtered of. The product is decocted in DMSO. Yield 3 g 16.3% of the product.

$^1$H NMR (400 MHz, TFA-d1): δ 8.48-8.78 (m, 3H), 8.24-8.32 (m, 4H), 7.67-7.93 (m, 12H).

Example 7

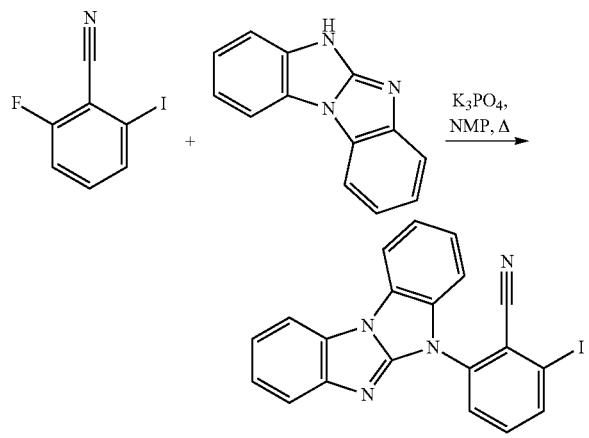

A.) 10.6 g (41.6 mmol) 2-bromo-6-fluoro-benzonitrile, 8.63 g (41.6 mmol) 6H-benzimidazolo[1,2-a]benzimidazole and 30.9 (146 mmol) potassium phosphate tribasic in 70 ml NMP (N-Methyl-2-pyrrolidon) are stirred at 115° C. under nitrogen for 2 h. The reaction mixture is filtered hot and the or organic phase is poured on water. The product is filtered of. Yield 17 g (94%).

$^1$H NMR (300 MHz, DMSO-D6): δ 8.22-8.34 (m, 3H), 8.02-8.05 (m, 1H), 7.69-7.79 (m, 1H), 7.60-7.65 (m, 1H), 7.30-7.50 (m, 5H)

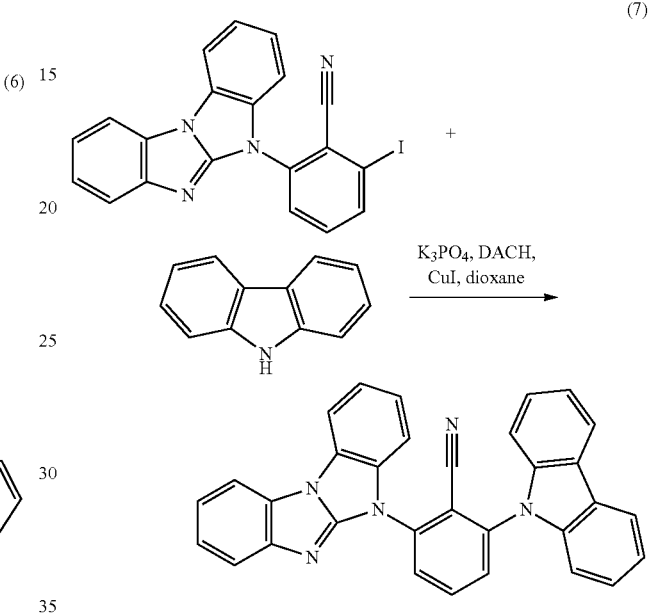

(7)

B.) 6.52 g (15.0 mmol) 2-(benzimidazolo[1,2-a]benzimidazol-5-yl)-6-iodo-benzonitrile, 2.51 g (15.0 mmol) carbazole, 12.8 g (60.0 mmol) potassium phosphate tribasic, 0.430 g (2.00 mmol) cupper(I) iodide and 4.00 g (35.0 mmol) DACH ((±)-trans-1,2-diaminocyclohexane) in 75 ml mml dioxane are stirred at 95° C. under nitrogen for 24 h.

The reaction mixture is filtered hot and the solids are washed with dioxane. The solvent is removed in vacuum. Column chromatography on silica gel with chloroform gives 1.53 g 22% of the product.

$^1$H NMR (300 MHz, DMSO-D6): δ 8.25-8.34 (m, 6H), 8.08-8.11 (m, 1H), 7.31-7.70 (m, 12H) MS (ESI(pos), m/z): 474 (M$^{+1}$).

Example 8

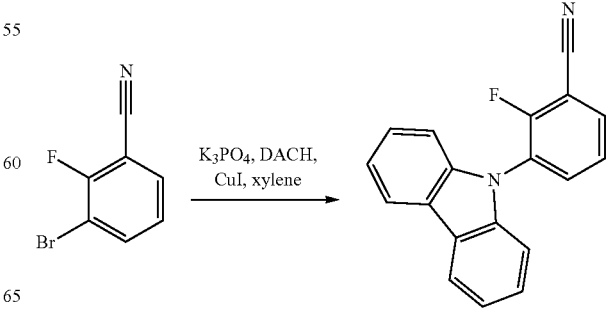

A.) 15.0 g 3-bromo-2-fluoro-benzonitrile (75.0 mmol), 12.9 g (77.0 mmol) carbazole, 47.8 g (225 mmol) potassium phosphate tribasic, 1.43 g (7.00 mmol) cupper(I) iodide and 1.71 g (15.0 mmol) DACH ((±)-trans-1,2-diaminocyclohexane) in 150 ml xylene are stirred at 115° C. under nitrogen for 20 h.

The reaction mixture is filtered hot and the solids are washed with Xylene. The solvent is removed in vacuum. Column chromatography on silica gel with chloroform/heptane 1 to 1 gives 5.7 g 27% of the product.

$^1$H NMR (300 MHz, DMSO-D6): δ 8.29 (s, 1H), 8.27 (s, 1H), 8.13-8.20 (m, 1H), 7.67-7.73 (m, 1H), 7.44-7.50 (m 2H), 7.29-7.37 (m 4H)

B.) 3.50 g (12.2 mmol) 3-carbazol-9-yl-2-fluoro-benzonitrile, 2.58 g (12.5 mmol) 6H-benzimidazolo[1,2-a]benzimidazole and 10.3 g (50 mmol) potassium phosphate tribasic in 35 ml NMP (N-Methyl-2-pyrrolidon) are stirred at 170° C. under nitrogen for 18 h.

The reaction mixture is filtered hot and the precipitated product was filtered of. Column chromatography on silica gel with dichloromethane gives 1.70 g 29% of the product.

$^1$H NMR (300 MHz, DMSO-D6): δ 8.46 (dd, 1H), 8.29 (dd. 1H), 8.13 (t, 1H), 7.96-8.00 (m, 2H), 7.85 (d, 1H), 7.80 (d, 1H), 7.67 (d, 1H), 7.58 (d, 1H), 7.41-7.46 (m, 1H), 7.31-7.37 (m, 1H) 7.22-7.27 (m, 2H), 7.00-7.707 (m, 2H), 6.87-6.93 (m, 2H), 6.66-6.73 (m, 2H).

MS (ESI(pos), m/z): 474 (M$^{+1}$).

Example 9

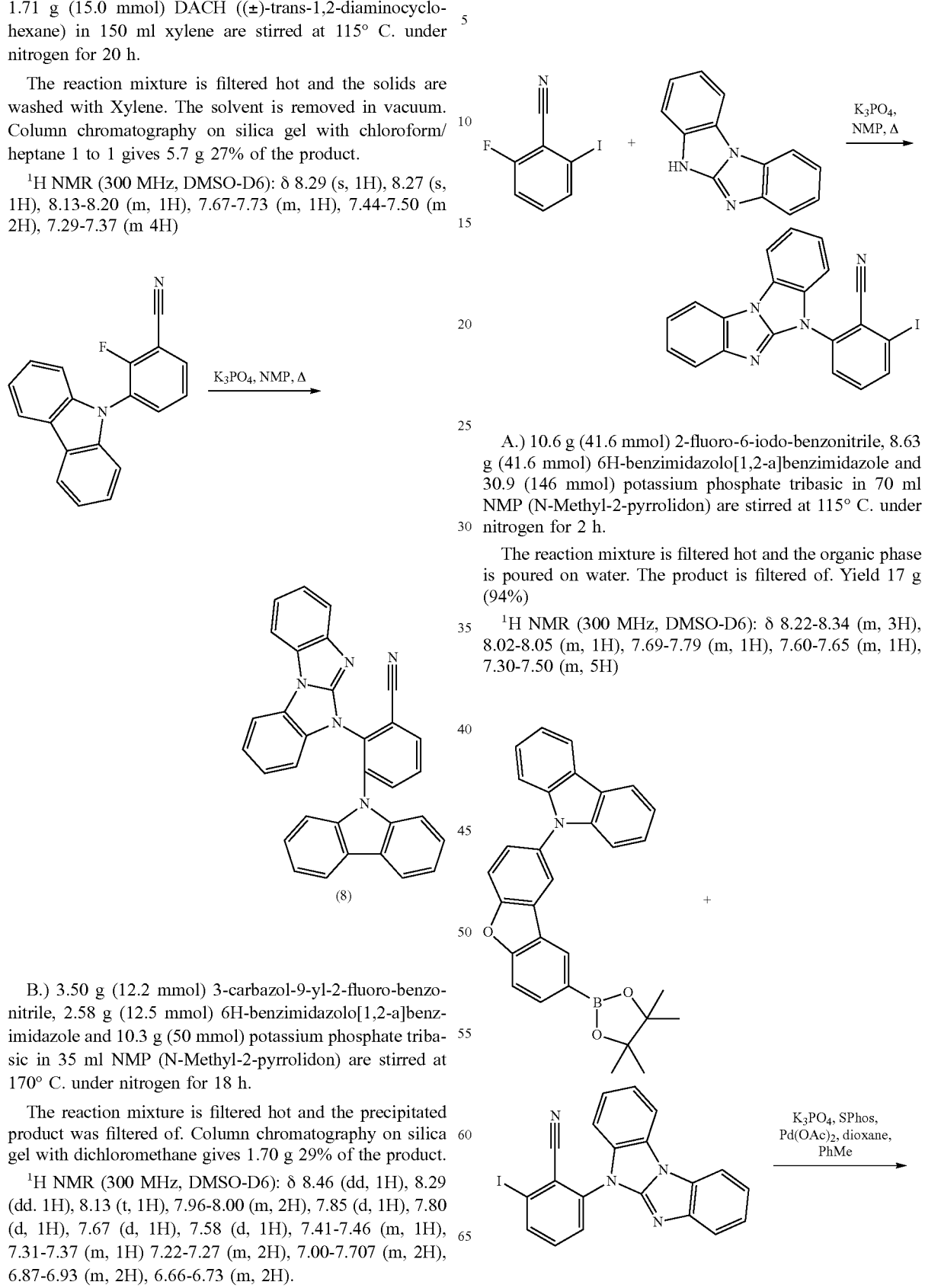

A.) 10.6 g (41.6 mmol) 2-fluoro-6-iodo-benzonitrile, 8.63 g (41.6 mmol) 6H-benzimidazolo[1,2-a]benzimidazole and 30.9 (146 mmol) potassium phosphate tribasic in 70 ml NMP (N-Methyl-2-pyrrolidon) are stirred at 115° C. under nitrogen for 2 h.

The reaction mixture is filtered hot and the organic phase is poured on water. The product is filtered of. Yield 17 g (94%)

$^1$H NMR (300 MHz, DMSO-D6): δ 8.22-8.34 (m, 3H), 8.02-8.05 (m, 1H), 7.69-7.79 (m, 1H), 7.60-7.65 (m, 1H), 7.30-7.50 (m, 5H)

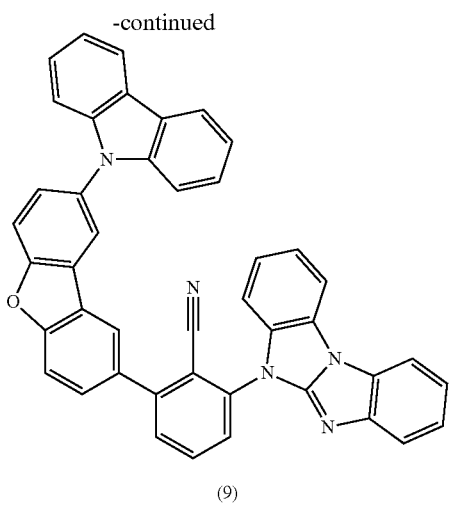

(9)

B.) 4.20 g (9.67 mmol) 2-(benzimidazolo[1,2-a]benzimidazol-5-yl)-6-iodo-benzonitrile, 4.44 g (9.67 mmol) 9-[8-(4,4,5,5-tetramethyl-1,3,2-dioxaborolan-2-yl)dibenzofuran-2-yl]carbazole, 8.21 g (39.0 mmol) potassium phosphate tribasic in 30 ml dioxane, 60 ml toluene and 24 ml water are degased with argon. 0.2 g (0.9 mmol) palladium(II)acetate is added and the reaction mixture is degased with argon. 0.93 g (2.2 mmol) SPhos (2-Dicyclohexylphosphino-2',6'-dimethoxybiphenyl) is added and the reaction mixture is degased with argon. The reaction mixture is refluxed under argon for 18 h.

The organic layer is washed with a 1% solution of NaCN in water and then the organic phase is washed with water. The organic phase is dried with Magnesium sulfate and the solvent is removed in vacuum.

Column chromatography on silica gel with dichloromethane gives 1.450 g 23% of the product.

¹H NMR (300 MHz, DMSO-D6): δ 8.58-8.71 (m, 2H), 7.78-8.31 (m, 11H), 7.59-7.65 (m, 1H), 7.25-7.50 (m, 11H)
MS (APCI(pos), m/z): 640 (M⁺¹).

Example 10

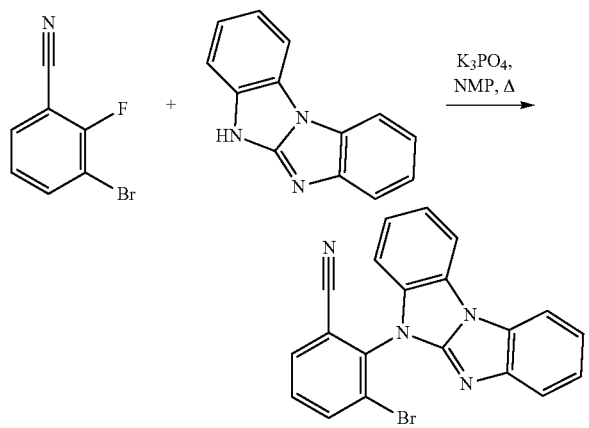

A.) 15.0 g (75.0 mmol) 3-bromo-2-fluoro-benzonitrile, 15.5 g (75 mmol) 6H-benzimidazolo[1,2-a]benzimidazole and 47.8 (225 mmol) potassium phosphate tribasic in 100 ml NMP (N-Methyl-2-pyrrolidon) are stirred at 105° C. under nitrogen for 3.5 h.

The reaction mixture is filtered hot and the organic phase is poured on water. The product is filtered of. Yield 26.4 g (91%)

¹H NMR (300 MHz, DMSO-D6): δ 8.37-8.41 (m, 1H), 8.27-8.32 (m, 3H), 7.83-7.88 (t, 1H, J=2*8 Hz), 7.60-7.66 (m, 1H), 7.25-7.53 (m, 5H)

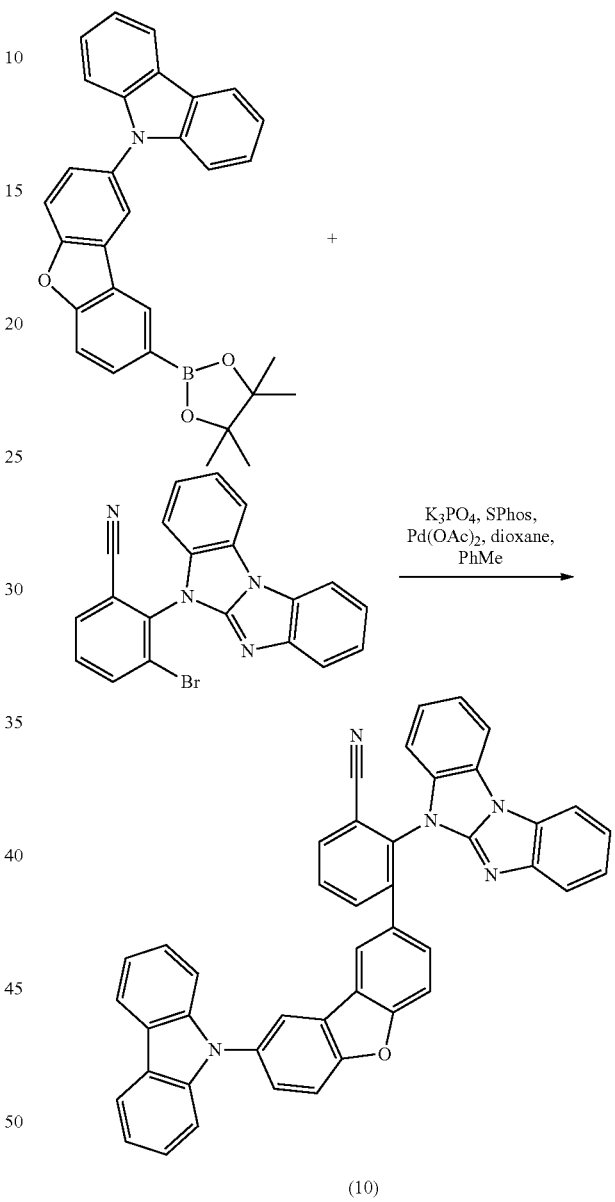

(10)

B.) 5.00 g (12.9 mmol) 2-(benzimidazolo[1,2-a]benzimidazol-5-yl)-3-bromo-benzonitrile, 5.93 g (12.9 mmol) 9-[8-(4,4,5,5-tetramethyl-1,3,2-dioxaborolan-2-yl)dibenzofuran-2-yl]carbazole, 11.0 g (52.0 mmol) potassium phosphate tribasic in 32 ml dioxane, 80 ml toluene and 24 ml water are degased with argon. 0.1 g (0.5 mmol) palladium(II)acetate is added and the reaction mixture is degased with argon. 0.46 g (1 mmol) SPhos (2-Dicyclohexylphosphino-2',6'-dimethoxybiphenyl) is added and the reaction mixture is degased with argon. The reaction mixture is refluxed under argon for 18 h.

The organic layer is washed with a 1% solution of NaCN in water and then the organic phase is washed with water.

The organic phase is dried with Magnesium sulfate and the solvent is removed in vacuum.

Column chromatography on silica gel with dichloromethane gives 3 g 36% of the product.

$^1$H NMR (300 MHz, DMSO-D6): δ 7.98-8.32 (m, 9H), 7.87-7.90 (d, 1H), 7.67-7.70 (dd, 1H), 7.03-7.55 (m, 14H),

Example 11

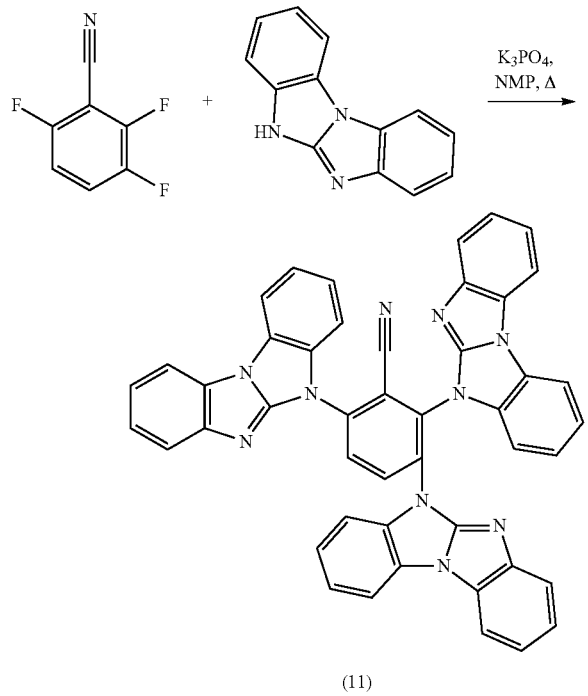

(11)

5.00 g (31.8 mmol) 3-bromo-2-fluoro-benzonitrile, 23.1 g (111 mmol) 6H-benzimidazolo[1,2-a]benzimidazole and 60.8 (0.286 mol) potassium phosphate tribasic in 120 ml NMP (N-Methyl-2-pyrrolidon) are stirred at 30° C. under nitrogen for 30 min. Then the reaction mixture is stirred at 120° C. for 4 h.

The reaction mixture is filtered hot and is washing with water. The product is crystalized from DMSO. The product is filtered of. Yield 2.5 g (11%)

$^1$H NMR (300 MHz, DMSO-D6): δ 6.44-8.33 (m, 26H)

Example 12

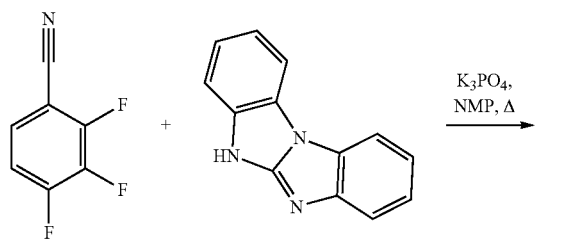

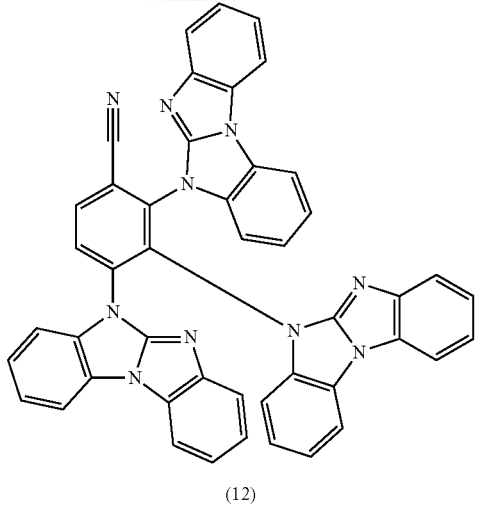

(12)

2.5 g (15.9 mmol) 2,3,4-trifluorobenzonitrile, 10.9 g (52.5 mmol) 6H-benzimidazolo[1,2-a]benzimidazole and 27.0 g (0.127 mol) potassium phosphate tribasic in 50 ml NMP (N-Methyl-2-pyrrolidon) are stirred at 115° C. under nitrogen for 18 h. The reaction mixture is filtered hot and the organic phase is poured on water. The product is filtered of. Column chromatography on silica gel with chloroform gives 1.3 g (11.4%) of the product $^1$H NMR (300 MHz, DMSO-D6): rotamers: δ 8.55-8.82 (m, 2H); 6.41-8.07 (m, 24H)

MS (APCI(pos), m/z): 719 (M$^{+1}$).

Example 13

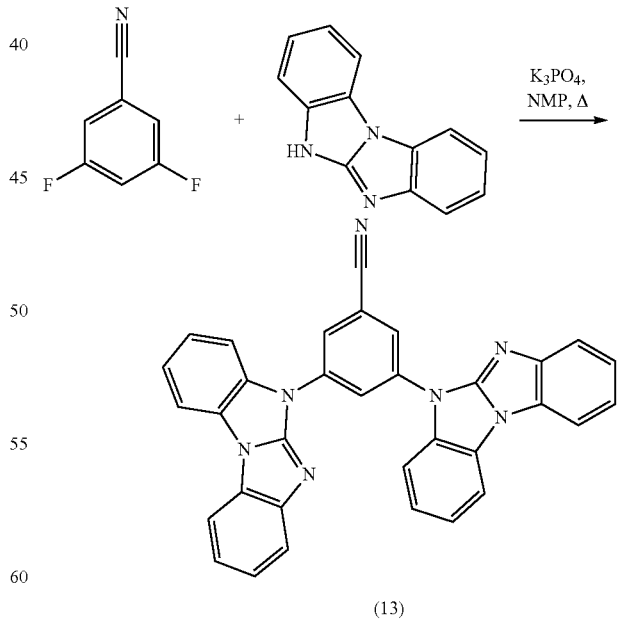

(13)

4.0 g (28.8 mmol) 3,5-difluorobenzonitrile, 11.9 g (57.6 mmol) 6H-benzimidazolo[1,2-a]benzimidazole and 36.6 g (173 mmol) potassium phosphate tribasic in 50 ml NMP (N-Methyl-2-pyrrolidon) are stirred at 180° C. under nitrogen for 7 h. The reaction mixture is filtered hot. Washing with water. Yield 6.6 g 47.7% product $^1$H NMR (400 MHz, TFA-d1): δ 8.87 (m, 1H); 8.70 (s, 1H); 8.69 (s, 1H); 8.28 (d, J=8.1 Hz 2H) 8.21-8.23 (m, 2H); 7.75-7.90 (m, 8H)

Example 14

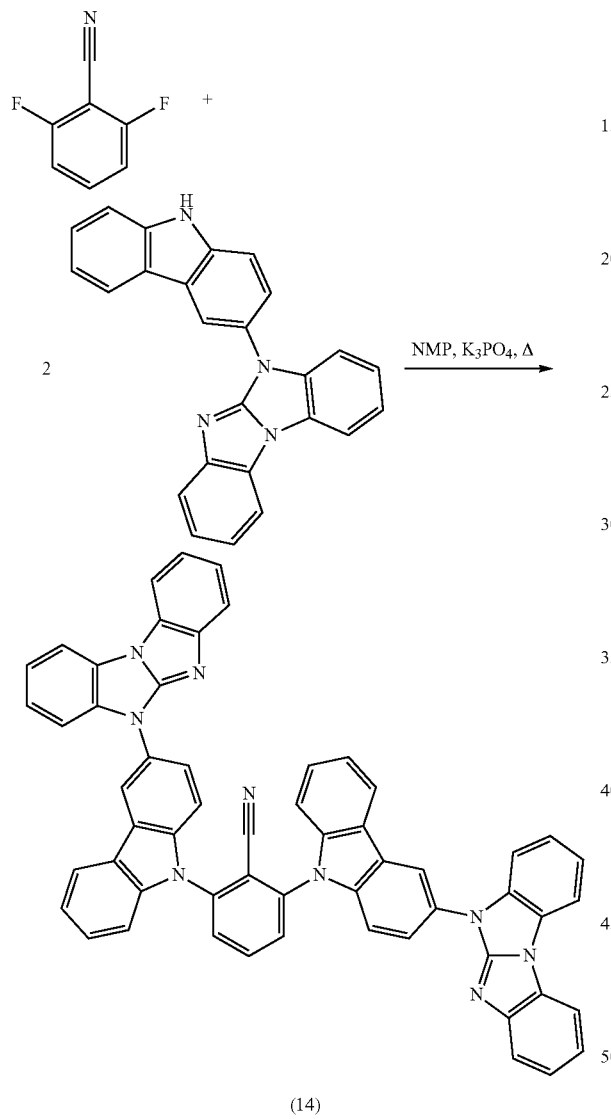

(14)

1.50 g (10.7 mmol) 2,6-difluorobenzonitrile, 8.19 g (22.0 mmol) 5-(9H-carbazol-3-yl)-5H-benzo[d]benzo[4,5]imidazo[1,2a]imidazole and 10.7 g (47.5 mmol) potassium phosphate tribasic in 30 ml NMP (N-Methyl-2-pyrrolidon) are stirred at 130° C. under nitrogen for 7 h. The reaction mixture is filtered hot and the organic phase is poured on water. The product is filtered of. Column chromatography on silica gel with chloroform gives 4.7 g (51.6%) of the product.

$^1$H NMR (400 MHz, DMSO-D6): δ 8.80-8.81 (d, 2H), 8.38-8.45 (m, 3H), 8.21-8.32 (m, 6H), 8.01-8.03-7.50 (t, 1H), 7.99-8.00 (t, 1H), 7.82-7.83 (d, 1H), 7.80-7.81 (d, 1H), 7.59-7.65 (m, 8H), 7.27-7.48 (m, 10H)

Example 15

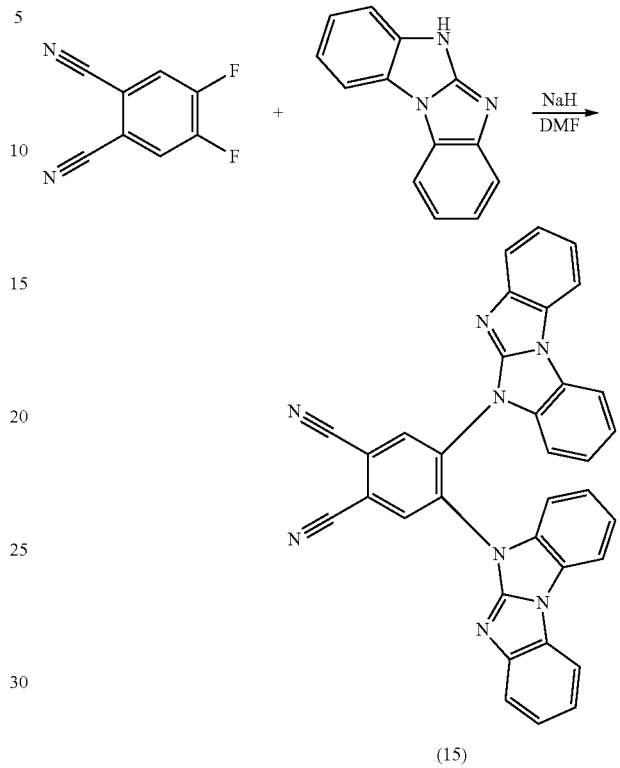

(15)

222 mg NaH (60% in mineral oil) and 304 mg (1.85 mmol) 4,5-difluorophtalonitril is added to a solution of 960 mg (4.63 mmol) benzimidazolo[1,2-a]benzimidazole in 275 ml N,N-dimethylformamide and stirred 1.5 hours at room temperature. The reaction is quenched with 550 ml distilled water, the precipate is filtered, washed three times with distilled water, and dried under vacuum at 60° C. The product is purified under chromatography using a 19:1 CH$_2$Cl$_2$/THF mixture and obtained as a fine bright yellow powder (99.6% purity, 886 mg, 89% yield). 1H-NMR (DMSO; 500 MHz): δ (ppm) 9.05 (d, 2H); 7.99 (d, 1H); 7.9 (m, 2H); 7.80 (d, 1H); 7.51 (d, 1H); 7.23 (m, 7H); 7.00 (m, 3H); 6.785 (t, 1H).

Example 16

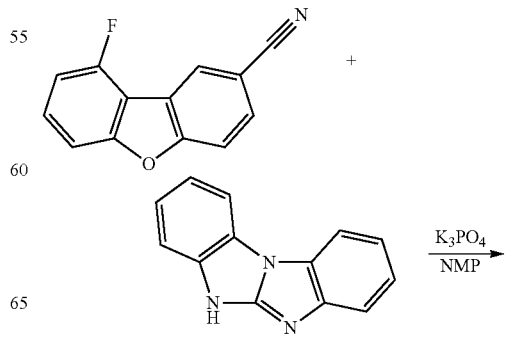

-continued

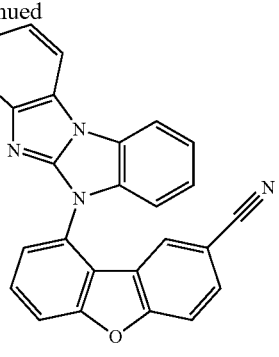

(16)

9-fluorodibenzofuran-2-carbonitrile (1.6 g, 7.58 mmol), 6H-benzimidazolo[1,2-a]benzimidazole (1.65 g, 7.96 mmol), and potassium phosphate (3.38 g, 15.91 mmol) are suspended in 39 mL of NMP, and the mixture is stirred at 185° C. for 14 h. After the reaction mixture is cooled at room temperature, it is diluted with 76 mL of water and 38 mL of EtOH. The solid is collected by filtration, and dried in vacuum oven at 50° C. The crude product is purified by column chromatography on silica gel eluting with chloroform to yield 2.21 g (73%) of 9-(benzimidazolo[1,2-a] benzimidazol-5-yl)dibenzofuran-2-carbonitrile as a white solid.

$^1$H-NMR (300 MHz, DMSO-d$_6$): δ 8.36-8.26 (m, 2H), 8.08-7.83 (m, 5H), 7.61-7.54 (m, 2H), 7.48 (td, J=1.1, 7.8 Hz, 4H), 7.36-7.30 (m, 3H), 7.19 (d, J=7.8 Hz, 1H)

Example 17

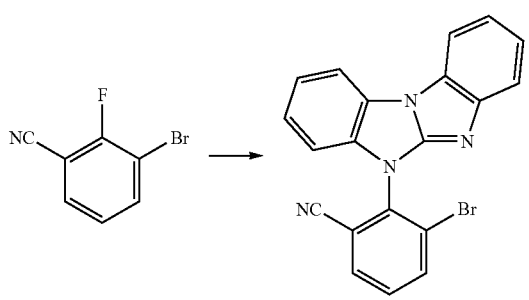 [SMILES: N#Cc1cccc(Br)c1F ; N#Cc1cccc(Br)c1-n1c2ccccc2n2c3ccccc3nc12]

A.) 10 g (50.0 mmol) 3-bromo-4-fluoro-benzonitrile, 9.33 g (45 mmol) 6H-benzimidazolo[1,2-a]benzimidazole and 31.8 g (150 mmol) K$_3$PO$_4$ are added to 100 ml DMF and the suspension is heated to 110° C. for 23 h. The reaction mixture is filtered hot through Hyflo and the filtrate is evaporated on the rotavap to yield 18.6 g of crude product. The crude product is suspended in 100 ml MeOH, stirred at RT for 2 h, filtered and dried at 80° C./125 mbar overnight to yield 15.1 g of a beige product. Recrystallization from 500 ml EtOAc yields 13.5 g (69.7% of theory) 2-(benzimidazolo[1,2-a]benzimidazol-5-yl)-3-bromo-benzonitrile as white solid.

$^1$H-NMR (400 MHz, CDCl$_3$): δ 8.08 (dxd, J$_1$=8.4 Hz, J$_2$=1.6 Hz, 1H), 7.90-7.865 (m, 3H), 7.76 (d, J=7.6 Hz, 1H), 7.57 (t, J=8.0 Hz, 1H), 7.44-7.30 (m, 4H), 7.01 (d, J=8.0 Hz, 1H)

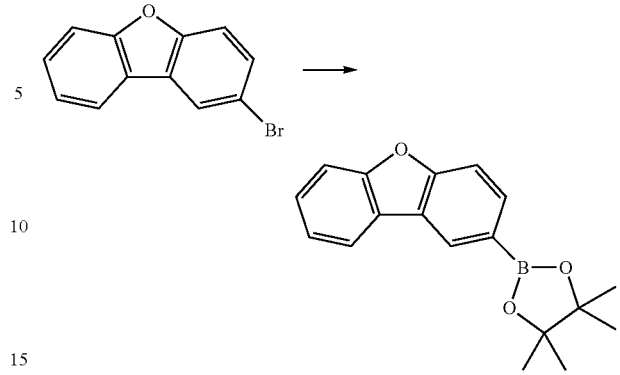

B.) 40 g (160.3 mmol) 2-bromo-dibenzofuran are dissolved in 250 ml THF abs. and cooled to −78° C. 65 ml (175.5 mmol) BuLi (2.7M in hexane) are added within 55 min while keeping the internal temperature below −73° C. The resulting suspension is stirred for 30 min followed by the addition of 33.5 g (176.3 mmol) 2-isopropoxy-4,4,5,5-tetramethyl-1,3,2-dioxaborolane within 30 min while keeping the internal temperature below −73° C. The reaction mixture is then slowly brought to RT, then 200 ml of buffer solution pH=7 are added and the pH brought to 7 by the addition of HCl 4M. The organic solvent is then evaporated on the rotavap; the aqueous phase is extracted three times with EtOAc (250 ml each). The combined organic phases are washed three times with H$_2$O (200 ml each), dried over Na$_2$SO$_4$, filtered and evaporated. The crude product (51.7 g) is purified by CombiFlash chromatography (solvent: Heptane/CH$_2$Cl$_2$ (0 to 40%)) to yield 34.1 g of a colorless oil. 100 ml MeOH are added, the mixture is heated to reflux, cooled to RT and then to 0° C. The suspension is filtered and the residue is dried at 30° C./125 mbar overnight to yield 28.3 g (60.0% of theory) 2-dibenzofuran-2-yl-4,4,5,5-tetramethyl-1,3,2-dioxaborolane as a white solid.

$^1$H-NMR (300 MHz, CDCl$_3$): 8.45 (s (1H), 7.99-7.92 (m. 2H), 7.59-7.55 (m, 2H), 7.48 (t, J=7.2 Hz, 1H), 7.37 (t, J=7.8 Hz, 1H), 1.40 (s, 12H).

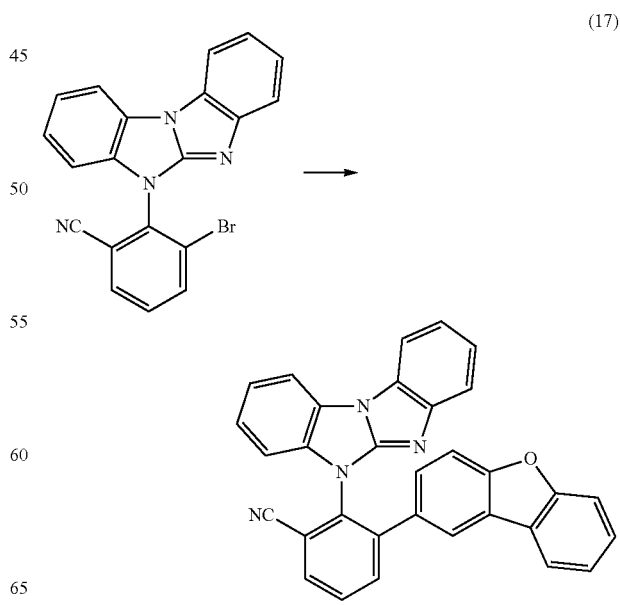

(17)

C.) 7.68 g (19.8 mmol) 2-(benzimidazolo[1,2-a]benzimidazol-5-yl)-3-bromo-benzonitrile and 7.0 g (23.8 mmol) 2-dibenzofuran-2-yl-4,4,5,5-tetramethyl-1,3,2-dioxaborolane are dissolved in 140 ml THF and the solution is evacuated and purged three times with argon. 0.35 g (1.2 mmol) P(t-Bu)$_3$.HBF$_4$ and 0.54 g (0.6 mmol) Pd$_2$(dba)$_3$ are added and the solution is evacuated and purged three times with argon and heated to 50° C. A solution of 12.6 g (59.5 mmol) K$_3$PO$_4$ in 35 ml H$_2$O (evacuated and purged three times with argon) is added with a syringe and the reaction mixture is heated to reflux for 17 h. To the cooled reaction mixture are added 300 ml EtOAc and the phases are separated. The organic phase is washed three times with brine (100 ml each), dried over MgSO$_4$ filtered and evaporated on the rotavap to yield 13.3 g of crude product. Flash chromatography using CH$_2$Cl$_2$/EtOAc=9:1 as eluent yields 7.23 g (68.0% of theory) 2-(benzimidazolo[1,2-a]benzimidazol-5-yl)-3-dibenzofuran-2-yl-benzonitrile as a white solid.

$^1$H-NMR (300 MHz, CDCl$_3$): δ 7.97 (m, 2H), 7.84-7.71 (m, 4H), 7.64 (d, J=7.6 Hz, 1H), 7.53 (d, J=8.0 Hz, 1H), 7.44 (d, J=8.0 Hz, 1H), 7.39-7.33 (m, 2H), 7.28-7.11 (m, 6H), 6.90 (d, J=7.6 Hz, 1H).

Example 18

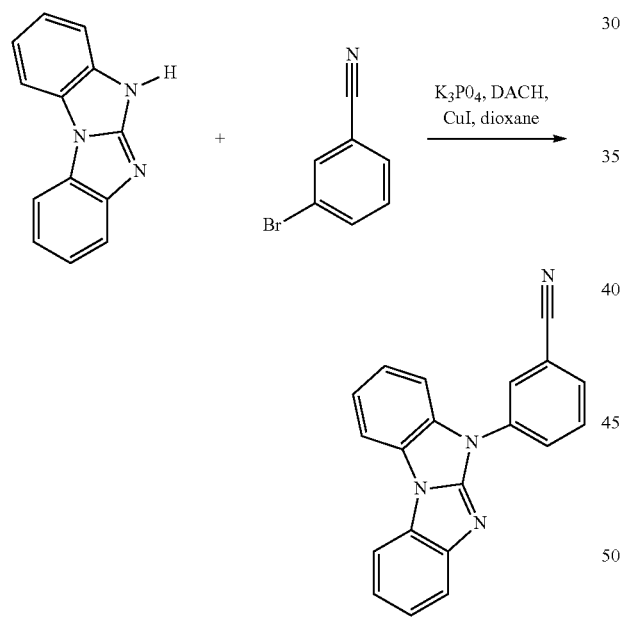

A.) 20.0 g (87.3 mmol) 3-bromo-benzonitrile, 16.6 g (80.0 mmol) 6H-benzimidazolo[1,2-a]benzimidazole, 67.9 g (320 mmol) potassium phosphate tribasic, 1.5 g (7.88 mmol) cupper(I) iodide and 100 g (875 mmol) DACH ((±)-trans-1,2-diaminocyclohexane) in 240 ml dioxane are stirred at 100° C. under nitrogen for 7 h.

The reaction mixture is filtered hot and the solids are washed with dioxane. The reaction mixture is cooled to 50° C. and the crystalized product is filtered of and is washed with methanol. Yield 11.2 g (46%)

$^1$H-NMR (300 MHz, CDCl$_3$): δ 7.33-7.49 (m, 4H), 7.59-7.63 (d, 1H), 7.72-7.83 (m, 3H), 7.86-7.90 (d, 2H), 8.22-8.26 (m, 2H),

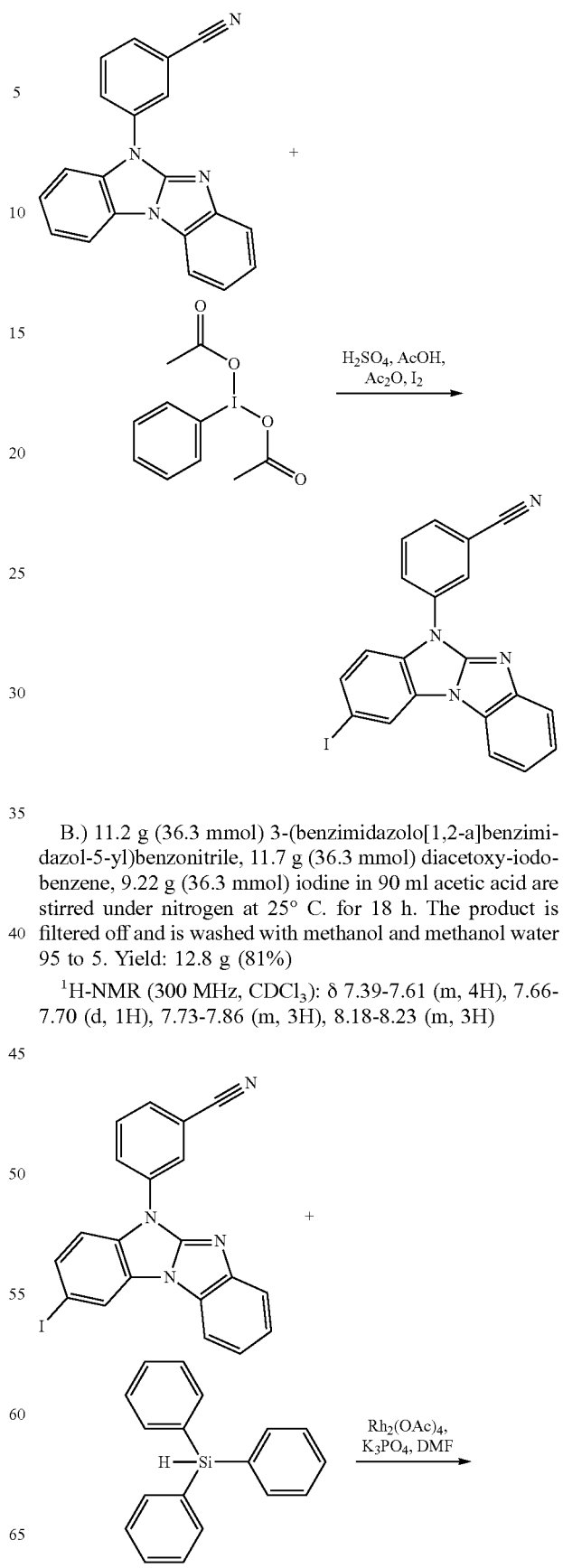

B.) 11.2 g (36.3 mmol) 3-(benzimidazolo[1,2-a]benzimidazol-5-yl)benzonitrile, 11.7 g (36.3 mmol) diacetoxy-iodobenzene, 9.22 g (36.3 mmol) iodine in 90 ml acetic acid are stirred under nitrogen at 25° C. for 18 h. The product is filtered off and is washed with methanol and methanol water 95 to 5. Yield: 12.8 g (81%)

$^1$H-NMR (300 MHz, CDCl$_3$): δ 7.39-7.61 (m, 4H), 7.66-7.70 (d, 1H), 7.73-7.86 (m, 3H), 8.18-8.23 (m, 3H)

-continued

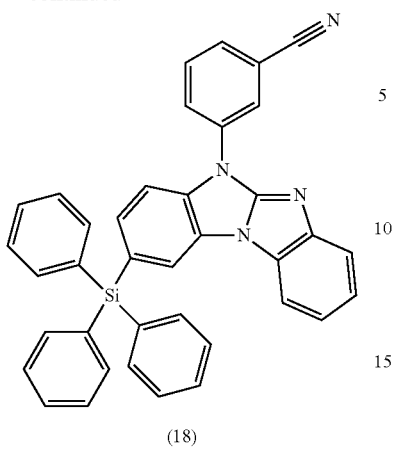

(18)

C.) To 10.0 g (20.7 mmol) 3-(2-iodobenzimidazolo[1,2-a]benzimidazol-5-yl)benzonitrile, 8.18 g (31.1 mmol) triphenylsilane, 17.6 g (82.9 mmol) potassium phosphate in 125 ml dimethylformamide is degassed with argon. 500 mg (1.131 mmol) Rhodium(II)-acetate is added and the reaction mixture is degassed with argon. The reaction mixture is stirred at 60° C. for 18 h under argon. 250 mg 500 mg (0.566 mmol) Rhodium(II)-acetate is added and the reaction mixture is stirred for 18 h under argon. The reaction is filtered and the filtrate is caped for crystallization. Column chromatography with chloroform gives the product. Yield 1.5 g (12.8%)

$^1$H-NMR (300 MHz, CDCl$_3$): δ 7.36-7.86 (m, 23H), 8.02 (s, 1H), 8.20-8.26 (m, 2H)

Example 19 (Comparative)

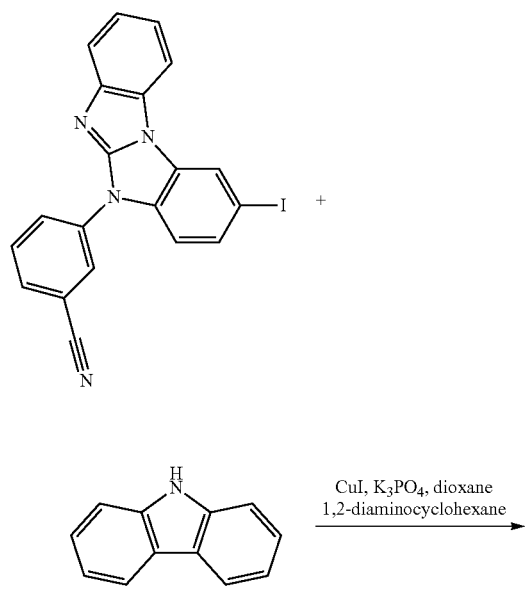

-continued

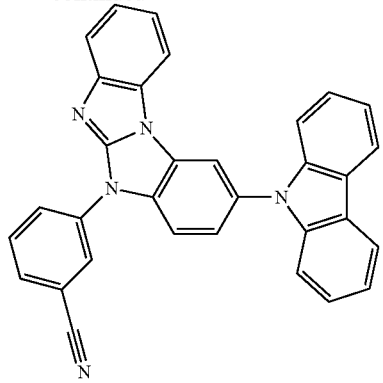

3.00 g (6.91 mmol) of 3-(2-iodobenzimidazolo[1,2-a]benzimidazol-5-yl)benzonitrile (see example 18), 1.39 g (8.29 mmol) carbazol, 4.40 g (20.7 mmol) potassium carbonate tribasic, 260 mg (1.38 mmol) copper iodide in 70 ml dioxane are stirred at 100° C. under nitrogen. 5.52 g (48.4 mmol) 1,2-diaminocyclohexne is added and the reaction mixture is stirred at 100° C. under nitrogen for 25 h.

The reaction mixture is poured on methanol and the product is filtered of. The product is washed with water and methanol. Column chromatography on silica gel with dichloromethane and 0.2% methanol give the product.

$^1$H-NMR (CDCl$_3$): d 8.29-8.26 (m, 2H), 8.24-8.21 (m, 2H), 8.04 (d, 1H), 7.99 (d, 1H), 7.85-7.77 (m, 3H), 7.65-7.58 (m, 2H), 7.48-7.40 (m, 6H), 7.37-7.32 (m, 2H).

II Application Examples

Comparative Application Example 1

A glass substrate with 120 nm-thick indium-tin-oxide (ITO) transparent electrode used as an anode is first cleaned with isopropanol in an ultrasonic bath for 10 min. To eliminate any possible organic residues, the substrate is exposed to an ultraviolet light and ozone for further 30 min. This treatment also improves the hole injection properties of the ITO. The cleaned substrate is mounted on a substrate holder and loaded into a vacuum chamber. Thereafter, the organic materials specified below are applied by vapor deposition to the ITO substrate at a rate of approx. 0.2-1 Å/sec at about $10^{-6}$-$10^{-8}$ mbar. As a hole injection layer, compound

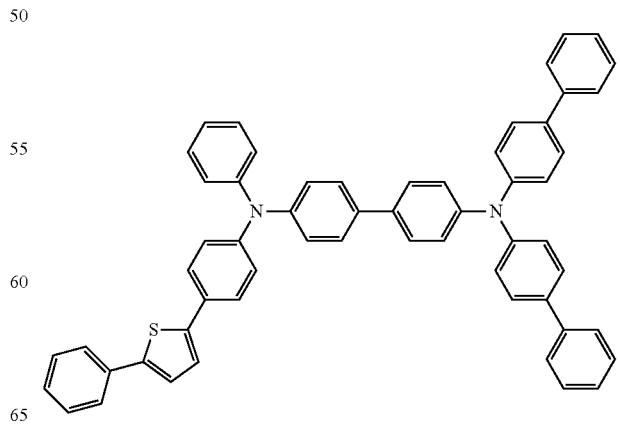

with 30 nm thickness is applied. Then compound

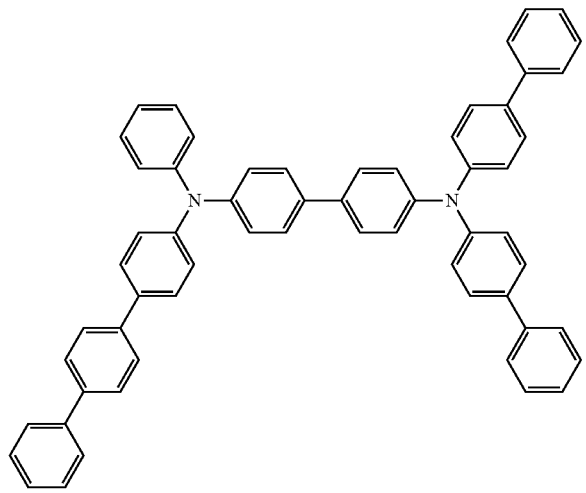 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

with 60 nm thickness is applied as a hole transporting layer. As an exciton and electron blocker, compound

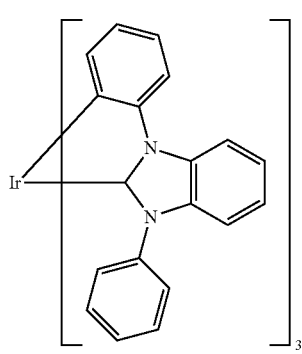

(HTM-1; for preparation, see Ir complex (7) in the application WO2005/019373) is then applied with a thickness of 10 nm. Subsequently, a mixture of 20% by weight of emitter compound,

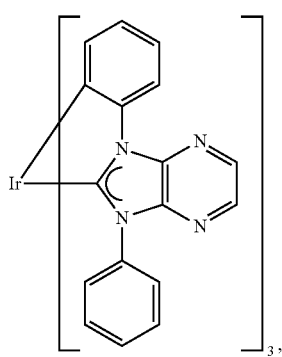

(BE-1)

15% by weight of compound (HTM-1) and 65% by weight of host (SH-1)

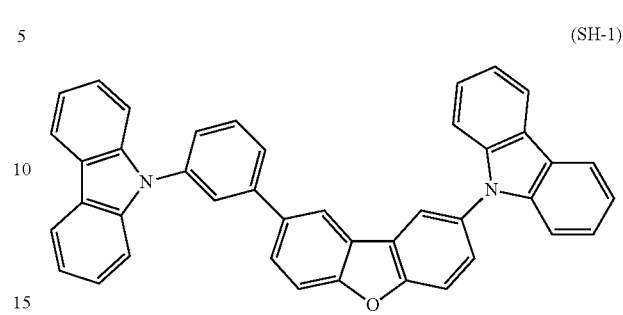

are applied to form a 40 nm-thick emitting layer. On the emitting layer, 5 nm-thick material (SH-1) is applied as an exciton blocker. Thereafter, compound

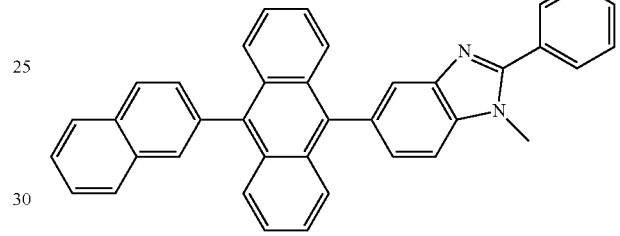

with 20 nm thickness is deposited as an electron transport layer. Finally, 1 nm-thick LiF is deposited as an electron injection layer and 80 nm-thick Al is then deposited as a cathode to complete the device. The device is sealed with a glass lid and a getter in an inert nitrogen atmosphere with less than 1 ppm of water and oxygen.

OLED Characterization

To characterize the OLED, electroluminescence spectra are recorded at various currents and voltages. In addition, the current-voltage characteristic is measured in combination with the luminance to determine luminous efficiency and external quantum efficiency (EQE). Driving voltage U and EQE are given at luminance (L)=1000 cd/m² except otherwise stated.

Application Example 1 (Inventive)

Comparative Application Example 1 is repeated except that the host (SH-1) is replaced by compound (Compound (13))

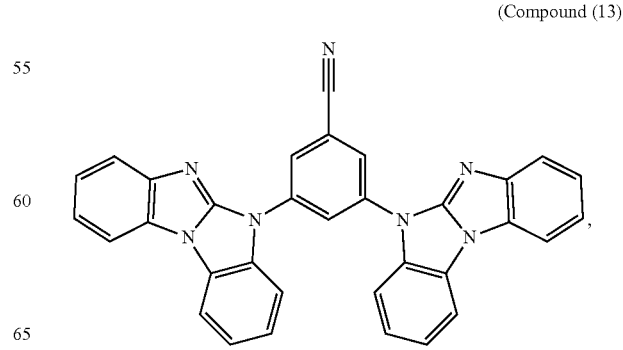

preparation Example 13). The device results are shown in Table 1.

Application Example 2 (Inventive)

Comparative Application Example 1 is repeated except that the host (SH-1) is replaced by compound (Compound (5))

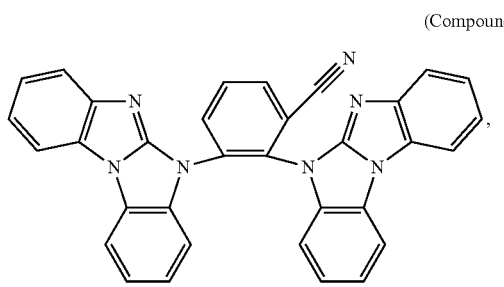

preparation Example 5). The device results are shown in Table 1.

Application Example 3 (Inventive)

Comparative Application Example 1 is repeated except that both the host (SH-1) and exciton blocker (SH-1) are replaced by compound (Compound (5))

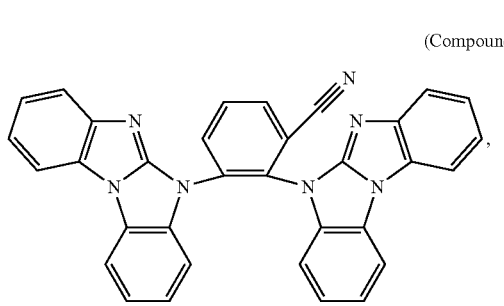

preparation Example 5). The device results are shown in Table 1.

TABLE 1

| Appl. Ex. | Host | Exciton blocker | U [V] | Luminous efficiency [lm/W] |
|---|---|---|---|---|
| Comp. Appl. Ex. 1 | (SH-1) | (SH-1) | 5.46 | 17.7 |
| Appl. Ex. 1 | (13) | (SH-1) | 4.83 | 19.3 |
| Appl. Ex. 2 | (5) | (SH-1) | 4.55 | 22.7 |
| Appl. Ex. 3 | (5) | (5) | 4.18 | 23.0 |

The results shown in Table 1 demonstrate that the driving voltage U is significantly reduced with increasing luminous efficiency at the same time when compounds (5) or (13) is used as the host instead of reference compound (SH-1). Furthermore, when compound (5) is used as both the host and exciton blocker, the driving voltage U is further reduced and the luminous efficiency is also improved.

Comparative Application Example 2

A glass substrate with 120 nm-thick ITO is cleaned and treated in the same manner as comparative application example 1. As a hole injection layer, compound

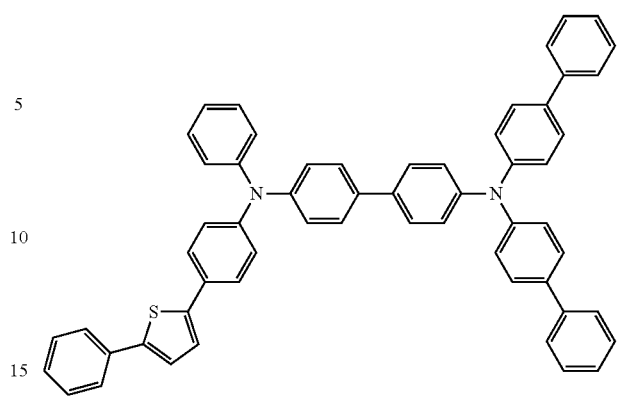

with 30 nm thickness is applied by vapor deposition. Then 60 nm of compound (SH-1) doped with MoOx (~10%) is deposited as hole transporting layer. MoOx is used to improve the hole conductivity of SH-1. As an exciton and electron blocker, compound (SH-1) is applied with a thickness of 10 nm. Subsequently, a mixture of 20% by weight of emitter compound (BE-1) and 80% by weight of host (SH-1) are applied to form a 40 nm of emitting layer. On the emitting layer, 5 nm of material (SH-1) is applied as an exciton blocker. Thereafter, compound

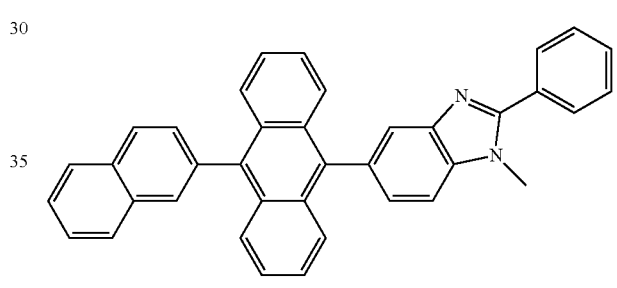

with 20 nm thickness is deposited as an electron transport layer. Finally, 1 nm of LiF is deposited as an electron injection layer and 80 nm of Al is then deposited as a cathode to complete the device. The device is sealed with a glass lid and a getter in an inert nitrogen atmosphere with less than 1 ppm of water and oxygen.

Application Example 4 (Inventive)

Comparative Application Example 2 is repeated except that both the host (SH-1) and exciton blocker (SH-1) is replaced by compound (Compound (6))

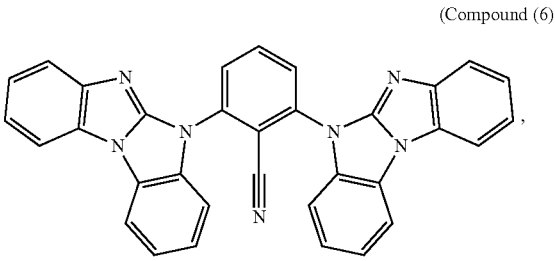 [SMILES: N#Cc1c(-n2c3ccccc3n3c4ccccc4nc23)cccc1-n1c2ccccc2n2c3ccccc3nc12]

preparation Example 6). The device results are shown in Table 2.

Application Example 5 (Inventive)

Comparative Application Example 2 is repeated except that both the host (SH-1) and exciton blocker (SH-1) is replaced by compound (Compound (5))

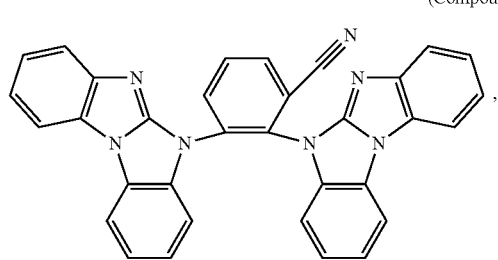

preparation Example 5). The device results are shown in Table 2.

TABLE 2

| Appl. Ex. | Host | Exciton blocker | U [V] | Luminous efficiency [lm/W] |
|---|---|---|---|---|
| Comp. Appl. Ex. 2 | (SH-1) | (SH-1) | 5.54 | 1.2 |
| Appl. Ex. 4 | (6) | (6) | 4.52 | 23.3 |
| Appl. Ex. 5 | (5) | (5) | 3.87 | 27.1 |

The results shown in Table 2 demonstrate that the driving voltage and the luminous efficiency are improved when compounds (5) or (6) are used as host and exciton blocker instead of reference compound (SH-1).

The invention claimed is:
1. A compound of formula (Ia):
(I)

(Ia)

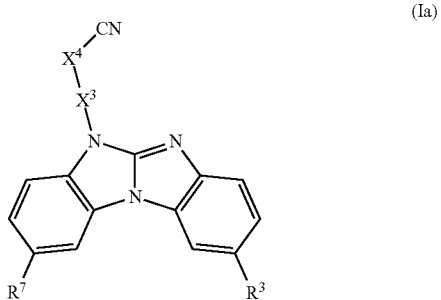

wherein:
$R^3$, $R^7$ are independently of each other H or a group of the following formula:

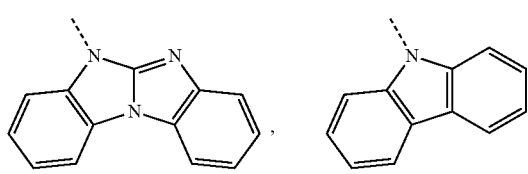

or $-SiR^{70}R^{71}R^{72}$,
$X^3$ is a single bond
$X^4$ is

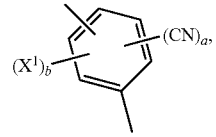

XI a is 0, 1, 2, 3 or 4,
b is 1, 2, 3 or 4,
$X^1$ is a group of formula $-(A^1)_o-(A^2)_p-(A^3)_q-(A^4)_r-R_{10}$,
$A^1$, $A^2$, $A^3$, $A^4$ are in each occurrence independently of each other $C_6-C_{24}$ arylene group which is unsubstituted or substituted by at least one group G, $C_2-C_{30}$ heteroarylene group which is unsubstituted or substituted by at least one group G,
in each occurrence o is 0 or 1, p is 0 or I, q is 0 or 1, r is 0 or 1;
$R^{10}$ is H,

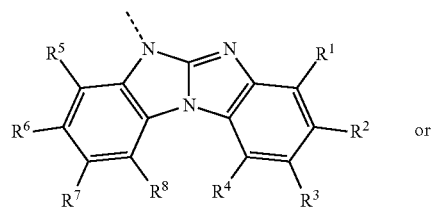

III

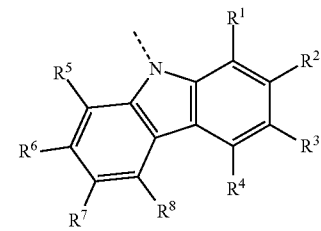

or

IV

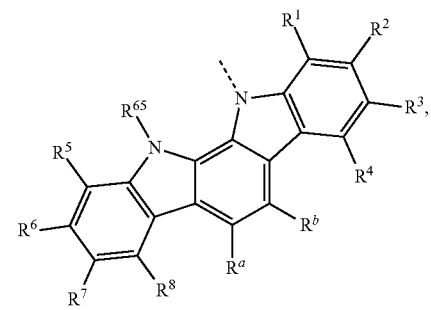

V

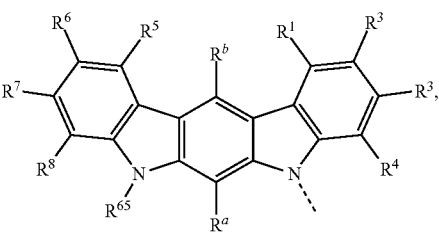

VI

-continued

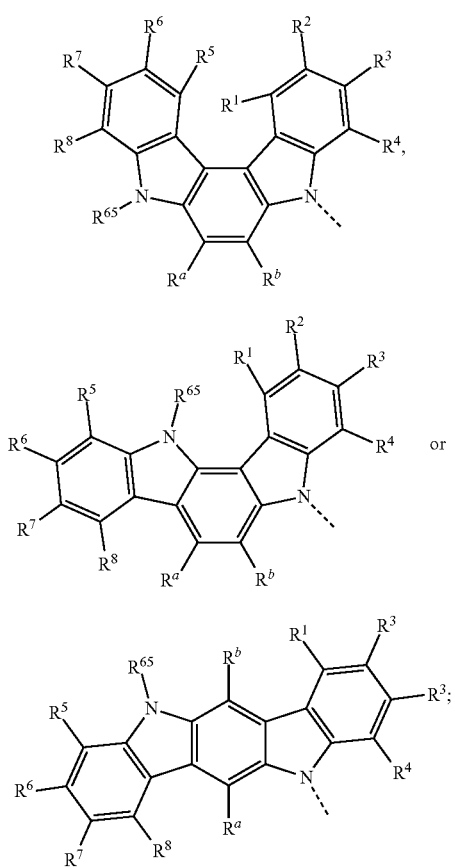

VII

VIII

IX wherein when each of o, p, q and r are 0, $R^{10}$ is not H, $R^1$, $R^2$, $R^3$, $R^4$, $R^5$, $R^6$, $R^7$, $R^8$, $R^9$, $R^a$ and $R^b$ are in each occurrence independently H, $C_6$-$C_{24}$ aryl group which is unsubstituted or substituted by at least one group G, $C_2$-$C_{30}$ heteroaryl group which is unsubstituted or substituted by at least one group G, a $C_1$-$C_{25}$alkyl group, which is unsubstituted or substituted by at least one group E and/or interrupted by D, $C_6$-$C_{24}$ aryloxy group which is unsubstituted or substituted by at least one group G, or —SiR$^{70}$R$^{71}$R$^{72}$; or two groups $R^1$ and $R^2$ or $R^2$ and $R^3$ or $R^3$ and $R^4$ of formulae IV can form together the following ring system:

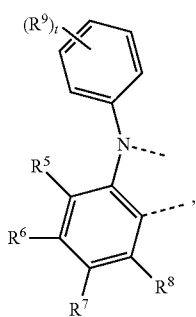

wherein t is 1 to 5;
D is —CO—, —COO—, —S—, —SO—, —SO$_2$—, —O—, —CR$^{63}$=CR$^{64}$—, —NR$^{65}$—, —SiR$^{70}$R$^{71}$—, —POR$^{72}$—, or —C≡C—, E is —OR$^{69}$, —SR$^{69}$, —NR$^{65}$R$^{66}$, —COR$^{68}$, —COOR$^{67}$, —CONR$^{65}$R$^{66}$, —CN, —SiR$^{70}$R$^{71}$R$^{72}$, halogen, an unsubstituted $C_6$-$C_{24}$aryl group, a $C_6$-$C_{24}$aryl group, which is substituted by F, $C_1$-$C_{18}$alkyl, $C_1$-$C_{18}$alkyl which is interrupted by O, an unsubstituted $C_2$-$C_{30}$heteroaryl group, or a $C_2$-$C_{30}$heteroaryl group, which is substituted by F, $C_1$-$C_{18}$alkyl, $C_1$-$C_{18}$alkyl which is interrupted by —O—;

G is E, or a $C_1$-$C_{18}$alkyl group, or $C_1$-$C_{18}$alkyl which is interrupted by O, $R^{63}$ and $R^{64}$ are independently of each other $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl.

2. A compound as claimed in claim 1, wherein:
a is 0, 1,2 or 3,
b is 1, 2 or 3,
the sum of a+b is 1, 2 or 3.

3. A compound as claimed in claim 1, wherein in each occurrence o is 0 or 1, p is 0 or 1, and q and r are 0.

4. A compound as claimed in claim 1, wherein:
$A^1$, $A^2$, $A^3$, $A^4$ are in each occurrence independently of each other a group of the formula:

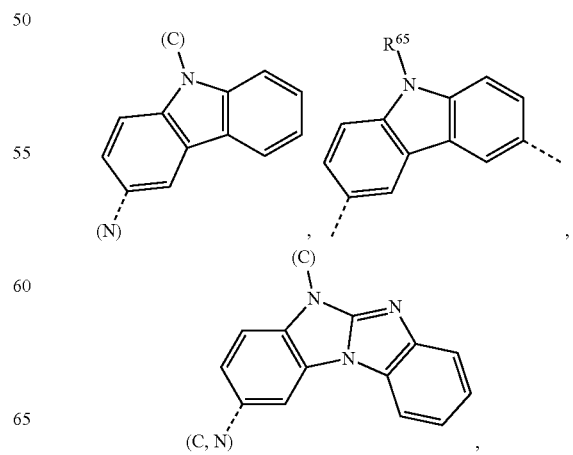

-continued (C)—has the meaning that the bonding site of the group $A^1$, $A^2$, $A^3$ or $A^4$ is linked to a C-atom, and (N)—has the meaning that the bonding site of the group $A^1$, $A^2$, $A^3$ or $A^4$ is linked to a N-atom.

5. A compound as claimed in claim 1, wherein:

$R^{10}$ is H or a group of the following formula:

-continued wherein when each of o, p, q and r are 0, $R^{10}$ is not H.

6. A compound as claimed in claim 1, wherein the compound has the formula (Ib):

(Ib)

wherein:
a is 0 or 1,
b is 1,
the sum of a and b is at least 1;
$X^1$ is a group of the following formula:

-continued

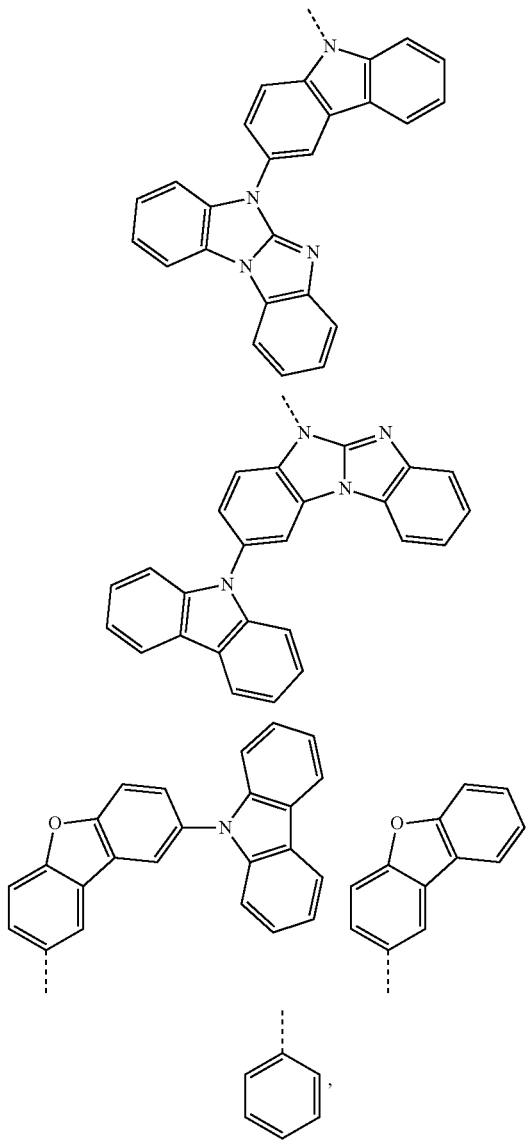

$X^3$ is a single bond $R^7$ is H or group of the following formula:

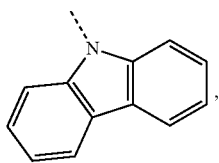

or $—SiR^{70}R^{71}R^{72}$, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl.

7. An electronic device, comprising a compound according to claim 1.

8. The electronic device according to claim 7, which is an electroluminescent device.

9. A charge transport layer, a charge/exciton blocker layer, or an emitting layer, comprising a compound according to claim 1.

10. The emitting layer according to claim 9, comprising the compound as host material.

11. An apparatus selected from the group consisting of stationary visual display units: mobile visual display units; illumination units; keyboards; items of clothing; furniture; wallpaper, comprising the organic electronic device according to claim 7.

12. An article, comprising the compound of claim 1, wherein the article is selected from the group consisting of an electrophotographic photoreceptor, a photoreceptors, photoelectric converter, an organic solar cell, a switching element, an organic light emitting field effect transistor, an image sensor, a dye laser and an electroluminescent device.

13. The emitting layer according to claim 9, comprising at least one compound of formula I as TADF emitter or as TADF host material in combination with at least one fluorescent emitter.

14. An apparatus selected from the group consisting of stationary visual display unit, mobile visual display unit, illumination unit, keyboard, item of clothing, furniture, wallpaper, said apparatus comprising the charge transport layer, the charge/exciton blocker layer, or the emitting layer according to claim 9.

* * * * *